(12) United States Patent
Felder et al.

(10) Patent No.: US 9,113,879 B2
(45) Date of Patent: *Aug. 25, 2015

(54) DEVICES AND METHODS FOR ENDOLUMINAL PLICATION

(75) Inventors: Kevin D. Felder, Cincinnati, OH (US); Lawrence Crainich, Charlestown, NH (US); Justin W. Sherrill, Alpharetta, GA (US); Jason L. Harris, Hamilton, OH (US); Mark S. Zeiner, Mason, OH (US); Brian F. DiNardo, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 649 days.

This patent is subject to a terminal disclaimer.

(21) Appl. No.: 13/326,657

(22) Filed: Dec. 15, 2011

(65) Prior Publication Data

US 2013/0153625 A1    Jun. 20, 2013

(51) Int. Cl.
*A61B 17/068* (2006.01)
*A61B 17/072* (2006.01)
(Continued)

(52) U.S. Cl.
CPC ........... *A61B 17/072* (2013.01); *A61B 19/5212* (2013.01); *A61B 17/00234* (2013.01);
(Continued)

(58) Field of Classification Search
CPC ................. A61B 17/00234; A61B 17/07207; A61B 17/072; A61B 17/068; A61B 2017/00827; A61B 2017/306; A61B 2017/00323; A61B 2017/00818; A61B 2017/2929; A61B 2017/00685; A61B 2017/2927; A61B 2017/00561; A61B 19/5212
USPC .......... 227/175.1, 176.1, 175.2, 180.1, 181.1; 606/151
See application file for complete search history.

(56) References Cited

U.S. PATENT DOCUMENTS

| | | |
|---|---|---|
| 2,069,878 A | 2/1937 | Flood |
| 3,470,834 A | 10/1969 | Bone |

(Continued)

FOREIGN PATENT DOCUMENTS

| | | |
|---|---|---|
| EP | 0 330 135 B1 | 5/1994 |
| EP | 0 641 546 A1 | 3/1995 |

(Continued)

OTHER PUBLICATIONS

U.S. Appl. No. 12/975,685, entitled, "Endoluminal Fold Creation," filed Dec. 22, 2010.

(Continued)

*Primary Examiner* — Thanh Truong
*Assistant Examiner* — Joshua Kotis
(74) *Attorney, Agent, or Firm* — Nutter McClennen & Fish LLP

(57) ABSTRACT

Devices and methods are provided for forming and securing a tissue plication. More particularly, the devices and methods of the present invention can be used to create multiple tissue folds on an anterior and posterior wall of a stomach cavity to reduce the volume thereof. In one aspect, a tissue acquisition and fixation system is disclosed that includes an elongate shaft, a staple applying assembly having a proximal end coupled to the distal end of the elongate shaft and having first and second jaws, and a tissue acquisition member coupled to the staple applying assembly by a linkage mechanism. The linkage mechanism is configured to move the tissue acquisition member between a first position that is longitudinally offset and proximal to the staple applying assembly, and a second position that is longitudinally adjacent to the staple applying assembly.

19 Claims, 56 Drawing Sheets

(51) Int. Cl.
  *A61B 17/064* (2006.01)
  *A61B 19/00* (2006.01)
  *A61B 17/00* (2006.01)
  *A61B 17/30* (2006.01)
  *A61B 17/29* (2006.01)

(52) U.S. Cl.
  CPC . *A61B17/07207* (2013.01); *A61B 2017/00323* (2013.01); *A61B 2017/00349* (2013.01); *A61B 2017/00561* (2013.01); *A61B 2017/00685* (2013.01); *A61B 2017/00818* (2013.01); *A61B 2017/2927* (2013.01); *A61B 2017/2929* (2013.01); *A61B 2017/306* (2013.01)

(56) References Cited

U.S. PATENT DOCUMENTS

| | | |
|---|---|---|
| 3,694,819 A | 10/1972 | Meyer |
| 3,802,438 A | 4/1974 | Wolvek |
| 3,890,970 A | 6/1975 | Gullen |
| 3,910,281 A | 10/1975 | Kletschka et al. |
| 3,990,619 A | 11/1976 | Russell |
| 4,006,747 A | 2/1977 | Kronenthal et al. |
| 4,022,191 A | 5/1977 | Jamshidi |
| 4,130,647 A | 12/1978 | Taylor |
| 4,216,777 A | 8/1980 | Pridemore |
| 4,235,238 A | 11/1980 | Ogiu et al. |
| 4,250,887 A | 2/1981 | Dardik et al. |
| 4,396,139 A | 8/1983 | Hall et al. |
| 4,669,473 A | 6/1987 | Richards et al. |
| 4,705,040 A | 11/1987 | Mueller et al. |
| 4,741,330 A | 5/1988 | Hayhurst |
| 4,750,492 A | 6/1988 | Jacobs |
| 4,791,937 A | 12/1988 | Wang |
| 4,805,628 A | 2/1989 | Fry et al. |
| 4,841,888 A | 6/1989 | Mills et al. |
| 4,869,259 A | 9/1989 | Elkins |
| 4,899,745 A | 2/1990 | Laboureau et al. |
| 5,015,249 A * | 5/1991 | Nakao et al. .................. 606/142 |
| 5,037,021 A | 8/1991 | Mills et al. |
| 5,041,129 A | 8/1991 | Hayhurst et al. |
| 5,046,513 A | 9/1991 | Gatturna et al. |
| 5,078,731 A | 1/1992 | Hayhurst |
| 5,080,663 A | 1/1992 | Mills et al. |
| 5,081,997 A | 1/1992 | Bosley, Jr. et al. |
| 5,123,914 A | 6/1992 | Cope |
| RE34,021 E | 8/1992 | Mueller et al. |
| 5,171,251 A | 12/1992 | Bregen et al. |
| 5,217,486 A | 6/1993 | Rice et al. |
| 5,258,000 A | 11/1993 | Gianturco |
| 5,258,015 A | 11/1993 | Li et al. |
| 5,268,001 A | 12/1993 | Nicholson et al. |
| 5,269,809 A | 12/1993 | Hayhurst et al. |
| 5,282,832 A | 2/1994 | Toso et al. |
| 5,307,924 A | 5/1994 | Manosalva et al. |
| 5,320,630 A | 6/1994 | Ahmed |
| 5,330,442 A | 7/1994 | Green et al. |
| 5,341,823 A | 8/1994 | Manosalva et al. |
| 5,354,298 A | 10/1994 | Lee et al. |
| 5,356,413 A | 10/1994 | Martins et al. |
| 5,366,459 A | 11/1994 | Yoon |
| 5,368,599 A | 11/1994 | Hirsch et al. |
| 5,376,101 A | 12/1994 | Green et al. |
| 5,383,905 A | 1/1995 | Golds et al. |
| 5,403,326 A | 4/1995 | Harrison et al. |
| 5,403,348 A | 4/1995 | Bonutti |
| 5,405,354 A | 4/1995 | Sarrett |
| 5,409,499 A | 4/1995 | Yi |
| 5,431,666 A | 7/1995 | Sauer et al. |
| 5,437,680 A | 8/1995 | Yoon |
| 5,462,558 A | 10/1995 | Kolesa et al. |
| 5,462,559 A | 10/1995 | Ahmed |
| 5,464,425 A | 11/1995 | Skiba |
| 5,470,337 A | 11/1995 | Moss |
| 5,472,452 A | 12/1995 | Trott |
| 5,474,572 A | 12/1995 | Hayhurst |
| 5,484,451 A | 1/1996 | Akopov et al. |
| 5,486,197 A | 1/1996 | Le et al. |
| 5,514,159 A | 5/1996 | Matula et al. |
| 5,520,702 A | 5/1996 | Sauer et al. |
| 5,522,843 A | 6/1996 | Zang |
| 5,531,678 A | 7/1996 | Tomba et al. |
| 5,531,699 A | 7/1996 | Tomba et al. |
| 5,540,704 A | 7/1996 | Gordon et al. |
| 5,545,141 A | 8/1996 | Eld |
| 5,549,630 A | 8/1996 | Bonutti |
| 5,562,686 A | 10/1996 | Sauer et al. |
| 5,584,861 A | 12/1996 | Swain et al. |
| 5,584,862 A | 12/1996 | Bonutti |
| 5,591,180 A | 1/1997 | Hinchliffe |
| 5,591,202 A | 1/1997 | Slater et al. |
| 5,618,314 A | 4/1997 | Harwin et al. |
| 5,626,614 A | 5/1997 | Hart |
| 5,630,824 A | 5/1997 | Hart |
| 5,643,289 A | 7/1997 | Sauer et al. |
| 5,643,321 A | 7/1997 | McDevitt |
| 5,649,963 A | 7/1997 | McDevitt |
| 5,662,683 A | 9/1997 | Kay |
| 5,669,917 A | 9/1997 | Sauer et al. |
| 5,681,344 A | 10/1997 | Kelly |
| 5,681,351 A | 10/1997 | Jamiolkowski et al. |
| 5,683,418 A | 11/1997 | Luscombe et al. |
| 5,690,655 A | 11/1997 | Hart et al. |
| 5,695,504 A | 12/1997 | Gifford, III et al. |
| 5,725,529 A | 3/1998 | Nicholson et al. |
| 5,725,556 A | 3/1998 | Moser et al. |
| 5,728,116 A | 3/1998 | Rosenman |
| 5,728,119 A | 3/1998 | Smith et al. |
| 5,733,306 A | 3/1998 | Bonutti |
| 5,733,325 A | 3/1998 | Robinson et al. |
| 5,735,875 A | 4/1998 | Bonutti et al. |
| 5,741,277 A | 4/1998 | Gordon et al. |
| 5,755,730 A | 5/1998 | Swain et al. |
| 5,766,183 A | 6/1998 | Sauer |
| 5,792,153 A | 8/1998 | Swain et al. |
| 5,800,445 A | 9/1998 | Ratcliff et al. |
| 5,814,071 A | 9/1998 | McDevitt et al. |
| 5,826,776 A | 10/1998 | Schulze et al. |
| 5,885,294 A | 3/1999 | Pedlick et al. |
| 5,897,563 A | 4/1999 | Yoon et al. |
| 5,897,564 A | 4/1999 | Schulze et al. |
| 5,899,921 A | 5/1999 | Caspari et al. |
| 5,902,321 A | 5/1999 | Caspari et al. |
| 5,904,696 A | 5/1999 | Rosenman |
| 5,910,105 A | 6/1999 | Swain et al. |
| RE36,289 E | 8/1999 | Le et al. |
| 5,931,844 A | 8/1999 | Thompson et al. |
| 5,935,129 A | 8/1999 | McDevitt et al. |
| 5,941,900 A | 8/1999 | Bonutti |
| 5,944,724 A | 8/1999 | Lizardi |
| 5,948,000 A | 9/1999 | Larsen et al. |
| 5,954,747 A | 9/1999 | Clark |
| 5,961,538 A | 10/1999 | Pedlick et al. |
| 5,980,558 A | 11/1999 | Wiley |
| 6,010,515 A | 1/2000 | Swain et al. |
| 6,010,525 A | 1/2000 | Bonutti et al. |
| 6,036,694 A | 3/2000 | Goble et al. |
| 6,036,701 A | 3/2000 | Rosenman |
| 6,044,847 A | 4/2000 | Carter et al. |
| 6,045,574 A | 4/2000 | Thal |
| 6,051,247 A | 4/2000 | Hench et al. |
| 6,056,751 A | 5/2000 | Fenton, Jr. |
| 6,066,146 A | 5/2000 | Carroll et al. |
| 6,068,648 A | 5/2000 | Cole et al. |
| 6,071,289 A | 6/2000 | Stefanchik et al. |
| 6,077,292 A | 6/2000 | Bonutti |
| 6,086,608 A | 7/2000 | Ek et al. |
| 6,099,547 A | 8/2000 | Gellman et al. |
| 6,143,017 A | 11/2000 | Thal |
| 6,146,406 A | 11/2000 | Shluzas et al. |
| 6,149,669 A | 11/2000 | Li |
| 6,152,935 A | 11/2000 | Kammerer et al. |
| 6,159,234 A | 12/2000 | Bonutti et al. |
| 6,165,204 A | 12/2000 | Levinson et al. |

(56) References Cited

U.S. PATENT DOCUMENTS

| | | |
|---|---|---|
| 6,200,329 B1 | 3/2001 | Fung et al. |
| 6,206,895 B1 | 3/2001 | Levinson |
| 6,231,561 B1 | 5/2001 | Frazier et al. |
| 6,231,581 B1 | 5/2001 | Shank et al. |
| 6,231,592 B1 | 5/2001 | Bonutti et al. |
| 6,241,747 B1 | 6/2001 | Ruff |
| 6,245,082 B1 | 6/2001 | Gellman et al. |
| 6,287,325 B1 | 9/2001 | Bonutti |
| 6,293,961 B2 | 9/2001 | Schwartz |
| 6,302,886 B1 | 10/2001 | McDevitt et al. |
| 6,306,159 B1 | 10/2001 | Schwartz |
| 6,319,271 B1 | 11/2001 | Schwartz |
| 6,368,334 B1 | 4/2002 | Sauer |
| 6,372,245 B1 | 4/2002 | Bowman et al. |
| 6,405,733 B1 | 6/2002 | Fogarty et al. |
| 6,436,088 B2 | 8/2002 | Frazier et al. |
| 6,440,154 B2 | 8/2002 | Gellman et al. |
| 6,447,524 B1 | 9/2002 | Knodel et al. |
| 6,468,228 B1 | 10/2002 | Topel et al. |
| 6,468,293 B2 | 10/2002 | Bonutti et al. |
| 6,478,791 B1 | 11/2002 | Carter et al. |
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,524,328 B2 | 2/2003 | Levinson |
| 6,527,794 B1 | 3/2003 | McDevitt et al. |
| 6,527,795 B1 | 3/2003 | Lizardi |
| 6,533,796 B1 | 3/2003 | Sauer et al. |
| 6,558,400 B2 | 5/2003 | Deem et al. |
| 6,561,969 B2 | 5/2003 | Frazier et al. |
| 6,564,806 B1 | 5/2003 | Fogarty et al. |
| 6,566,484 B2 | 5/2003 | Gharda et al. |
| 6,569,187 B1 | 5/2003 | Bonutti et al. |
| 6,572,629 B2 | 6/2003 | Kalloo et al. |
| 6,575,987 B2 | 6/2003 | Gellman et al. |
| 6,582,453 B1 | 6/2003 | Tran et al. |
| 6,592,593 B1 | 7/2003 | Parodi et al. |
| 6,599,311 B1 | 7/2003 | Biggs et al. |
| 6,626,899 B2 | 9/2003 | Houser et al. |
| 6,652,561 B1 | 11/2003 | Tran |
| 6,652,562 B2 | 11/2003 | Collier et al. |
| 6,660,023 B2 | 12/2003 | McDevitt et al. |
| 6,663,639 B1 | 12/2003 | Laufer et al. |
| 6,669,687 B1 | 12/2003 | Saadat |
| 6,679,889 B1 | 1/2004 | West, Jr. et al. |
| 6,692,516 B2 | 2/2004 | West, Jr. et al. |
| 6,699,263 B2 | 3/2004 | Cope |
| 6,722,371 B1 | 4/2004 | Fogarty et al. |
| 6,733,531 B1 | 5/2004 | Trieu |
| 6,740,098 B2 | 5/2004 | Abrams et al. |
| 6,746,460 B2 | 6/2004 | Gannoe et al. |
| 6,769,590 B2 | 8/2004 | Vresh et al. |
| 6,773,440 B2 | 8/2004 | Gannoe et al. |
| 6,773,441 B1 | 8/2004 | Laufer et al. |
| 6,773,450 B2 | 8/2004 | Leung et al. |
| 6,780,198 B1 | 8/2004 | Gregoire et al. |
| 6,790,214 B2 | 9/2004 | Kraemer et al. |
| 6,800,081 B2 | 10/2004 | Parodi |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,881,816 B2 | 4/2005 | Gharda et al. |
| 6,884,248 B2 | 4/2005 | Bolduc et al. |
| 6,908,427 B2 | 6/2005 | Fleener et al. |
| 6,909,015 B2 | 6/2005 | Kemmish et al. |
| 6,916,327 B2 | 7/2005 | Northrup, III et al. |
| 6,923,754 B2 | 8/2005 | Lubock |
| 6,932,835 B2 | 8/2005 | Bonutti et al. |
| 6,960,217 B2 | 11/2005 | Bolduc |
| 6,966,919 B2 | 11/2005 | Sixto, Jr. et al. |
| 6,986,737 B2 | 1/2006 | Suzuki et al. |
| 6,986,775 B2 | 1/2006 | Morales et al. |
| 6,988,985 B2 | 1/2006 | Suzuki et al. |
| 6,991,643 B2 | 1/2006 | Saadat |
| 6,994,715 B2 | 2/2006 | Gannoe et al. |
| 6,997,931 B2 | 2/2006 | Sauer et al. |
| 6,997,932 B2 | 2/2006 | Dreyfuss et al. |
| 7,001,400 B1 | 2/2006 | Modesitt et al. |
| 7,001,410 B2 | 2/2006 | Fisher et al. |
| 7,016,735 B2 | 3/2006 | Imran et al. |
| 7,020,531 B1 | 3/2006 | Colliou et al. |
| 7,029,481 B1 | 4/2006 | Burdulis, Jr. et al. |
| 7,033,370 B2 | 4/2006 | Gordon et al. |
| 7,033,378 B2 | 4/2006 | Smith et al. |
| 7,033,380 B2 | 4/2006 | Schwartz et al. |
| 7,037,315 B2 | 5/2006 | Sancoff et al. |
| 7,041,111 B2 | 5/2006 | Chu |
| 7,044,934 B2 | 5/2006 | Mickley |
| 7,048,749 B2 | 5/2006 | Kortenbach et al. |
| 7,048,755 B2 | 5/2006 | Bonutti et al. |
| 7,063,715 B2 | 6/2006 | Onuki et al. |
| 7,083,629 B2 | 8/2006 | Weller et al. |
| 7,083,630 B2 | 8/2006 | DeVries et al. |
| 7,097,650 B2 | 8/2006 | Weller et al. |
| 7,153,314 B2 | 12/2006 | Laufer et al. |
| 7,160,312 B2 | 1/2007 | Saadat |
| 7,175,638 B2 | 2/2007 | Gannoe et al. |
| 7,175,648 B2 | 2/2007 | Nakao |
| 7,214,233 B2 | 5/2007 | Gannoe et al. |
| 7,217,425 B2 | 5/2007 | Serhan et al. |
| 7,306,614 B2 | 12/2007 | Weller et al. |
| 7,347,863 B2 | 3/2008 | Rothe et al. |
| 7,361,180 B2 | 4/2008 | Saadat et al. |
| 7,390,329 B2 | 6/2008 | Westra et al. |
| 7,416,554 B2 | 8/2008 | Lam et al. |
| 7,431,725 B2 | 10/2008 | Stack et al. |
| 7,503,922 B2 | 3/2009 | Deem et al. |
| 7,641,671 B2 | 1/2010 | Crainich |
| 7,708,181 B2 * | 5/2010 | Cole et al. ............... 227/176.1 |
| 7,757,924 B2 * | 7/2010 | Gerbi et al. ............. 227/175.1 |
| 7,934,631 B2 | 5/2011 | Balbierz et al. |
| 8,007,505 B2 * | 8/2011 | Weller et al. ................ 606/153 |
| 8,092,378 B2 | 1/2012 | Roth et al. |
| 8,257,365 B2 * | 9/2012 | Demarais et al. ........... 606/139 |
| 8,449,560 B2 * | 5/2013 | Roth et al. .................. 606/151 |
| 8,469,252 B2 * | 6/2013 | Holcomb et al. ......... 227/175.1 |
| 8,469,977 B2 * | 6/2013 | Balbierz et al. ............ 606/153 |
| 2001/0010005 A1 | 7/2001 | Kammerer et al. |
| 2001/0044656 A1 | 11/2001 | Williamson et al. |
| 2002/0010390 A1 | 1/2002 | Guice et al. |
| 2002/0028980 A1 | 3/2002 | Thierfelder et al. |
| 2002/0059938 A1 | 5/2002 | Fogarty et al. |
| 2002/0077661 A1 | 6/2002 | Saadat |
| 2002/0111653 A1 | 8/2002 | Foerster |
| 2002/0116070 A1 | 8/2002 | Amara et al. |
| 2002/0123758 A1 | 9/2002 | Bachman et al. |
| 2002/0128684 A1 | 9/2002 | Foerster |
| 2002/0156150 A1 | 10/2002 | Williams et al. |
| 2002/0169465 A1 | 11/2002 | Bowman et al. |
| 2002/0188305 A1 | 12/2002 | Foerster et al. |
| 2002/0189622 A1 | 12/2002 | Cauthen et al. |
| 2003/0004578 A1 | 1/2003 | Brown et al. |
| 2003/0018358 A1 | 1/2003 | Saadat |
| 2003/0023268 A1 | 1/2003 | Lizardi |
| 2003/0069593 A1 | 4/2003 | Tremulis et al. |
| 2003/0093117 A1 | 5/2003 | Saadat |
| 2003/0097150 A1 | 5/2003 | Fallin et al. |
| 2003/0109900 A1 | 6/2003 | Martinek |
| 2003/0125767 A1 | 7/2003 | Collier et al. |
| 2003/0158581 A1 | 8/2003 | Levinson |
| 2003/0163143 A1 | 8/2003 | Wakabayashi |
| 2003/0163160 A1 | 8/2003 | O'Malley et al. |
| 2003/0171760 A1 | 9/2003 | Gambale |
| 2003/0181800 A1 | 9/2003 | Bonutti |
| 2003/0181926 A1 | 9/2003 | Dana et al. |
| 2003/0191497 A1 | 10/2003 | Cope |
| 2003/0216613 A1 | 11/2003 | Suzuki et al. |
| 2003/0220685 A1 | 11/2003 | Hlavka et al. |
| 2003/0233056 A1 | 12/2003 | Saadat et al. |
| 2003/0236535 A1 | 12/2003 | Onuki et al. |
| 2003/0236573 A1 | 12/2003 | Evans et al. |
| 2004/0010245 A1 | 1/2004 | Cerier et al. |

(56) References Cited

U.S. PATENT DOCUMENTS

| | | |
|---|---|---|
| 2004/0049211 A1 | 3/2004 | Tremulis et al. |
| 2004/0059416 A1 | 3/2004 | Murray et al. |
| 2004/0073219 A1 | 4/2004 | Skiba et al. |
| 2004/0092892 A1 | 5/2004 | Kagan et al. |
| 2004/0093023 A1 | 5/2004 | Allen et al. |
| 2004/0093057 A1 | 5/2004 | Bolduc et al. |
| 2004/0098050 A1 | 5/2004 | Foerster et al. |
| 2004/0102809 A1 | 5/2004 | Anderson |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0133220 A1 | 7/2004 | Lashinski et al. |
| 2004/0133238 A1 | 7/2004 | Cerier |
| 2004/0138525 A1 | 7/2004 | Saadat et al. |
| 2004/0138529 A1 | 7/2004 | Wiltshire et al. |
| 2004/0144395 A1 | 7/2004 | Evans et al. |
| 2004/0147958 A1 | 7/2004 | Lam et al. |
| 2004/0153008 A1 | 8/2004 | Sharf et al. |
| 2004/0153103 A1 | 8/2004 | Schwartz et al. |
| 2004/0162568 A1 | 8/2004 | Saadat et al. |
| 2004/0167546 A1 | 8/2004 | Saadat et al. |
| 2004/0186514 A1 | 9/2004 | Swain et al. |
| 2004/0186566 A1 | 9/2004 | Hindrichs et al. |
| 2004/0193184 A1 | 9/2004 | Laufer et al. |
| 2004/0193190 A1 | 9/2004 | Liddicoat et al. |
| 2004/0193191 A1 | 9/2004 | Starksen et al. |
| 2004/0194790 A1 | 10/2004 | Laufer et al. |
| 2004/0199059 A1 | 10/2004 | Brauker et al. |
| 2004/0215216 A1 | 10/2004 | Gannoe et al. |
| 2004/0225183 A1 | 11/2004 | Michlitsch et al. |
| 2004/0225305 A1 | 11/2004 | Ewers et al. |
| 2004/0243178 A1 | 12/2004 | Haut et al. |
| 2004/0243227 A1 | 12/2004 | Starksen et al. |
| 2004/0249367 A1 | 12/2004 | Saadat et al. |
| 2004/0249392 A1 | 12/2004 | Mikkaichi et al. |
| 2004/0260344 A1 | 12/2004 | Lyons et al. |
| 2005/0019368 A1 | 1/2005 | Cook et al. |
| 2005/0033319 A1 | 2/2005 | Gambale et al. |
| 2005/0033328 A1 | 2/2005 | Laufer et al. |
| 2005/0033403 A1 | 2/2005 | Ward et al. |
| 2005/0038437 A1 | 2/2005 | McDevitt et al. |
| 2005/0049617 A1 | 3/2005 | Chatlynne et al. |
| 2005/0055052 A1 | 3/2005 | Lombardo et al. |
| 2005/0055087 A1 | 3/2005 | Starksen |
| 2005/0055089 A1 | 3/2005 | Macoviak et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0070931 A1 | 3/2005 | Li et al. |
| 2005/0075653 A1 | 4/2005 | Saadat et al. |
| 2005/0075654 A1 | 4/2005 | Kelleher |
| 2005/0085903 A1 | 4/2005 | Lau |
| 2005/0096673 A1 | 5/2005 | Stack et al. |
| 2005/0101977 A1 | 5/2005 | Gannoe et al. |
| 2005/0107663 A1 | 5/2005 | Saadat et al. |
| 2005/0113640 A1 | 5/2005 | Saadat et al. |
| 2005/0113851 A1 | 5/2005 | Swain et al. |
| 2005/0119735 A1 | 6/2005 | Spence et al. |
| 2005/0142163 A1 | 6/2005 | Hunter et al. |
| 2005/0143762 A1 | 6/2005 | Paraschac et al. |
| 2005/0165429 A1 | 7/2005 | Douglas et al. |
| 2005/0177176 A1 | 8/2005 | Gerbi et al. |
| 2005/0187565 A1 | 8/2005 | Baker et al. |
| 2005/0187567 A1 | 8/2005 | Baker et al. |
| 2005/0192599 A1 | 9/2005 | Demarais |
| 2005/0192601 A1 | 9/2005 | Demarais |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0203547 A1 | 9/2005 | Weller et al. |
| 2005/0203548 A1 | 9/2005 | Weller et al. |
| 2005/0215945 A1 | 9/2005 | Harris et al. |
| 2005/0222592 A1 | 10/2005 | Gannoe et al. |
| 2005/0222678 A1 | 10/2005 | Lashinski et al. |
| 2005/0228410 A1 | 10/2005 | Berreklouw |
| 2005/0234512 A1 | 10/2005 | Nakao |
| 2005/0245945 A1 | 11/2005 | Ewers et al. |
| 2005/0247320 A1 | 11/2005 | Stack et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0256531 A9 | 11/2005 | Bolduc et al. |
| 2005/0256533 A1 | 11/2005 | Roth et al. |
| 2005/0261708 A1 | 11/2005 | Pasricha et al. |
| 2005/0261709 A1 | 11/2005 | Sakamoto et al. |
| 2005/0261710 A1 | 11/2005 | Sakamoto et al. |
| 2005/0261712 A1 | 11/2005 | Balbierz et al. |
| 2005/0267495 A1 | 12/2005 | Ginn et al. |
| 2005/0267534 A1 | 12/2005 | Bonutti et al. |
| 2005/0273138 A1 | 12/2005 | To et al. |
| 2005/0277957 A1 | 12/2005 | Kuhns et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2005/0288688 A1 | 12/2005 | Sakamoto et al. |
| 2005/0288689 A1 | 12/2005 | Kammerer et al. |
| 2005/0288708 A1 | 12/2005 | Kammerer et al. |
| 2006/0004385 A1 | 1/2006 | Gellman et al. |
| 2006/0004409 A1 | 1/2006 | Nobis et al. |
| 2006/0004410 A1 | 1/2006 | Nobis et al. |
| 2006/0009789 A1 | 1/2006 | Gambale et al. |
| 2006/0009792 A1 | 1/2006 | Baker et al. |
| 2006/0015125 A1 | 1/2006 | Swain |
| 2006/0020162 A1 | 1/2006 | Whayne et al. |
| 2006/0020167 A1 | 1/2006 | Sitzmann |
| 2006/0020254 A1 | 1/2006 | Hoffmann |
| 2006/0020274 A1 | 1/2006 | Ewers et al. |
| 2006/0020276 A1 | 1/2006 | Saadat et al. |
| 2006/0020277 A1 | 1/2006 | Gostout et al. |
| 2006/0020278 A1 | 1/2006 | Burnett et al. |
| 2006/0025652 A1 | 2/2006 | Vargas |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0041263 A1 | 2/2006 | Chu et al. |
| 2006/0047289 A1 | 3/2006 | Fogel |
| 2006/0052801 A1 | 3/2006 | Dreyfuss et al. |
| 2006/0052824 A1 | 3/2006 | Ransick et al. |
| 2006/0052825 A1 | 3/2006 | Ransick et al. |
| 2006/0058582 A1 | 3/2006 | Maahs et al. |
| 2006/0079914 A1 | 4/2006 | Modesitt et al. |
| 2006/0100643 A1 | 5/2006 | Laufer et al. |
| 2006/0106405 A1 | 5/2006 | Fann et al. |
| 2006/0135996 A1 | 6/2006 | Schwartz et al. |
| 2006/0151568 A1 | 7/2006 | Weller et al. |
| 2006/0157067 A1 | 7/2006 | Saadat et al. |
| 2006/0161185 A1 | 7/2006 | Saadat et al. |
| 2006/0178560 A1 | 8/2006 | Saadat et al. |
| 2006/0271073 A1 | 11/2006 | Lam et al. |
| 2006/0271101 A1 | 11/2006 | Saadat et al. |
| 2006/0276810 A1 | 12/2006 | Kelleher et al. |
| 2007/0060932 A1 | 3/2007 | Stack et al. |
| 2007/0112364 A1 | 5/2007 | Gerbi et al. |

(56) References Cited

U.S. PATENT DOCUMENTS

| | | | |
|---|---|---|---|
| 2007/0162056 A1* | 7/2007 | Gerbi et al. | 606/153 |
| 2007/0167960 A1 | 7/2007 | Roth et al. | |
| 2007/0175488 A1 | 8/2007 | Cox et al. | |
| 2007/0181138 A1 | 8/2007 | Gannoe et al. | |
| 2007/0191871 A1 | 8/2007 | Baker et al. | |
| 2007/0208360 A1 | 9/2007 | Demarais et al. | |
| 2007/0219566 A1 | 9/2007 | Gambale | |
| 2007/0219571 A1 | 9/2007 | Balbierz et al. | |
| 2007/0225737 A1 | 9/2007 | Messerly et al. | |
| 2007/0233161 A1 | 10/2007 | Weller et al. | |
| 2007/0276432 A1 | 11/2007 | Stack et al. | |
| 2008/0039879 A1 | 2/2008 | Chin et al. | |
| 2008/0051823 A1 | 2/2008 | Makower et al. | |
| 2008/0065122 A1 | 3/2008 | Stack et al. | |
| 2008/0086155 A1 | 4/2008 | Rothe et al. | |
| 2008/0091079 A1 | 4/2008 | Roth et al. | |
| 2008/0103357 A1 | 5/2008 | Zeiner et al. | |
| 2008/0132925 A1 | 6/2008 | Demarais | |
| 2008/0147112 A1 | 6/2008 | Sheets et al. | |
| 2008/0172074 A1 | 7/2008 | Baker et al. | |
| 2008/0177304 A1 | 7/2008 | Westra et al. | |
| 2008/0190989 A1 | 8/2008 | Crews et al. | |
| 2008/0207995 A1 | 8/2008 | Kortenbach et al. | |
| 2008/0208214 A1 | 8/2008 | Sato et al. | |
| 2008/0208216 A1 | 8/2008 | Cerier | |
| 2008/0228199 A1 | 9/2008 | Cropper et al. | |
| 2008/0228203 A1 | 9/2008 | Bell et al. | |
| 2008/0234703 A1* | 9/2008 | Cropper et al. | 606/142 |
| 2008/0234705 A1 | 9/2008 | Cropper et al. | |
| 2008/0249561 A1 | 10/2008 | Stokes et al. | |
| 2008/0249566 A1 | 10/2008 | Harris et al. | |
| 2008/0294179 A1* | 11/2008 | Balbierz et al. | 606/151 |
| 2009/0024144 A1 | 1/2009 | Zeiner et al. | |
| 2009/0024163 A1 | 1/2009 | Zeiner et al. | |
| 2009/0125040 A1 | 5/2009 | Hambly et al. | |
| 2009/0276055 A1 | 11/2009 | Harris et al. | |
| 2010/0082046 A1 | 4/2010 | Harris et al. | |
| 2010/0116867 A1* | 5/2010 | Balbierz et al. | 227/175.1 |
| 2011/0066167 A1 | 3/2011 | Harris et al. | |
| 2013/0153622 A1 | 6/2013 | Felder et al. | |
| 2013/0153623 A1 | 6/2013 | Felder et al. | |
| 2013/0153624 A1 | 6/2013 | Felder et al. | |
| 2013/0153626 A1 | 6/2013 | Felder et al. | |
| 2013/0153642 A1 | 6/2013 | Felder et al. | |

FOREIGN PATENT DOCUMENTS

| | | |
|---|---|---|
| EP | 0 519 704 B1 | 10/1996 |
| EP | 0 579 495 B1 | 9/1997 |
| EP | 0 634 142 B1 | 3/1998 |
| EP | 0 558 993 B1 | 4/1998 |
| EP | 0 838 197 A2 | 4/1998 |
| EP | 0 669 102 B1 | 10/1998 |
| EP | 0 768 839 B1 | 12/1998 |
| EP | 0 688 186 B1 | 4/1999 |
| EP | 0 676 953 B1 | 5/1999 |
| EP | 0 751 745 B1 | 5/1999 |
| EP | 0 598 588 B1 | 7/1999 |
| EP | 0 669 103 B1 | 9/1999 |
| EP | 0 768 837 B1 | 5/2000 |
| EP | 0 676 952 B1 | 7/2000 |
| EP | 1 098 597 A1 | 5/2001 |
| EP | 0 674 875 B1 | 11/2001 |
| EP | 0 643 945 B1 | 3/2002 |
| EP | 0 835 642 B1 | 8/2002 |
| EP | 0 746 239 B1 | 9/2002 |
| EP | 0 785 751 B1 | 1/2003 |
| EP | 0 748 612 B1 | 2/2003 |
| EP | 1 284 661 A1 | 2/2003 |
| EP | 0 834 281 B1 | 3/2003 |
| EP | 0 782 411 B1 | 8/2003 |
| EP | 1 334 695 A1 | 8/2003 |
| EP | 0 847 727 B1 | 2/2004 |
| EP | 1 202 672 B1 | 3/2004 |
| EP | 1 346 699 B1 | 1/2005 |
| EP | 1 530 441 A2 | 5/2005 |
| EP | 1 281 355 B1 | 9/2005 |
| EP | 1 067 872 B1 | 3/2006 |
| EP | 1 631 201 A1 | 3/2006 |
| EP | 1 648 279 A2 | 4/2006 |
| EP | 1 656 891 A1 | 5/2006 |
| EP | 1 628 581 B1 | 3/2007 |
| EP | 1 584 295 B1 | 2/2008 |
| EP | 1 386 585 B1 | 4/2008 |
| EP | 1 632 186 B1 | 6/2008 |
| EP | 1 658 010 B1 | 6/2008 |
| EP | 1 629 780 B1 | 9/2008 |
| EP | 1 507 481 B1 | 12/2008 |
| EP | 1 392 179 B1 | 9/2009 |
| EP | 0 951 238 B1 | 4/2010 |
| EP | 1 259 155 B1 | 12/2010 |
| EP | 1 447 052 B1 | 2/2012 |
| EP | 1 602 336 B1 | 4/2012 |
| GB | 1 549 666 A | 8/1979 |
| JP | 2004-160255 A | 6/2004 |
| JP | 2004-216192 A | 8/2004 |
| JP | 2004-358045 A | 12/2004 |
| WO | 92/04870 A1 | 4/1992 |
| WO | 94/14416 A1 | 7/1994 |
| WO | 94/14417 A1 | 7/1994 |
| WO | 94/15535 A1 | 7/1994 |
| WO | 95/29637 A1 | 11/1995 |
| WO | 96/14797 A1 | 5/1996 |
| WO | 96/14798 A1 | 5/1996 |
| WO | 96/41574 A2 | 12/1996 |
| WO | 97/24988 A1 | 7/1997 |
| WO | 99/02107 A1 | 1/1999 |
| WO | 00/57796 A1 | 10/2000 |
| WO | 00/61012 A1 | 10/2000 |
| WO | 00/69345 A1 | 11/2000 |
| WO | 00/74565 A1 | 12/2000 |
| WO | 01/10312 A1 | 2/2001 |
| WO | 01/66001 A2 | 9/2001 |
| WO | 01/66018 A1 | 9/2001 |
| WO | 01/89393 A1 | 11/2001 |
| WO | 02/30293 A1 | 4/2002 |
| WO | 02/087481 A1 | 11/2002 |
| WO | 02/094108 A2 | 11/2002 |
| WO | 03/007796 A2 | 1/2003 |
| WO | 03/065904 A1 | 8/2003 |
| WO | 03/077772 A1 | 9/2003 |
| WO | 03/096910 A1 | 11/2003 |
| WO | 2004/004577 A2 | 1/2004 |
| WO | 2004/014237 A1 | 2/2004 |
| WO | 2004/019788 A2 | 3/2004 |
| WO | 2004/024006 A1 | 3/2004 |
| WO | 2004/041119 A2 | 5/2004 |
| WO | 2004/045378 A2 | 6/2004 |
| WO | 2004/049958 A1 | 6/2004 |
| WO | 2004/086984 A1 | 10/2004 |
| WO | 2004/103189 A1 | 12/2004 |
| WO | 2004/103430 A2 | 12/2004 |
| WO | 2004/105620 A1 | 12/2004 |
| WO | 2005/011463 A2 | 2/2005 |
| WO | 2005/011519 A2 | 2/2005 |
| WO | 2005/020802 A2 | 3/2005 |
| WO | 2005/027754 A1 | 3/2005 |
| WO | 2005/034729 A2 | 4/2005 |
| WO | 2005/039428 A2 | 5/2005 |
| WO | 2005/058239 A2 | 6/2005 |
| WO | 2005/060882 A2 | 7/2005 |
| WO | 2005/086945 A2 | 9/2005 |
| WO | 2005/094933 A2 | 10/2005 |
| WO | 2005/096958 A2 | 10/2005 |
| WO | 2005/096994 A1 | 10/2005 |
| WO | 2005/099591 A2 | 10/2005 |
| WO | 2005/107650 A2 | 11/2005 |
| WO | 2005/110241 A1 | 11/2005 |
| WO | 2005/110244 A1 | 11/2005 |
| WO | 2005/110280 A2 | 11/2005 |
| WO | 2005/112784 A2 | 12/2005 |
| WO | 2005/112785 A2 | 12/2005 |
| WO | 2005/112786 A2 | 12/2005 |

(56) References Cited

FOREIGN PATENT DOCUMENTS

| | | |
|---|---|---|
| WO | 2005/112797 A1 | 12/2005 |
| WO | 2005/115256 A2 | 12/2005 |
| WO | 2005/122914 A2 | 12/2005 |
| WO | 2005/122954 A1 | 12/2005 |
| WO | 2006/007576 A2 | 1/2006 |
| WO | WO 2006007576 A2 * | 1/2006 |
| WO | 2006/019868 A2 | 2/2006 |
| WO | 2006/023165 A2 | 3/2006 |
| WO | 2006/034484 A2 | 3/2006 |
| WO | 2006/037639 A1 | 4/2006 |
| WO | 2006/039199 A2 | 4/2006 |
| WO | 2006/039223 A2 | 4/2006 |
| WO | 2006/039296 A2 | 4/2006 |
| WO | 2006/044837 A2 | 4/2006 |
| WO | 2006/055388 A2 | 5/2006 |
| WO | 2006/055804 A2 | 5/2006 |
| WO | 2006/134106 A1 | 12/2006 |
| WO | 2007/019268 A2 | 2/2007 |
| WO | 2007/095096 A2 | 8/2007 |
| WO | 2008/043044 A2 | 4/2008 |
| WO | 2008/087635 A2 | 7/2008 |
| WO | 2008/088850 A2 | 7/2008 |
| WO | 2008/112942 A2 | 9/2008 |

OTHER PUBLICATIONS

U.S. Appl. No. 12/975,691, entitled, "Endoluminal Fold Creation," filed Dec. 22, 2010.
U.S. Appl. No. 13/164,963, entitled, "A Method of Using a Surgical Stapler to Secure a Tissue Fold," filed Jun. 21, 2011.
International Search Report and Written Opinion for Application No. PCT/US2012/068133 mailed May 27, 2013 (20 Pages).

\* cited by examiner

4000

FIG. 46A  FIG. 46B  FIG. 46C
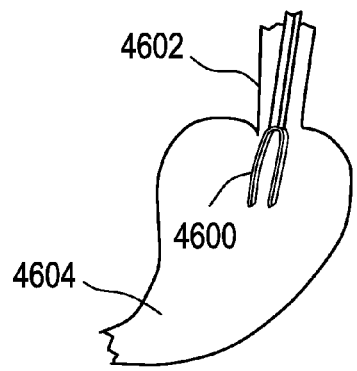 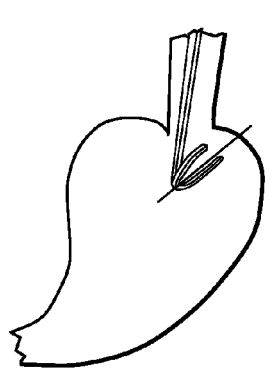 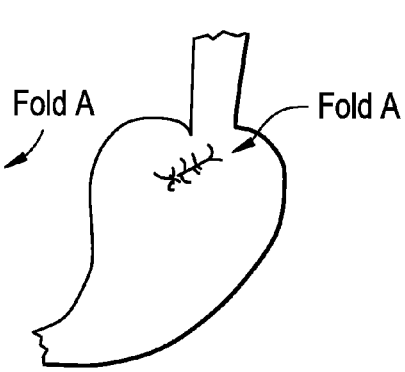
FIG. 47A  FIG. 47B  FIG. 47C
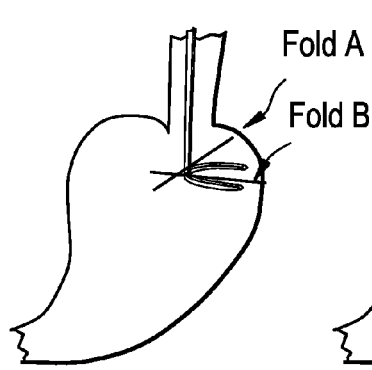 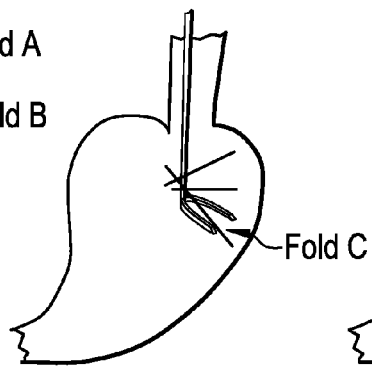 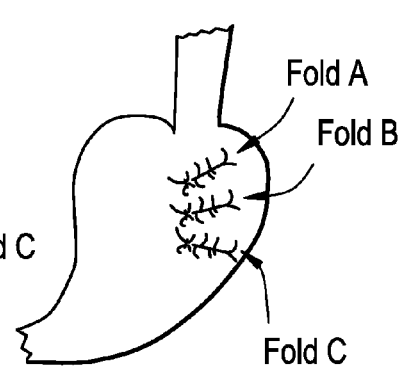

DEVICES AND METHODS FOR ENDOLUMINAL PLICATION

FIELD

This invention is related generally to devices and methods for performing surgical procedures, and more particularly to endoscopic devices and methods for forming an endoluminal plication to reduce the volume of the gastric cavity.

BACKGROUND

Metabolic disease is a serious medical condition that affects more than 30% of the U.S. population and can contribute significantly to morbidity and mortality. Complications associated with metabolic disease include obesity, hypertension, diabetes, coronary artery disease, stroke, congestive heart failure, multiple orthopedic problems, pulmonary insufficiency, sleep apnea, infertility, and markedly decreased life expectancy. Additionally, the complications or co-morbidities associated with metabolic disease, such as obesity, often affect an individual's quality of life. Accordingly, the monetary, physical, and psychological costs associated with metabolic disease can be substantial. For example, it is estimated that costs related to obesity alone exceed more than 100 billion dollars annually.

A variety of bariatric surgical procedures have been developed to treat complications of metabolic disease, such as obesity. The most common of these is the Roux-en-Y gastric bypass (RYGB). In a RYGB procedure, a small stomach pouch is separated from the remainder of the gastric cavity and attached to a resectioned portion of the small intestine. However, because this complex procedure requires a great deal of operative time, as well as extended and often painful post-operative recovery, the RYGB procedure is generally only utilized to treat people with morbid obesity.

In view of the highly invasive nature of the RYGB procedure, other less invasive bariatric procedures have been developed such as the Fobi pouch, bilio-pancreatic diversion, gastroplasty ("stomach stapling"), vertical sleeve gastrectomy, and gastric banding. In addition, implantable devices are known which limit the passage of food through the stomach. Gastric banding procedures, for example, involve the placement of a small band around the stomach near the junction of the stomach and the esophagus to restrict the passage from one part of the digestive tract to another, thereby affecting a patient's feeling of satiety.

While the above-described bariatric procedures are commonly used for the treatment of morbid obesity (i.e., greater than 100 pounds over one's ideal body weight), the risks of these procedures often outweigh the potential benefits for the growing segment of the population that is considered overweight. The additional weight carried around by these persons can still result in significant health complications, but does not justify more invasive treatment options. However, because conservative treatment with diet and exercise alone may be ineffective for reducing excess body weight, there is a need for treatment options that are less invasive and lower cost than the procedures discussed above.

It is known to create cavity wall plications through both laparoscopic and endoscopic procedures. Laparoscopic plication techniques can be complicated and complex, however, as one or more surgical entry ports must be employed to gain access to the surgical site. Furthermore, laparoscopically approaching the stomach often requires separating the surrounding omentum prior to plication formation. In endoscopic procedures, plication depth has traditionally suffered due to the size restrictions of the endoscopic lumen. For example, the rigid length and diameter of a surgical device are limited based on what sizes can be reliably and safely passed trans-orally into the stomach. Furthermore, access and visibility within the gastric and peritoneal cavities is progressively limited in an endoscopic procedure as the extent of the reduction increases because the volume of the gastric cavity is reduced.

In addition, prior art devices for forming endoluminal plications often utilize opposing jaws and a grasper element to draw tissue between the jaws. The prior art devices approach the cavity wall such that a longitudinal axis of the device is perpendicular to the cavity wall. The grasper element can then be advanced from the center of the open jaws, and used to draw tissue between the jaws to create the fold. However, the geometry of these devices limits the size of the plication that can be formed to approximately the length of the jaws, as the grasper can only draw the cavity wall tissue to the center of the jaws and no farther. Moreover, in order to secure a plication with a plurality of fasteners, prior art devices must release the tissue and be repositioned anew to apply each fastener.

With the foregoing in mind, it is desirable to have methods and devices for forming tissue folds, such as serosa-to-serosa tissue folds within the gastric lumen, that overcome any of the aforementioned problems.

SUMMARY

The present invention generally provides devices and methods for forming and securing plications of tissue. More particularly, the devices and methods of the present invention can be used to create and secure plications of gastric tissue on the anterior and posterior walls of a patient's gastric cavity to reduce the volume of the cavity.

In one aspect of the invention, a tissue acquisition and fixation system is provided that includes a staple applying assembly having first and second jaws. At least one of the jaws is movable such that the first and second jaws have an open position for receiving tissue and a closed position for engaging tissue. The first and second jaws can be effective to apply at least one staple to tissue engaged between the first and second jaws. The system also includes a tissue acquisition member positioned in a first plane that extends substantially parallel to a second plane extending through each of the first and second jaws. The tissue acquisition member can be effective to engage tissue and to position the engaged tissue between the first and second jaws.

In some embodiments, the tissue acquisition member can be movable between a first position in which the tissue acquisition member is disposed substantially between the first and second jaws, and a second position in which the tissue acquisition member is offset from the first and second jaws. The tissue acquisition member can be, for example, offset vertically above the first and second jaws.

In other embodiments, the staple applying assembly can include an elongate shaft having proximal and distal ends. The staple applying assembly can be coupled to the distal end of the elongate shaft to facilitate inserting the staple applying assembly into, for example, the stomach of a patient via the esophagus.

In still other embodiments, the first jaw of the staple applying assembly can be pivotally connected to the second jaw and can include an anvil portion configured to form a staple ejected from the second jaw.

In some embodiments, the second jaw of the staple applying assembly can include a stapler portion configured to retain a plurality of staples. The second jaw can also include a staple former configured to eject at least one of the plurality of staples from the stapler portion. In certain embodiments, the staple former can be configured to eject more than one staple simultaneously. In an exemplary embodiment, the second jaw can include a forming link slidably connected to the staple former and a firing link slidably and pivotally connected to the forming link. Further, the forming link and the firing link can both be pivotally coupled to the second jaw. These components can form a firing linkage effective to eject one or more staples from the stapler portion of the second jaw.

In order to adjust the relative position of the jaws, the system can, in some embodiments, include a positioning cable connected to the first jaw and configured to move the first jaw relative to the second jaw.

The tissue acquisition member, in some embodiments, can include a vacuum pod configured to draw tissue against the tissue acquisition member. Furthermore, the tissue acquisition member can include a hinge assembly configured to permit movement of the tissue acquisition member between a first position, in which the tissue acquisition member is disposed below a superior surface of the first and second jaws, and a second position, in which the tissue acquisition member is disposed above the superior surface of the first and second jaws. The hinge assembly can include, for example, a hinge member pivotally connected to the first jaw. In some embodiments, the hinge assembly can also include a positioning cable connected to the hinge assembly and configured to control movement of the tissue acquisition member between the first and second positions.

In another aspect of the invention, a tissue acquisition and fixation system is provided that includes an elongate shaft having proximal and distal ends, first and second jaws extending from the distal end of the elongate shaft, and a tissue acquisition member coupled to the first jaw. At least the first jaw can be movable between an open position in which the jaws are configured to receive tissue, and a closed position in which the jaws are effective to engage tissue. The jaws can be effective to apply at least one staple to tissue engaged between the jaws, and the tissue acquisition member can be effective to engage tissue and to position tissue between the first and second jaws. Further, movement of the first jaw between the open and closed position can be effective to cause corresponding movement of the tissue acquisition member.

In some embodiments, the tissue acquisition member can be movable in at least one of a vertical direction and a longitudinal direction relative to the first and second jaws. This freedom of relative movement can allow the tissue acquisition member to draw tissue through the first and second jaws.

In other embodiments, the tissue acquisition member can include a surface configured to engage tissue, and the surface can extend along a plane that is parallel to the first and second jaws. Further, the surface can include at least one vacuum port formed therein and configured to draw tissue against the surface.

In another aspect of the invention, a tissue acquisition and fixation system is provided that includes a stapling member having first and second jaws and a tissue acquirer coupled to at least one of the first and second jaws. The first and second jaws can be configured to move between an open position for receiving tissue and a closed position for engaging tissue. Further, the first and second jaws can be effective to apply at least one staple to tissue engaged between the first and second jaws. The tissue acquirer can be configured to engage tissue and to draw tissue up through the first and second jaws.

In some embodiments, the tissue acquirer can be coupled to at least one of the first and second jaws by a linkage configured to allow movement of the tissue acquirer with respect to the first and second jaws. The linkage can include a hinge mechanism and a connecting arm extending between the tissue acquirer and at least one of the first and second jaws. In some embodiments, the linkage can further include a second hinge mechanism and a second connecting arm extending between the tissue acquirer and at least one of the first and second jaws. The second hinge mechanism can be effective to maintain an orientation between the tissue acquirer and at least one of the first and second jaws throughout a range of motion of the linkage. The range of motion of the linkage can include moving the tissue acquirer any of vertically and longitudinally with respect to the first and second jaws.

In certain embodiments, the system can further include an indexing mechanism coupled to the tissue acquirer and the stapling member and configured to translate the tissue acquirer longitudinally relative to the stapling member. This indexing mechanism can, in some embodiments, be selected from the group consisting of a lead screw, a rack, and a pinion gear set.

In still other embodiments, the system can include a secondary acquirer coupled to the tissue acquirer and configured to engage tissue to maintain its position relative to the tissue acquirer. The secondary acquirer can, in some embodiments, be selected from the group consisting of a hook, a grasper, and a clamp pivotally connected to the tissue acquirer. The secondary acquirer can aid in holding tissue to the tissue acquirer, which can be configured to couple a vacuum source such that the tissue acquirer is effective to suction tissue against the tissue acquirer.

In another aspect of the invention, a tissue acquisition and fixation system includes an elongate shaft having proximal and distal ends, an end effector coupled to the distal end of the elongate shaft and having first and second jaws, and a tissue acquisition member coupled to the end effector by a linkage assembly. The first and second jaws can have an open position configured to receive tissue therebetween, and a closed position in which the first and second jaws are effective to engage tissue positioned therebetween. Further, at least a portion of at least one of the tissue acquisition member and the linkage assembly can be slidably movable along a longitudinal axis extending parallel to a longitudinal axis of at least one of the first and second jaws. The tissue acquisition member can also be vertically movable relative to the end effector such that a distance between a longitudinal axis of the tissue acquisition member and a longitudinal axis of at least one of the first and second jaws can be adjusted.

In some embodiments, the first and second jaws can be configured to drive at least one fastener through tissue positioned therebetween in the closed position. This can be done using, for example, the firing mechanisms discussed herein.

In other embodiments, the system can include a lead screw effective to slidably move at least a portion of the tissue acquisition member along a longitudinal axis extending substantially parallel to a longitudinal axis of at least one of the first and second jaws. The lead screw can be actuated by rotation of a cable extending through the elongate shaft. Further, at least a portion of the tissue acquisition member can be configured to move vertically relative to the end effector in response to longitudinal translation of the cable.

In still other embodiments, the end effector can include a lead screw effective to slidably move at least a portion of the tissue acquisition member and the linkage assembly along a longitudinal axis extending substantially parallel to a longitudinal axis of at least one of the first and second jaws.

In certain embodiments, the linkage assembly can include a gear rack and the end effector can include a pinion gear effective to slidably move the linkage assembly and tissue acquisition member along a longitudinal axis extending parallel to a longitudinal axis of at least one of the first and second jaws.

In some embodiments, the end effector can include a hinge pin and the linkage assembly can include a hinge base having a plurality of indexed grooves configured to seat the hinge pin. The system can further include a cable connected to the linkage assembly and configured to slidably move the hinge base relative to the hinge pin to seat the hinge pin in any one of the plurality of indexed grooves.

In another aspect of the invention, a tissue acquisition and fixation system is provided that includes an elongate shaft having a longitudinal axis, an end effector coupled to a distal end of the elongate shaft, and a tissue acquisition member coupled to the end effector. The end effector can have a fixed jaw and a movable jaw that pivots relative to the fixed jaw, and the tissue acquisition member can be limited to (1) movement along a longitudinal axis of the tissue acquisition member, and (2) movement perpendicular to a first plane extending through the first and second jaws.

In some embodiments, the system can include a lead screw coupled to the tissue acquisition member to allow at least a portion of the tissue acquisition member to translate along the longitudinal axis of the tissue acquisition member. The lead screw can be driven by rotation of a cable extending through the elongate shaft.

In other embodiments, the system can include a hinge assembly connecting the tissue acquisition member to the end effector. And, in some embodiments, the lead screw can be coupled to the hinge assembly to allow at least a portion of the hinge assembly and the tissue acquisition member to translate along a longitudinal axis of the tissue acquisition member.

In certain other embodiments, the system can instead include a rack gear coupled to the tissue acquisition member and a pinion gear coupled to the end effector to allow the tissue acquisition member to translate along a longitudinal axis of the tissue acquisition member.

In one aspect of the invention, a tissue acquisition and fixation system is provided including a stapling member having first and second jaws, a tissue acquisition member coupled to at least one of the first and second jaws, and a secondary tissue acquirer coupled to the tissue acquisition member. The first and second jaws can be configured to move between an open position for receiving tissue and a closed position for engaging tissue. The first and second jaws can also be effective to apply at least one staple to tissue engaged between the first and second jaws. The tissue acquisition member can be configured to engage tissue and to position the tissue between the first and second jaws. Finally, the secondary tissue acquirer can be configured to engage tissue and maintain the tissue in position relative to the tissue acquisition member.

In some embodiments, the secondary tissue acquirer can include at least one hook configured to grasp tissue drawn against the tissue acquisition member. The at least one hook can be coupled to a rotatable shaft extending parallel to a longitudinal axis of the tissue acquisition member such that rotation of the shaft is effective to engage the at least one hook with tissue drawn against the tissue acquisition member. The secondary tissue acquirer can also include an actuating cable coupled to the rotatable shaft such that rotation of the actuating cable is effective to rotate the shaft and thereby engage the at least one hook with the tissue.

In other embodiments, the tissue acquisition member can include a surface configured to engage tissue, and the at least one hook can be pivotally coupled to the tissue acquisition member such that the at least one hook pivots in a plane parallel to a plane defined by the surface. Pivoting of the at least one hook can be effected by translation of at least one suture or thin actuating cable attached to an end of each of the at least one hook. The at least one hook can include a spring attached to each of the at least one hook and configured to bias the at least one hook to a first position, such as a retracted position.

In certain embodiments, the secondary tissue acquirer can include at least one hinged grasper configured to engage tissue drawn against the tissue acquisition member. Further, the secondary tissue acquirer can include a cable coupled to the at least one grasper and configured to move the at least one grasper from an open position for receiving tissue to a closed position for engaging tissue. In some embodiments, the at least one grasper can be disposed on a distal end of the tissue acquisition member.

In still other embodiments, the secondary tissue acquirer can include at least one clamp configured to engage tissue drawn against the tissue acquisition member. In some embodiments, the secondary tissue acquirer includes at least two clamps that are pivotally coupled to opposing surfaces of the tissue acquisition member. The system can further include a wedge member slidably mounted to a top surface of the tissue acquisition member and configured to engage the at least two clamps such that the at least two clamps engage tissue drawn against the tissue acquisition member. A cable can be coupled to the wedge member and configured to slidably move the wedge member, thereby controlling the clamps.

In another aspect of the invention, a tissue acquisition and fixation system is provided that includes an elongate shaft having proximal and distal ends, a staple applying assembly having a proximal end coupled to the distal end of the elongate shaft and having first and second jaws, and a tissue acquisition member coupled to the staple applying assembly by a linkage mechanism. At least one of the jaws can be movable such that the first and second jaws have an open position for receiving tissue and a closed position for engaging tissue. The first and second jaws can be effective to apply at least one staple to tissue engaged between the first and second jaws. The tissue acquisition member can be effective to engage tissue and to position the engaged tissue between the first and second jaws. Further, the linkage mechanism can be configured to move the tissue acquisition member between a first position that is longitudinally offset and proximal to the staple applying assembly, and a second position that is longitudinally adjacent to the staple applying assembly.

In some embodiments, a distal end of the tissue acquisition member can be disposed proximal to the proximal end of the staple applying assembly in the first position. Further, the distal end of the tissue acquisition member can be disposed longitudinally adjacent to a distal end of the staple applying assembly in the second position.

In some embodiments, the first jaw can include an anvil for forming a staple, and the second jaw can include a staple cartridge configured to house two or more rows of staples. The staple applying assembly can further include at least one firing wedge in each staple row that is configured to selectively eject at least one staple from the staple row. Each of the at least one firing wedges can be selectively controllable by a user, and each of the at least one firing wedges can be controlled by translation of an actuating cable.

In some other embodiments, the tissue acquisition member can include a vacuum pod configured to couple to a vacuum source and apply a vacuum force to draw surrounding tissue against at least one surface of the tissue acquisition member. The tissue acquisition member can also include a secondary acquirer coupled to the tissue acquisition member and configured to engage tissue and maintain the tissue in position relative to the tissue acquisition member. The secondary acquirer can be selected from the group consisting of hooks, graspers, or clamps coupled to the tissue acquisition member.

In certain embodiments, at least a portion of the tissue acquisition member can be movable across a plane defined by a superior surface of the first and second jaws in the second position. Furthermore, in some other embodiments, the linkage mechanism can be further configured to move the tissue acquisition member to a third position in which the tissue acquisition member is vertically offset from the first and second jaws such that tissue engaged by the tissue acquisition member can be disposed between the first and second jaws.

The present invention also provides methods of using the devices disclosed herein to create one or more folds to, for example, reduce gastric cavity volume. In one aspect, a method of acquiring and fixating tissue is provided that includes inserting a surgical device having first and second jaws and a tissue acquisition member into a hollow body lumen, positioning the surgical device in a first position, drawing tissue through the jaws and against the tissue acquisition member, and actuating the surgical device. In the first position the first and second jaws can extend substantially parallel to a tissue surface and the tissue acquisition member can be positioned on an opposite side of the jaws from the tissue. Actuating the surgical device can include moving the tissue acquisition member away from the first and second jaws to draw the tissue through the first and second jaws, closing the first and second jaws, and driving at least one fastener through the tissue disposed between the first and second jaws.

In some embodiments, positioning the surgical device in the first position can further include positioning the surgical device such that the first and second jaws are substantially parallel to the tissue. In addition, the tissue acquisition member can be connected to any of the first and second jaws by a hinge assembly and positioning the surgical device in the second position can further include actuating a positioning cable connected to the hinge assembly to cause the tissue acquisition member to move relative to the first and second jaws.

In other embodiments, driving at least one fastener through the tissue can include actuating a firing linkage to drive a fastener out of the second jaw, through the tissue disposed between the first and second jaws, and against the first jaw. Furthermore, drawing tissue against the tissue acquisition member can include actuating a vacuum source to suction the tissue against the tissue acquisition member.

In another aspect of the invention, a method of acquiring and fixating tissue is provided that includes positioning a stapling member having first and second jaws adjacent to a tissue surface, engaging the tissue surface with a tissue acquirer, moving the tissue acquirer to draw tissue up through the first and second jaws, moving the first and second jaws to a closed position to engage the tissue therebetween, and applying at least a first staple. Positioning the stapling member can include ensuring that a longitudinal axis of at least one of the first and second jaws is parallel to the tissue surface. Applying at least a first staple can include firing a staple from at least one of the first and second jaws through the tissue disposed between the first and second jaws.

In some embodiments, the method can further include moving the first and second jaws to an open position, moving the tissue acquirer to reposition the tissue disposed between the first and second jaws, moving the first and second jaws to the closed position, and applying at least a second staple from at least one of the first and second jaws. In other embodiments, the method can include, prior to moving the tissue acquirer, actuating a secondary tissue acquirer that can be effective to engage tissue to retain the position of the tissue surface relative to the tissue acquirer.

In certain embodiments, moving the tissue acquirer to draw tissue up through the first and second jaws can include translating a positioning cable coupled to the tissue acquirer. Furthermore, the step of engaging the tissue surface can include activating a vacuum source to draw the tissue surface against the tissue acquirer.

In another aspect of the invention, a method of acquiring and fixating tissue includes positioning a surgical device having first and second jaws and a tissue acquisition member such that a longitudinal axis of the device is parallel to a tissue surface and the tissue acquisition member is on an opposite side of the first and second jaws from the tissue surface. The method can further include applying a vacuum force to draw the tissue surface through the jaws and against the tissue acquisition member, and moving the tissue acquisition member in a direction away from the tissue surface to further draw tissue through the first and second jaws to create a tissue fold.

In some embodiments, the tissue acquisition member can be connected to any of the first and second jaws by a hinge assembly, and positioning the surgical device can include actuating a positioning cable connected to the hinge assembly to cause the tissue acquisition member to move relative to the first and second jaws.

In other embodiments, the method can further include driving at least one fastener through the tissue fold disposed between the first and second jaws. In certain embodiments, driving at least one fastener through the tissue can include actuating a firing linkage to drive a fastener out of the second jaw, through the tissue fold disposed between the first and second jaws, and against the first jaw.

In some other embodiments, the method can include, prior to moving the tissue acquisition member, actuating a secondary tissue acquirer effective to engage tissue to retain the position of the tissue surface relative to the tissue acquisition member.

In still another aspect of the invention, a method of acquiring and fixating tissue using a plurality of fasteners includes positioning a surgical device having a stapling member and a tissue acquisition member adjacent to tissue such that a longitudinal axis of any of a first and a second jaw of the stapling member is parallel to a surface of tissue. The method further includes drawing tissue to the tissue acquisition member and moving the tissue acquisition member vertically away from the first and second jaws. The method also includes moving the first and second jaws of the stapling member to a closed position and driving at least one fastener through the tissue disposed between the first and second jaws. Further, the method includes moving the first and second jaws of the stapling member to the open position and translating the tissue acquisition member along a longitudinal axis of the tissue acquisition member that is substantially parallel to a longitudinal axis of at least one of the first and second jaws. Finally, the method also includes moving the first and second jaws of the stapling member to the closed position such that at least one fastener is driven through the tissue disposed between the first and second jaws.

In some embodiments, the step of translating the tissue acquisition member can include rotating a cable to drive a lead screw coupled to the tissue acquisition member. In certain other embodiments, the tissue acquisition member can include a rack gear connected to a pinion gear on the stapling member, and the step of translating the tissue acquisition member can include actuating a cable to drive the pinion gear. In still other embodiments, the method can further include moving the tissue acquisition member any of vertically away from the first and second jaws of the stapling member and longitudinally with respect to the first and second jaws to further draw tissue through the first and second jaws.

In one aspect of the invention, a method of acquiring and fixating tissue includes positioning a surgical device having a stapling member with first and second jaws and a tissue acquisition unit adjacent to a tissue surface such that a longitudinal axis of the stapling member is parallel to the tissue surface. The method can further include moving the stapling member to an open position such that the first and second jaws are separated, and moving the tissue acquisition member between the first and second jaws adjacent to the tissue surface. The method can also include drawing tissue against the tissue acquisition member, and engaging the tissue drawn against the tissue acquisition member with a secondary acquirer coupled to the tissue acquisition member. Still further, the method can include moving the tissue acquisition member to a position offset from the first and second jaws, moving the stapling member to a closed position such that the first and second jaws are drawn together, and applying a staple through the tissue disposed between the first and second jaws.

In some embodiments, the step of engaging the tissue drawn against the tissue acquisition member with the secondary acquirer can include engaging at least one hook coupled to the tissue acquisition member with the tissue. In other embodiments, this step can include engaging at least one grasper coupled to the tissue acquisition member with the tissue. Engaging the at least one grasper can include tensioning a cable connected to the at least one grasper via at least one linkage. In still other embodiments, the step of engaging the tissue drawn against the tissue acquisition member with a secondary acquirer can instead include engaging at least one clamp pivotally coupled to the tissue acquisition member with the tissue. Engaging the at least one clamp coupled to the tissue acquisition member can include slidably moving a wedge member along a track formed in the tissue acquisition member to engage the wedge member with the at least one clamp pivotally coupled to the tissue acquisition member.

In another aspect of the invention, a method of acquiring and fixating tissue is provided that includes pivoting a tissue acquisition member from a position longitudinally proximal to an end effector to a position longitudinally aligned with the end effector. The method can further include engaging tissue with the tissue acquisition member and moving the tissue acquisition member to draw tissue through first and second jaws on the end effector. Still further, the method can include moving the first and second jaws to a closed position to engage the tissue therebetween, and actuating the jaws to apply at least one staple through the tissue engaged therebetween.

In some embodiments, pivoting the tissue acquisition member can further include advancing at least a portion of the tissue acquisition member across a plane defined by a superior surface of the first and second jaws. Further, in some embodiments, moving the tissue acquisition member to draw tissue through the first and second jaws can further include moving the tissue acquisition member to a position vertically offset from the first and second jaws.

In certain embodiments, the method can also include, prior to moving the tissue acquisition member to draw the tissue through the first and second jaws, engaging a secondary tissue acquirer to secure the tissue to the tissue acquisition member. The secondary tissue acquirer can be selected from the group consisting of hooks, graspers, or clamps coupled to the tissue acquisition member.

In certain other embodiments, actuating the jaws can include selectively advancing at least one firing wedge configured to eject at least one staple from at least one of the first and second jaws. Selectively advancing the at least one firing wedge can include advancing the at least one firing wedge along a row of staples to drive at least one staple from the row. Selectively advancing the at least one firing wedge can also include translating at least one actuator cable coupled to the at least one firing wedge.

The present invention also provides general methods for locating and forming patterns of gastric folds in order to reduce the size of a gastric cavity. In one aspect of the invention, a method for gastric volume reduction is provided that includes advancing a tissue acquisition and fixation device endoscopically through an esophagus and into a stomach, and manipulating the tissue acquisition and fixation device within the stomach to form a first fold of tissue on an interior surface of an anterior wall of the stomach. In some embodiments, the first fold of tissue can consist of a plurality of multiple smaller folds of tissue. The method can further include manipulating the tissue acquisition and fixation device within the stomach to form a second fold of tissue on an interior surface of a posterior wall of the stomach, where the second fold is not attached to the first fold. In some embodiments, the second fold of tissue can consist of a plurality of multiple smaller folds of tissue.

In some embodiments, a first fastener can secure the first fold and a second fastener can secure the second fold. In fact, the method can further include inserting at least one fastener through the first fold of tissue, and inserting at least one fastener through the second fold of tissue. In other embodiments, the method can include securing the first fold with at least one row of fasteners and securing the second fold with at least one row of fasteners.

In certain embodiments, manipulating the tissue acquisition and fixation device can include positioning first and second jaws of the tissue acquisition and fixation device to extend substantially parallel to the anterior wall of the stomach, and acquiring tissue to form the first and second folds. Acquiring tissue can include activating a vacuum source to draw tissue to a tissue acquisition member of the tissue acquisition and fixation device, and manipulating the tissue acquisition member to draw the tissue through the first and second jaws of the tissue acquisition and fixation device. Acquiring tissue can further include engaging a secondary acquirer coupled to the tissue acquisition member to retain the tissue in position relative to the tissue acquisition member.

In certain other embodiments, manipulating the tissue acquisition and fixation device can include moving a tissue acquisition member from a first position to a second position. In the first position, a distance between a longitudinal axis of the tissue acquisition member and a longitudinal axis of the device can be minimized. In the second position, the tissue acquisition member can be offset from the device such that the distance between the longitudinal axes of the tissue acquisition member and the device can be greater than in the first position.

In another aspect of the invention, a method of gastric volume reduction is provided that includes advancing a tissue acquisition and fixation device endoscopically into a stomach of a patient, and applying a vacuum to a tissue acquisition member to engage tissue. The method further includes manipulating the device to cause the tissue acquisition member to position the engaged tissue between opposed jaws coupled to the tissue acquisition member, and actuating the device to move the opposed jaws to a closed position in which the opposed jaws engage the tissue. The method also includes actuating the device to cause the opposed jaws to deliver at least one fastener through the engaged tissue.

In some embodiments, the method can include, prior to applying a vacuum to the tissue acquisition member, positioning the tissue acquisition and fixation device such that a longitudinal axis of the device is substantially parallel to the tissue surface.

In certain other embodiments, manipulating the device to position the engaged tissue between opposed jaws further can include actuating a hinge linkage coupling the tissue acquisition member to at least one of the jaws in order to move the tissue acquisition member relative to at least one of the jaws. Actuating the hinge linkage can also include translating an actuating cable coupled to the hinge linkage.

In still other embodiments, the method can include moving the opposed jaws to an open position, any of translating and vertically moving the tissue acquisition member to re-position the tissue between the opposed jaws, and re-actuating the device to move the opposed jaws to a closed position and to cause the opposed jaws to deliver at least a second fastener through the tissue. Translating the tissue acquisition member can include rotating a lead screw to cause the tissue acquisition member to translate with respect to the opposed jaws. The method can, in some embodiments, also include repeating the steps of moving the tissue acquisition member and re-actuating the device to create a row of fasteners.

In some embodiments, the method can include, prior to manipulating the device, engaging a secondary acquirer coupled to the tissue acquisition member to retain the tissue in position relative to the tissue acquisition member.

In another aspect of the invention, a method for gastric volume reduction is provided that includes manipulating a surgical device to form at least one plication on at least one of an anterior and a posterior inner surface of the fundus region of a patient's stomach. The method further includes, after forming the at least one plication, advancing the surgical device distally from the fundus toward the antrum region of the stomach and manipulating the surgical device to form a plurality of plications on at least one of an anterior and a posterior inner surface of the stomach.

In some embodiments, an end effector of the surgical device is articulated in a retroflexed position when the at least one plication is formed in the fundus. In other embodiments, advancing the surgical device distally from the fundus can include un-articulating the end effector to return the end effector to a position in which the end effector is substantially aligned with at least a distal portion of an insertion shaft having the end effector mated thereto. In some other embodiments, forming a plurality of plications in the stomach can also include articulating the end effector of the surgical device to access portions of the stomach. In still other embodiments, the plurality of plications can be formed in a distal-to-proximal direction.

BRIEF DESCRIPTION OF THE DRAWINGS

The aspects and embodiments of the invention described above will be more fully understood from the following detailed description taken in conjunction with the accompanying drawings, in which:

FIG. 46A illustrates an exemplary method of positioning of a staple applying assembly within a gastric cavity;

FIG. 46B illustrates articulation of the staple applying assembly to access the upper region of the gastric cavity;

FIG. 46C illustrates an exemplary plication created in the upper region of the gastric cavity;

FIG. 47A illustrates an exemplary method of forming multiple plications by fanning out from the position of the plication shown in FIG. 46C;

FIG. 47B illustrates the fan-shaped articulation of the staple applying assembly to create multiple plications;

FIG. 47C illustrates an embodiment of a fan-shaped pattern of plications;

DETAILED DESCRIPTION

Figure 1:
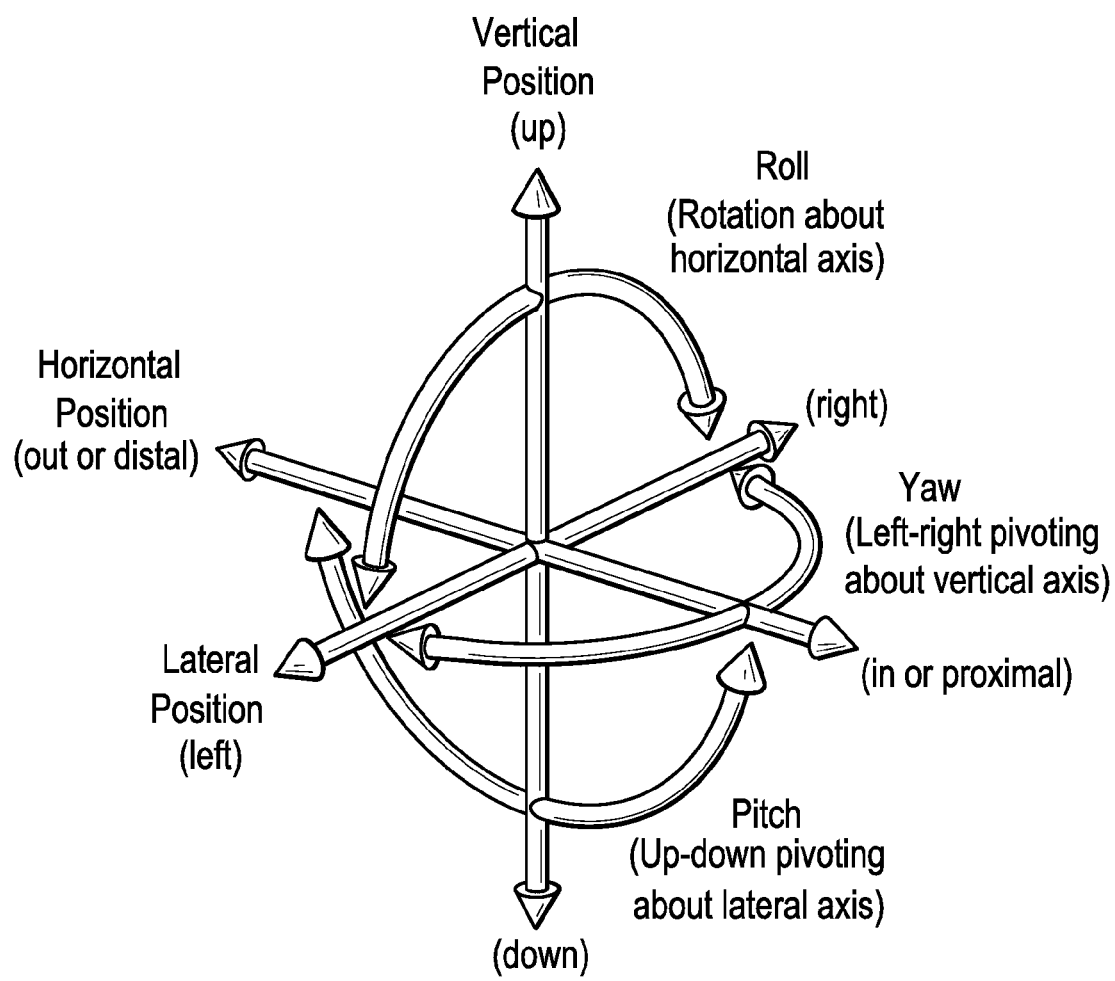
FIG. 1 is a diagram of the six degrees of freedom of a rigid body.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for apposing, forming, and securing tissue plications. These generally involve the creation of tissue plications for the reduction of cavity capacity, but may include the closure or repair of intentional (gastrotomy, colostomy, or enterotomy closure from Natural Orifice Translumenal Endoscopic Surgery (NOTES™), etc.) or unintentional (fistula, gastrointestinal leaks, etc.) tissue defects as well as the creation valves or restrictions to alter (e.g., enhance or impede) the flow of substances (e.g., Nissen fundoplication). In general, devices are provided having an end effector with a set of stapling jaws and a tissue acquisition member. The end effector can be coupled to the distal end of an elongate shaft or other surgical instrument that can be configured, for example, to be inserted into a patient's stomach through the esophagus. The surgical device can also include an articulating section to allow the end effector to articulate and thereby access a range of locations on, for example, both the anterior and posterior inner walls of the stomach. In use, the end effector can be positioned such that the stapling jaws are parallel to an inner tissue surface of the stomach. The tissue acquisition member can be disposed on an opposite side of the jaws from the tissue surface, and can be used to draw tissue through the jaws in a direction away from the tissue surface. This movement of the tissue acquisition member can create a tissue plication, or fold, disposed between the stapling jaws. The plication can be secured by driving a fastener out of the jaws and through the tissue.

By forming and fastening one or more of these plications, the volume or capacity of a cavity, such as the gastric cavity, can be reduced without the need for more invasive surgical procedures. The devices and methods of the present invention can be used to treat a wide variety of complications that develop as a result of metabolic disease. One common example of such a complication is obesity. However, non-obese individuals suffering from other metabolic disease complications, such as patients with low-Body Mass Index (BMI) type 2 diabetes, can also be treated using the teachings of the present invention.

As noted above, the devices disclosed herein can be at least partially positioned inside a patient's body cavity through an orifice for minimally invasive surgical procedures. Typically, the devices are inserted through a patient's mouth and extended down their esophagus into the stomach. However, it will be appreciated by those skilled in the art that any of the surgical device components disclosed herein can also be adapted for use in other surgical procedures, whether minimally invasive or open.

The various components of the devices disclosed herein can be formed from any of a variety of materials known in the art and suitable for use in surgical devices. For example, the various components can be formed from metal (e.g., stainless steel, titanium, or other biocompatible metals), plastic (e.g., polyetheretherketone (PEEK), or other biocompatible polymers), and/or combinations thereof.

Terminology

There are a number of ways in which to describe the position and orientation of an object in space. For example, the position and orientation of an object can be characterized in terms of the degrees of freedom of the object. The degrees of freedom of an object are the set of independent variables that completely identify the position and orientation of the object. As shown in FIG. 1, the six degrees of freedom of a rigid body with respect to a particular Cartesian reference frame can be represented by three translational (position) variables (e.g., horizontal position, vertical position, and lateral position) and by three rotational (orientation) variables (e.g., roll, pitch, and yaw).

For convenience of description, horizontal position is sometimes described herein as translational movement in an "in" direction or an "out" direction, or as longitudinal movement in a proximal or distal direction (e.g., where a longitudinal axis of a device is co-linear, or parallel to, the axis of horizontal position shown in FIG. 1). Vertical position is sometimes described as translational movement in an "up" direction or a "down" direction, or as vertical movement that is perpendicular to the longitudinal movement described above. Lateral movement is sometimes described as translational movement in a "left" direction or a "right" direction, or as lateral movement that is perpendicular to both the longitudinal and vertical movements discussed above. Likewise, roll is sometimes described herein as rotation about a longitudinal axis, pitch is sometimes described as pivoting in the up direction or the down direction, and yaw is sometimes described as pivoting in the left direction or the right direction. An exemplary mapping of the in, out, up, down, left, and right directions to a surgical device is shown in FIG. 1. This terminology and the illustrated mapping are not intended to limit the invention, and a person having ordinary skill in the art will appreciate that these directional terms can be mapped to the device, or any component thereof, in any of a variety of ways.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention.

Stapling Jaws

One embodiment of a device of the present invention is a stapling member or staple applying assembly configured to approach a cavity wall such that a longitudinal axis of the device is parallel to the surface of the cavity wall. This is in contrast to the prior art devices described above, in which a device having a set of jaws is configured to approach a cavity wall such that a longitudinal axis of the device is perpendicular to the surface of the cavity wall.

Figure 2:
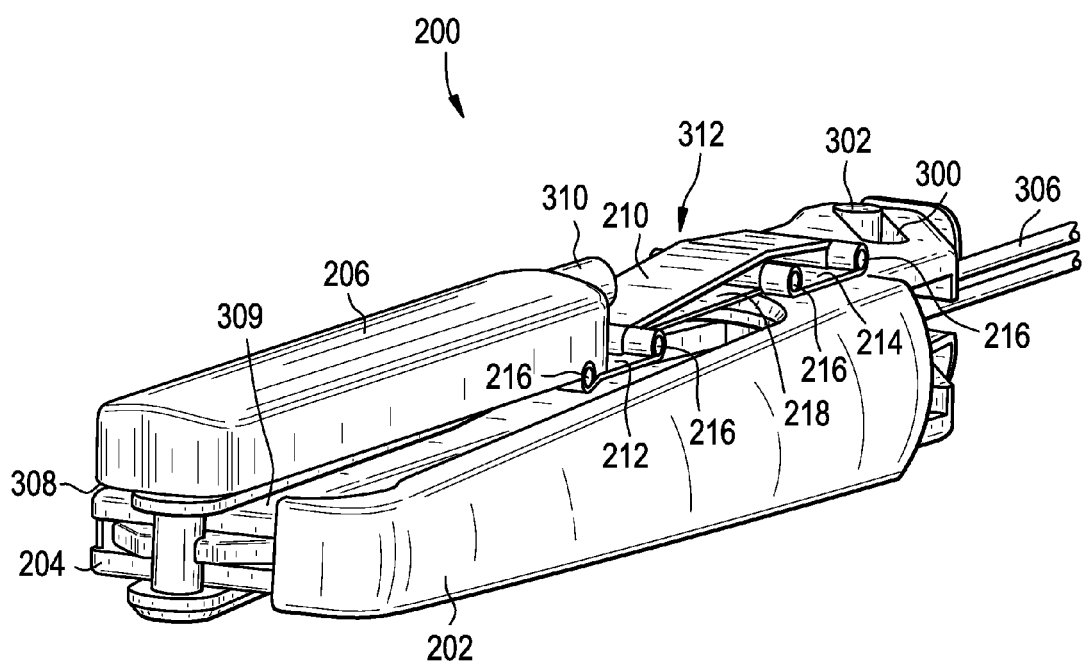
FIG. 2 is a front perspective view of one embodiment of a staple applying assembly.

FIGS. 2-5 illustrate such a device in several configurations. FIG. 2 illustrates a staple applying assembly 200 in a collapsed or closed configuration that can be used to minimize the cross-sectional area of the assembly for introduction into, for example, a patient's gastric cavity through the esophagus. The assembly 200 is a generally elongate device (e.g., to facilitate entry into a narrow lumen such as the esophagus) that includes a first jaw 202, a second jaw 204, and a tissue acquisition member 206. In some embodiments, the length of the first jaw 202 and the second jaw 204, and therefore the staple applying assembly 200 as a whole, is in the range of about 25 millimeters to about 80 millimeters in length and fits within a circular diameter of about 14 mm to 20 mm to facilitate endoscopic entry of the device into a patient's gastric cavity. Although not shown in the attached figures, the exterior components of assembly 200 may be covered, coated, or contain additional features or geometry that minimize the risk of unintentional tissue damage during insertion, operation, or removal. Exemplary features include blunt surfaces, tapered tips, fillets, chamfers, elastomeric coatings/ coverings, or any other similar feature known to one skilled in the art.

Figure 3:
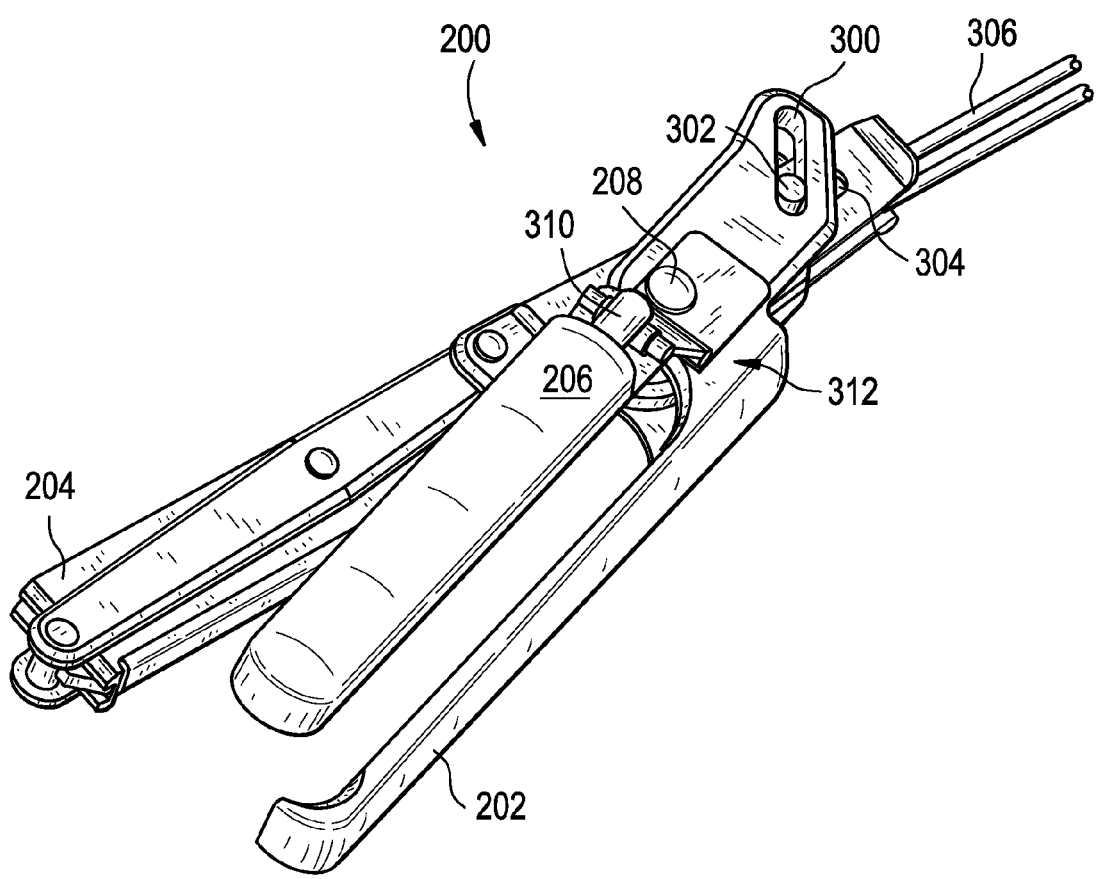
FIG. 3 is a top perspective view of the staple applying assembly of FIG. 2.
Figure 4:
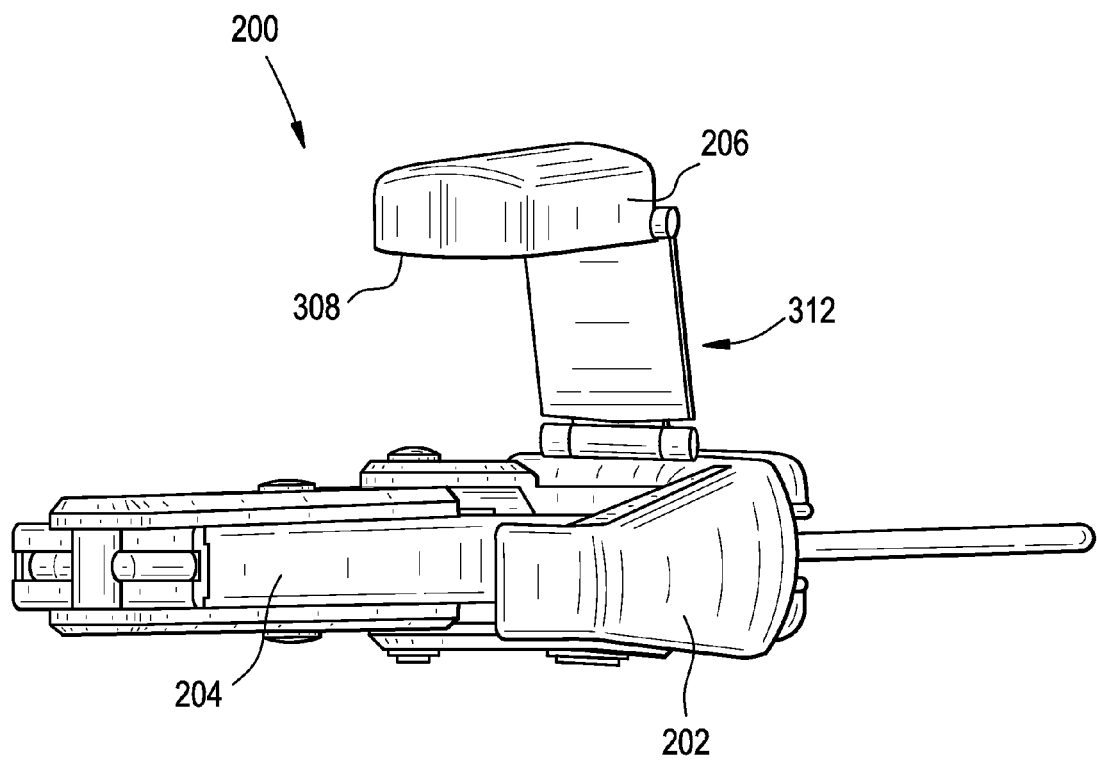
FIG. 4 is a front perspective view of the staple applying assembly of FIG. 2.
Figure 5:
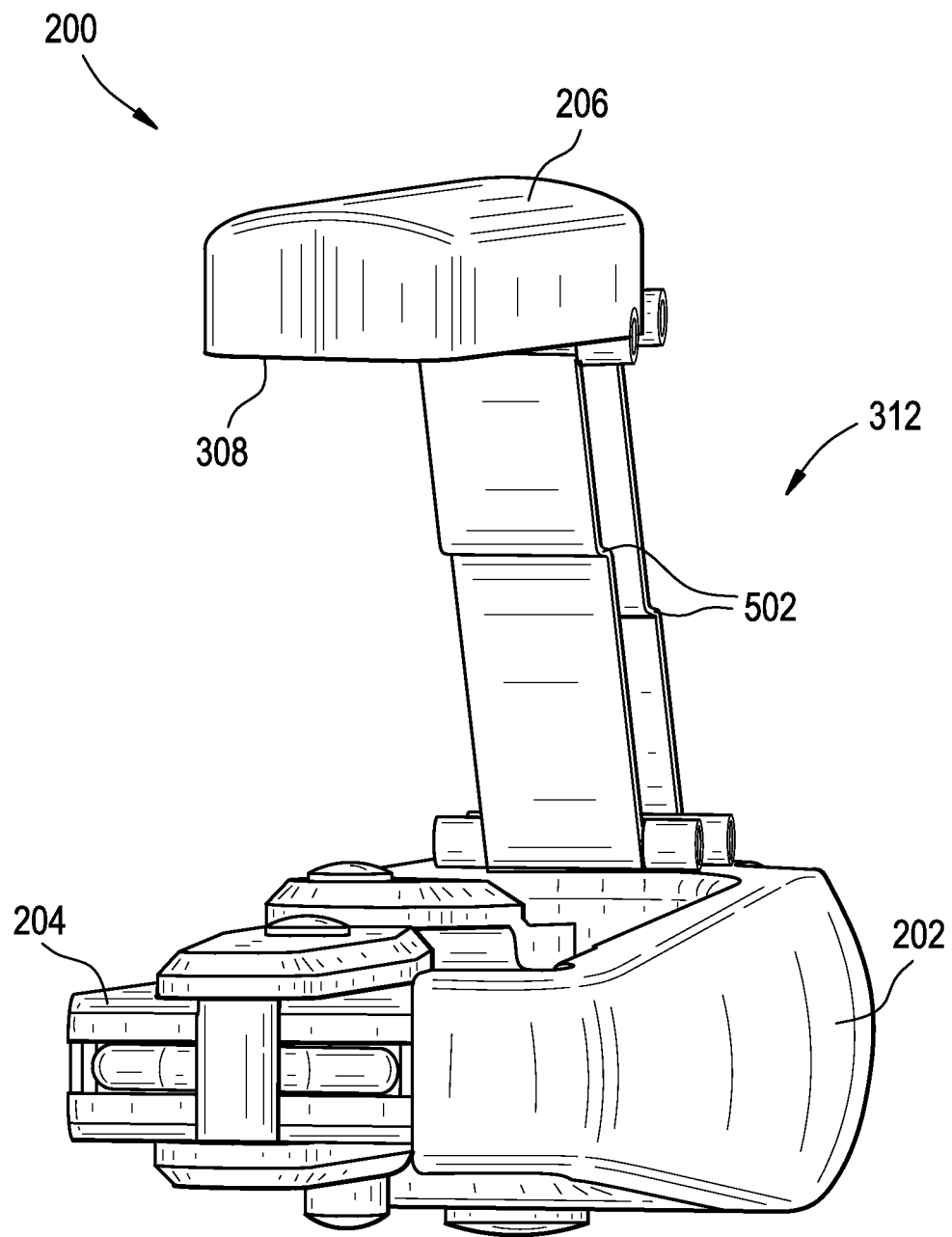
FIG. 5 is an alternative front perspective view of the staple applying assembly of FIG. 2.

The first jaw 202 and the second jaw 204 can work in conjunction to apply at least one fastener through tissue engaged between the first jaw 202 and the second jaw 204. In order to facilitate the engagement of tissue between the jaws, at least one of the first jaw 202 and the second jaw 204 can be movable to allow the assembly 200 to move between an open position for receiving tissue and a closed position for engaging tissue. FIGS. 2 and 5 illustrate the first jaw 202 and the second jaw 204 in a closed position, while FIGS. 3 and 4 illustrate the first jaw 202 and the second jaw 204 in an open position. In the particular embodiment illustrated in FIGS. 2-5, the first jaw 202 is pivotally connected to the second jaw 204 by pin 208.

Referring to FIG. 3, the first jaw 202 can also include a slot 300 formed therein and aligned at an angle to a longitudinal axis of the first jaw 202. The slot 300 can receive a sliding pin 302 to control movement of the first jaw 202 between the open and closed positions. In particular, the pin 302 can be seated in a slot 304 formed in the second jaw 204 that is in alignment with a longitudinal axis of the second jaw 204. The pin 302 can also be connected to a positioning cable 306 or other actuation mechanism known in the art. As the pin 302 is moved along the path of the slot 304 in response to actuation by the positioning cable 306 (e.g., if the positioning cable 306 is pulled in a proximal direction), the first jaw 202 will pivot around the pin 208 as the pin 302 moves along the slot 300 of the first jaw 202. As illustrated in FIGS. 2-5, when the pin 302 is in its distal-most position in the slots 300 and 304, the first jaw 202 will move to the open position for receiving tissue shown in FIGS. 3 and 4. Conversely, when the pin 302 is retracted to its proximal-most position in the slots 300 and 304, the first jaw 202 will move to the closed position for engaging tissue that is shown in FIGS. 2 and 5. In the embodiments disclosed herein, actuating the positioning cable 306 is sufficient to move the first jaw 202 to the open position for receiving tissue shown in FIGS. 3 and 4. It should be noted, however, that in some embodiments a biasing member, such as a spring, can be configured to assist transition between an open and a closed position.

In the embodiments disclosed herein, only the first jaw 202 moves to transition between the open and closed positions. It should be noted, however, that in some embodiments both the first and second jaws can be configured to move (e.g., similar to the operation of scissors) when transitioning between an open position and a closed position.

In some embodiments, the distal ends of the first jaw 202 and the second jaw 204 are configured to separate 10 mm or less when in the open position. Limiting the separation of the first jaw 202 and the second jaw 204 in the open position can prevent undesired surrounding tissue from being unintentionally drawn between the jaws by the tissue acquisition member. It can be undesirable for some surrounding tissue, such as small bowel, omentum, adjacent organs such as the liver, and blood vessels, to be included in a gastric plication, as it can cause complications such as gastric obstruction, tissue necrosis, and undetected bleeding.

Figure 6:
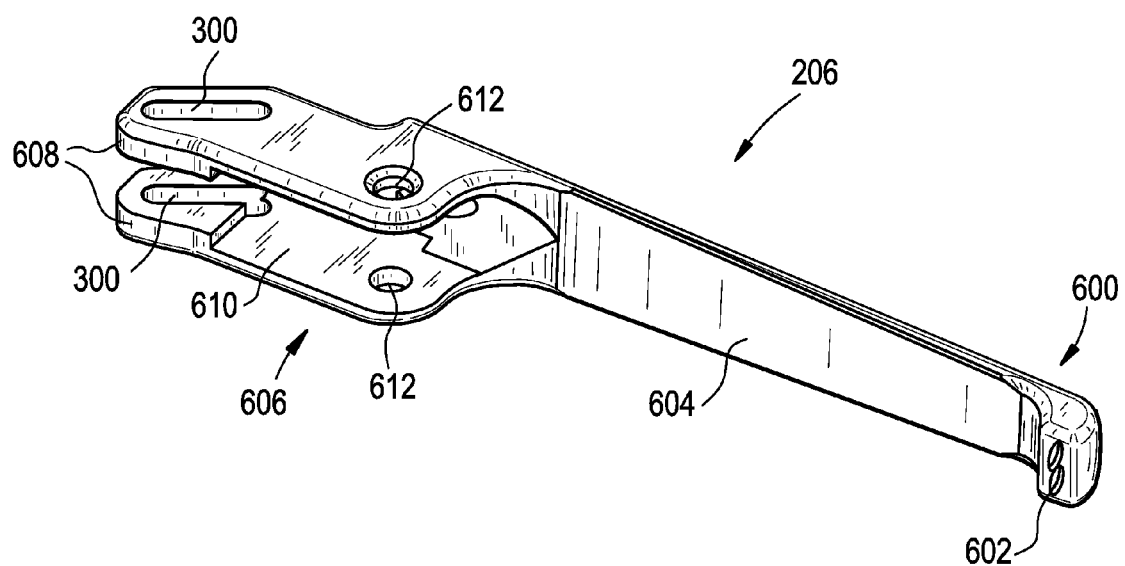
FIG. 6 is a front perspective view of a first jaw of the staple applying assembly of FIG. 2.

The first jaw 202, which is illustrated in isolation in FIG. 6, can also include an anvil portion 600 configured to form a staple or other fastener ejected from the second jaw 204. As shown in the figure, the first jaw 202 features an anvil portion 600 having only one staple-forming receptacle 602. However, in some embodiments, and as discussed in detail below, the staple applying assembly 200 may be configured to apply a plurality of staples sequentially or simultaneously. In these embodiments, the first jaw 202 may include a plurality of staple-forming receptacles formed along the elongate inner surface 604 of the first jaw 202.

The proximal end of the first jaw 202 can include a mating portion 606 configured to movably connect the first jaw 202 to the second jaw 204. The mating portion can include two symmetrical sidewalls 608 configured to receive the second jaw 204 in a recess 610 defined by the sidewalls 608. Furthermore, each of the sidewalls 608 can include symmetrical slots 300 for receiving the pin 302, as well as through-holes 612 for receiving the pivot pin 208, as discussed above. It should be noted that, in some embodiments, the first jaw 202 can include only a single sidewall 608, rather than two symmetrical sidewalls.

Figure 7:
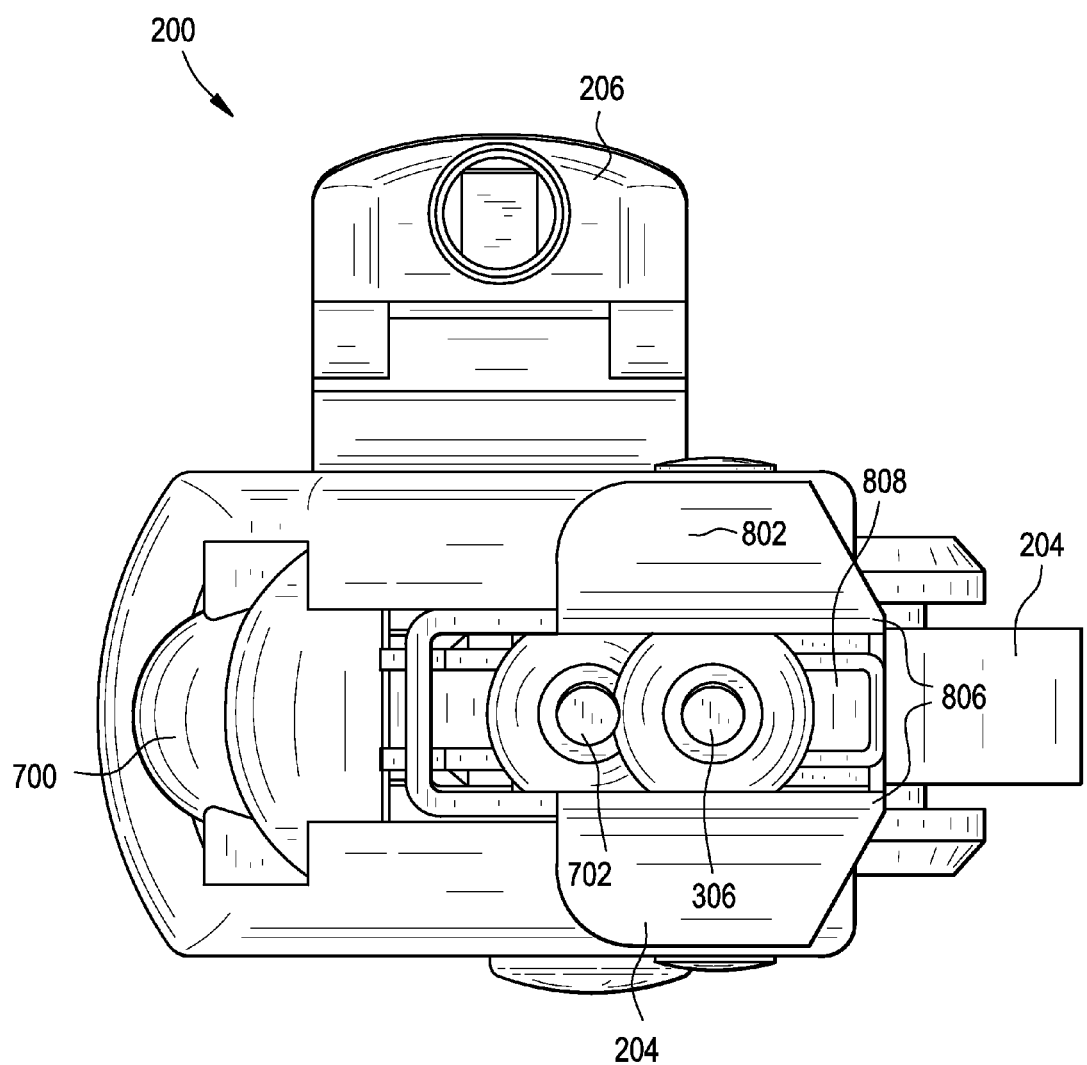
FIG. 7 is a rear view of the staple applying assembly of FIG. 2.

FIG. 7 illustrates a rear view of the staple applying assembly 200 and shows an additional feature of the first jaw 202. In particular, the first jaw 202 can include a fillet 700 in the mating portion 606 to allow an endoscopic viewing scope to directly view any tissue disposed between the first jaw 202 and the second jaw 204. This can be used to, for example, examine the depth of a plication being formed or the alignment of a plurality of staples or other fasteners being used to secure the plication.

Figure 8:
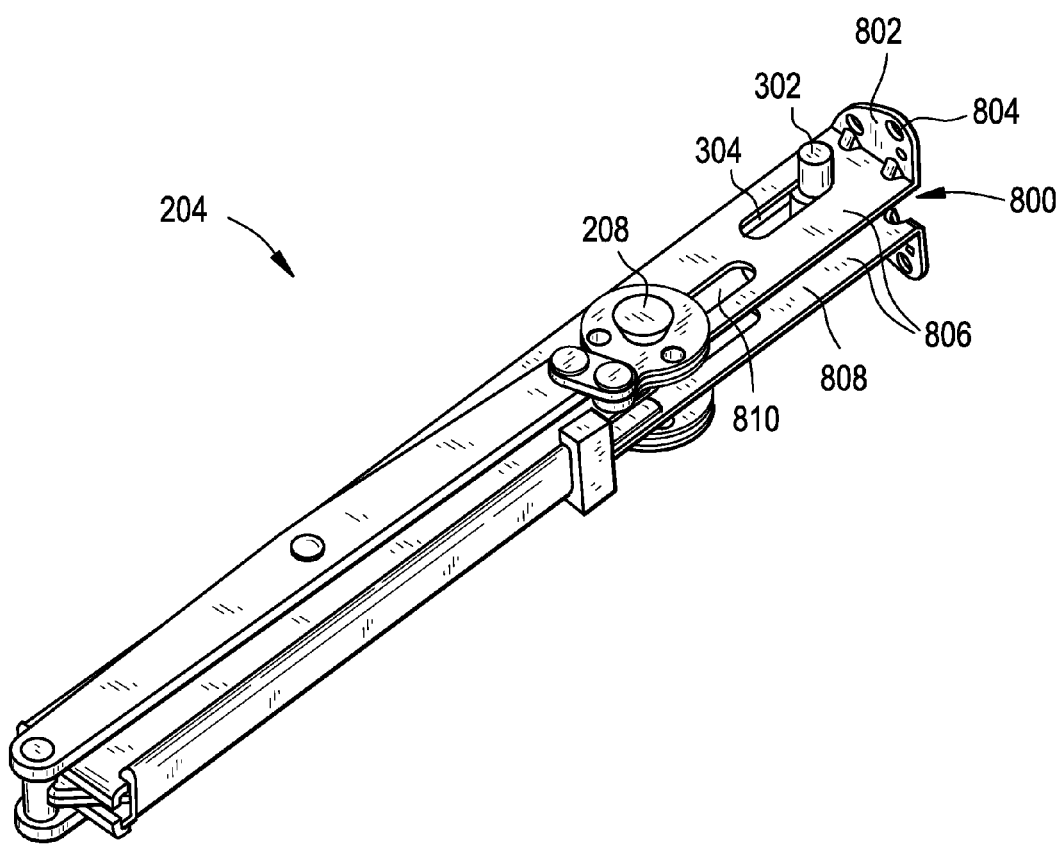
FIG. 8 is a front perspective view of one embodiment of a second jaw of a staple applying assembly.

An embodiment of the second jaw 204 is shown in isolation in FIG. 8. The second jaw 204 can be a generally elongate member having an attachment portion 800 that can be used to couple the second jaw 204, and therefore the entire staple applying assembly 200, to a surgical device, as discussed in more detail below. The attachment portion 800 can include any number of configurations known in the art and, in some embodiments, can comprise one or more tabs 802 having through-holes 804 configured to receive bolts or other fasteners for use in securing the attachment portion 800 to a surgical device.

The second jaw 204 can be formed from two symmetric outer walls 806 arranged parallel to each other and offset by a distance to create a recess 808 between the outer walls 806.

The outer walls 806 can be two separate walls held in position by, for example, elements such as a pin 208 or a connecting element coupled to the attachment portion 800. Alternatively, the outer walls 806 can be formed from a single wall featuring a bend at the distal end, thus forming an elongated "U" shape. The recess 808 formed between the outer walls 806 can accommodate passage of one or more actuating cables, such as a positioning cable 306. Referring to the rear view of FIG. 7, two actuating cables are shown in the recess 808 between the outer walls 806 of the second jaw 204. The positioning cable 306 can be used, for example, to control the opening and closing of the first jaw 202 relative to the second jaw 204, as discussed above. The second actuating cable 702 can be used, for example, to control the firing mechanism for delivering staples to tissue disposed between the jaws, as discussed in more detail below.

Figure 9:
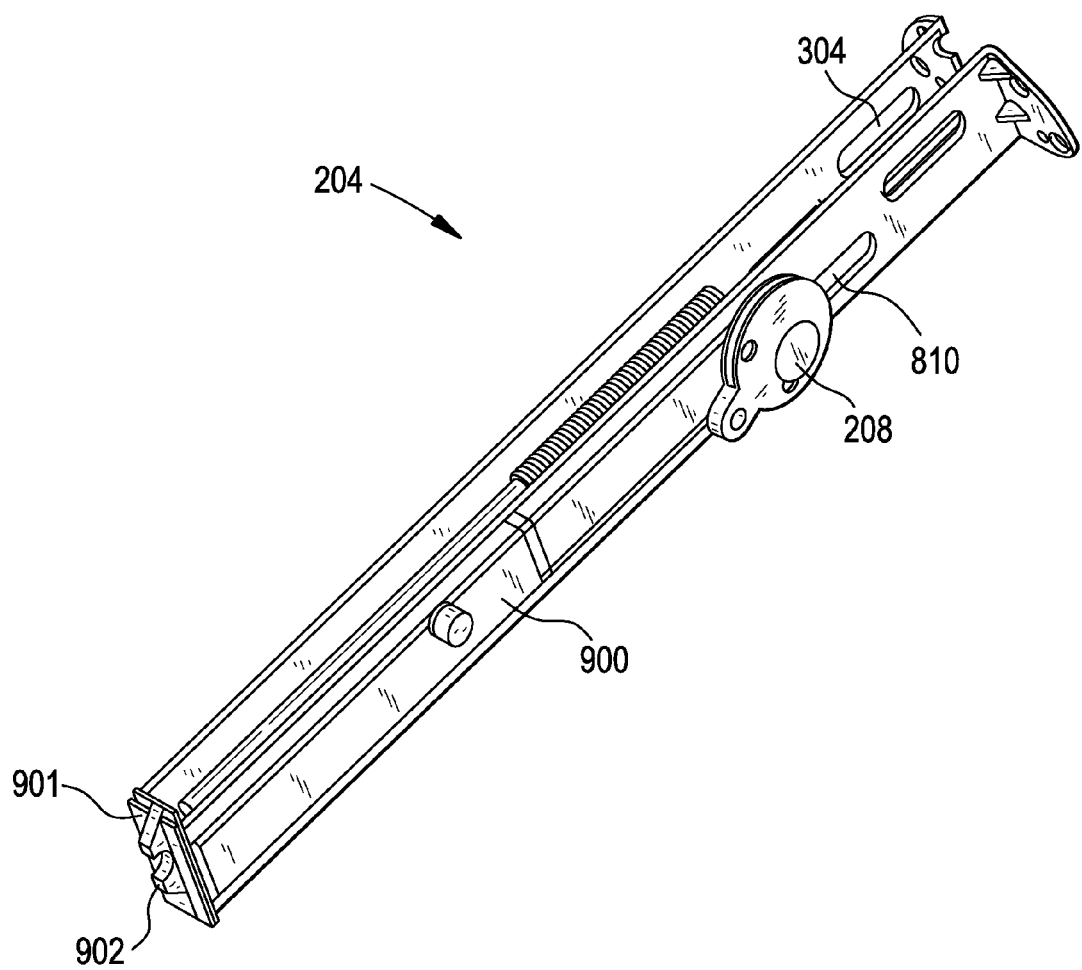
FIG. 9 is an alternative transparent front perspective view of the second jaw of FIG. 8.
Figure 10:
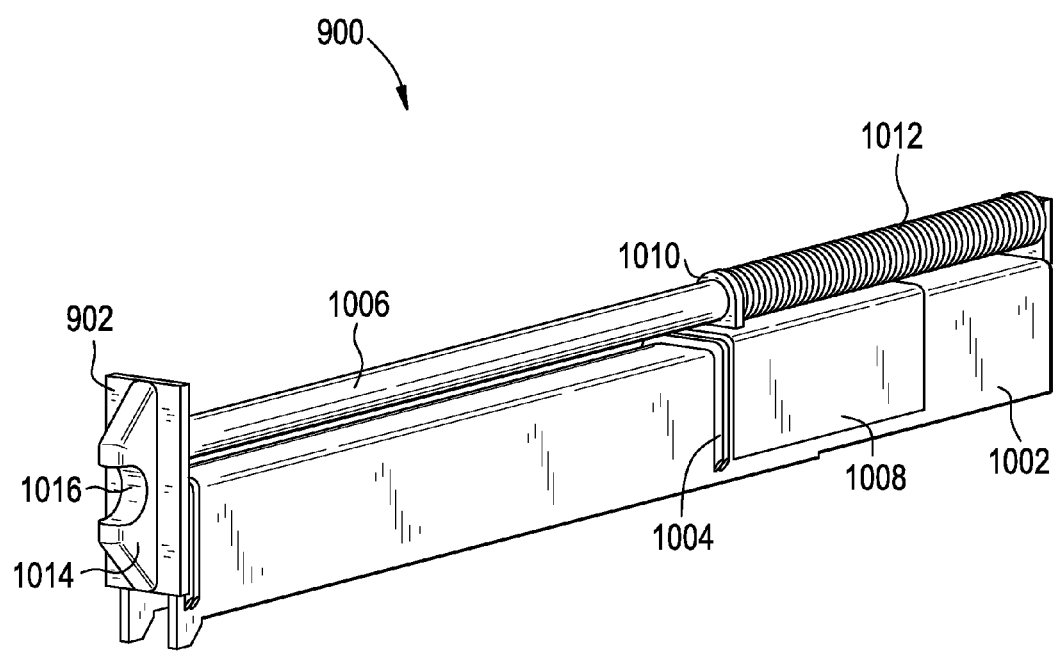
FIG. 10 is a front perspective view of the stapler portion and staple former of the second jaw of FIG. 8.

The recess 808 of the second jaw 204 can also house a stapler portion 900, shown in the transparent view of the second jaw 204 in FIG. 9. The stapler portion 900 can be configured to retain a plurality of staples and urge them towards a staple former 902 that is configured to eject a staple or other fastener from the second jaw 204 toward the anvil portion 600 of the first jaw 202. FIG. 10 illustrates the stapler portion 900 and staple former 902 in isolation.

The stapler portion 900 includes an inverted "U" shaped housing 1002 that can be complementary in shape to the staple 1004 or other fastener being used. One or more staples 1004 can be loaded into the stapler portion 900 by sliding the staples 1004 over the housing 1002, similar to loading a common office desktop stapler. In some embodiments, the stapler can hold up to 100 staples, but the total capacity can depend on the length of the stapler portion 900, the diameter of the staple applying assembly 200 (and the subsequent size constraints that imposes on all components of the assembly), etc. In addition, a number of different staple types can be used with the devices of the present invention. The stapler portion 900 and anvil portion 600 can be configured to accommodate various staples 1004, including staples that form into a box shape, a B-shape, or staples that form into three-dimensional or out-of-plane shapes.

The housing 1002 can feature a guide shaft 1006 connected thereto at a proximal end and a distal end of the housing 1002 and running parallel to the housing. In the embodiment illustrated in FIG. 10, the guide shaft 1006 is located above the housing 1002, but could also be located to either side or below the housing.

The stapler portion 900 also includes a staple pusher 1008 that is connected to the guide shaft 1006. The staple pusher 1008 can also have an inverted "U" shape similar in dimension to the staples 1004. The illustrated staple pusher 1008 sits on top of the housing 1002 proximal to the staples 1004 and is connected to the guide shaft 1006 by a receiving eye 1010 protruding above the upper surface of the staple pusher 1008. The staple pusher 1008 is configured to push the plurality of staples 1004 toward the distal end of the stapler portion 900. This can be accomplished by a coil spring 1012, or other urging member, that is disposed over the guide shaft 1006 such that it acts on the housing 1002 and the staple pusher 1008, as illustrated in FIG. 10.

Figure 12A:
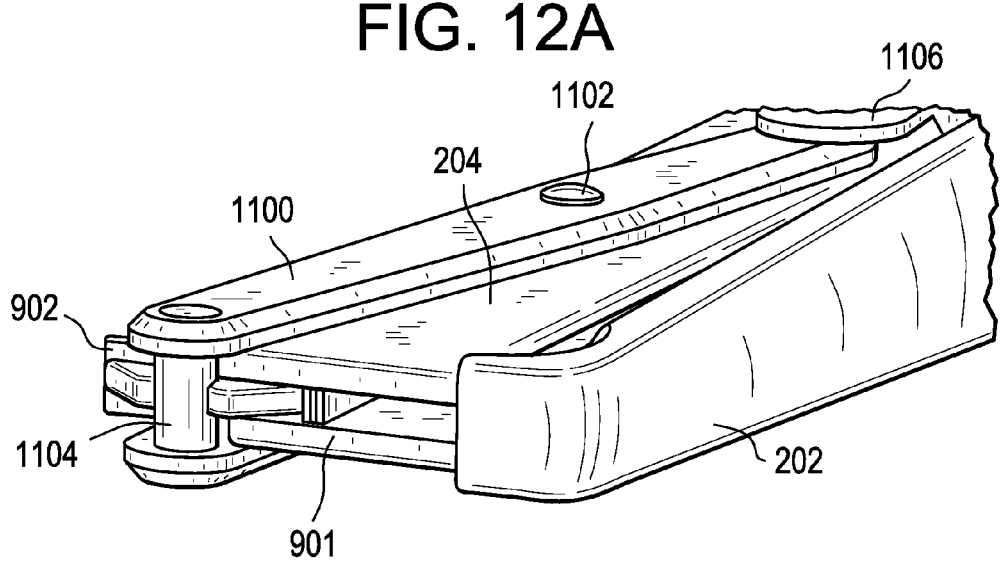
FIG. 12A is a front perspective view of the staple firing mechanism of FIG. 11A shown in the first position.
Figure 12B:
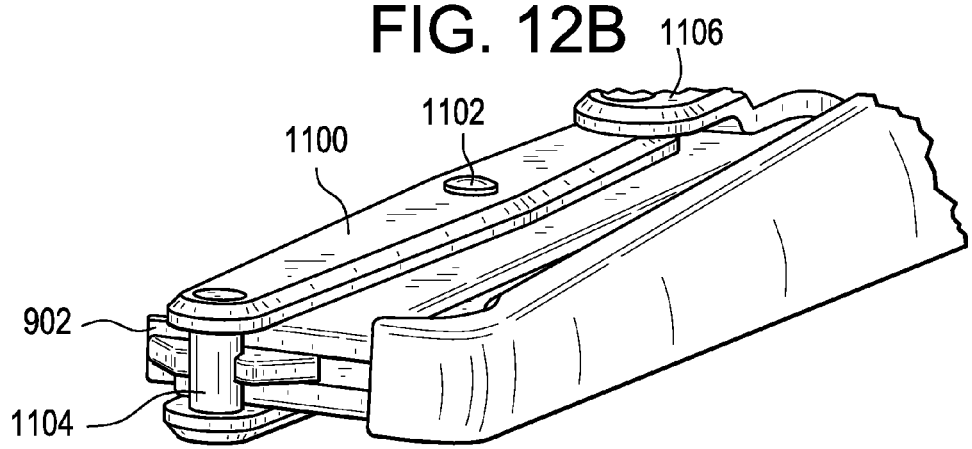
FIG. 12B is a front perspective view of the staple firing mechanism of FIG. 12A shown in the second position.
Figure 12C:
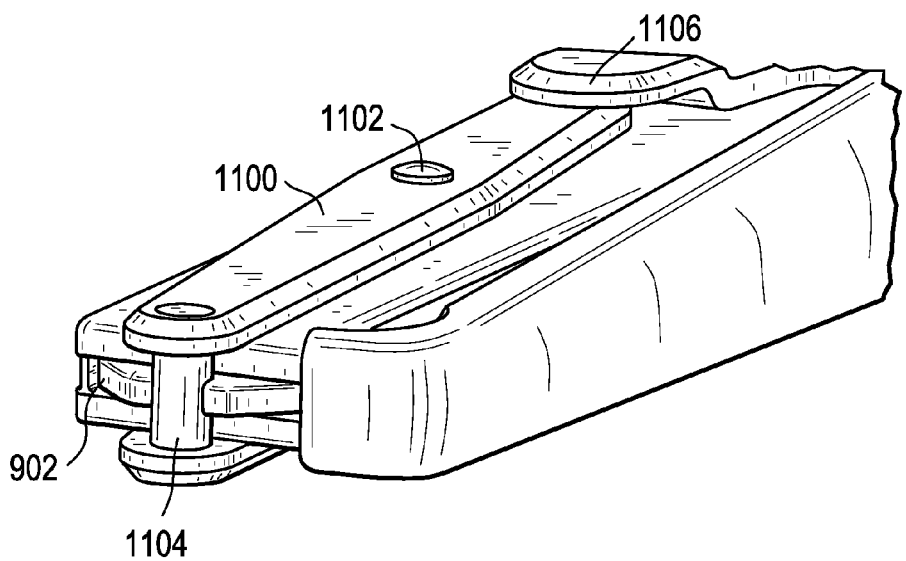
FIG. 12C is a front perspective view of the staple firing mechanism of FIG. 12A shown in the third position.

At the distal end of the stapler portion 900, the staple former 902 is disposed in a slot 901 created by the stapler portion 900 and the outer walls 806 of the second jaw 204 (see FIGS. 12A-12C for more detail of the outer walls 806 retaining the staple former 902). In other embodiments, either the outer walls 806 of the second jaw 204 or the stapler portion 900 can include a fully enclosed slot in which the staple former 902 can be disposed. The staple former 902 can have any shape suitable to translate along an axis offset from a longitudinal axis of the second jaw 204 to push a staple or other fastener from the stapler portion 900 of the second jaw 204 into the anvil portion 600 of the first jaw 202. In the illustrated embodiment, the staple former 902 is a thin, rectangular element positioned such that a longitudinal axis thereof is perpendicular to a longitudinal axis of the second jaw 204. The staple former 902 can also include a protrusion 1014 having a fillet 1016 that is configured to receive a portion of the fastener delivery mechanism, as discussed in detail below.

Fastener Delivery Mechanism

Figure 11A:
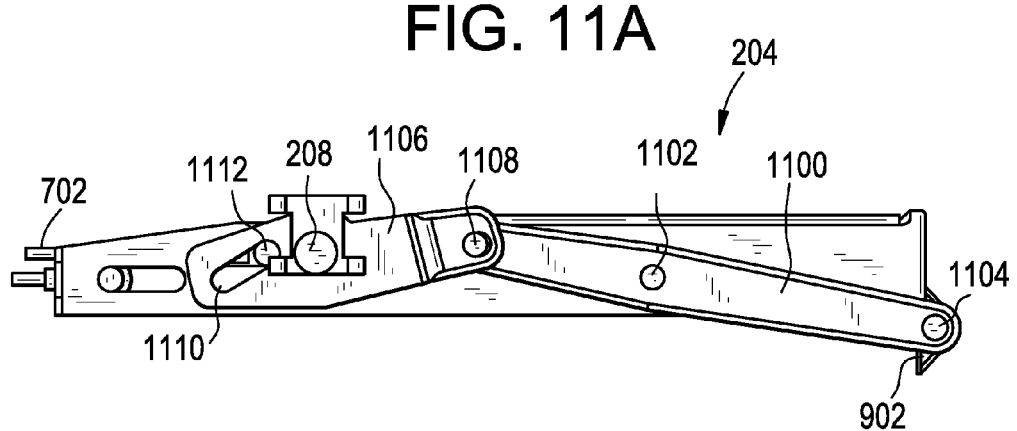
FIG. 11A is a top view of a staple firing mechanism disposed on an outer surface of the second jaw of FIG. 2, shown in a first position.
Figure 11B:
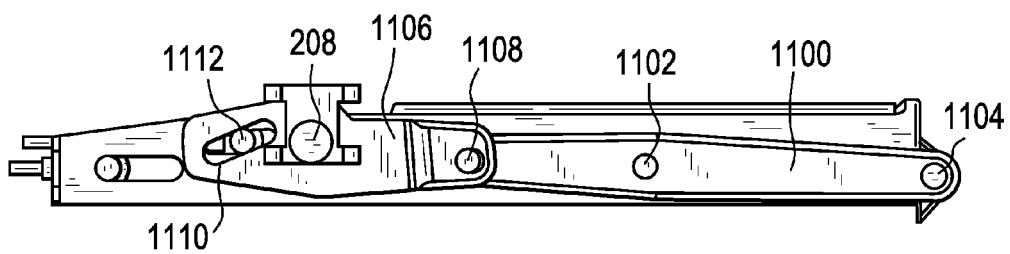
FIG. 11B is a top view of the staple firing mechanism of FIG. 11A shown in a second position.
Figure 11C:
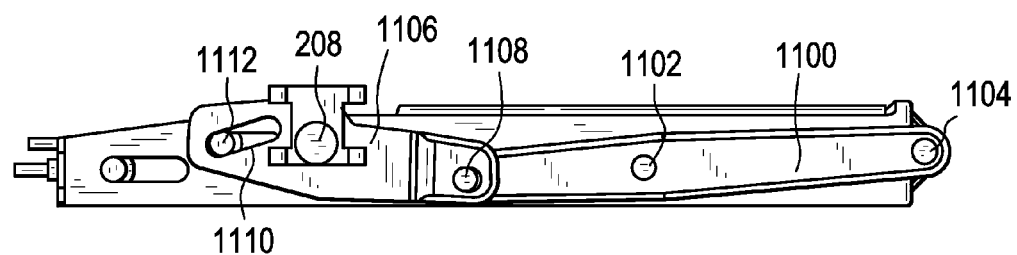
FIG. 11C is a top view of the staple firing mechanism of FIG. 11A shown in a third position.

There are a variety of fastener delivery mechanisms that can be used to actuate the staple former 902 to eject a staple 1004 from the second jaw 204 into the first jaw 202. FIGS. 11A-11C illustrate one embodiment of a staple-firing linkage disposed on an outer surface of the outer walls 806 of the second jaw 204.

The staple-firing linkage includes a forming link 1100 that is pivotally connected to the second jaw 204 via a pin 1102. At its distal end, the forming link 1100 includes a second pin 1104 that is seated in the fillet 1016 of the protrusion 1014 on the staple former 902. As stated above and shown in FIG. 11A, the staple former 902 is able to slide perpendicular to a longitudinal axis of the second jaw 204 within the slot 901 formed by the outer walls 806 and the stapler portion 900 of the second jaw 204. In this arrangement, as the forming link pivots about pin 1102, the staple former 902 is forced to slide up or down. It should be noted that, similar to the discussion of the first jaw 202 above, the staple-firing linkage can be formed on a single side of the second jaw 204, or can be symmetrically disposed on opposing sides of the second jaw 204. The use of symmetrical components on either side of the second jaw 204 can be seen in FIGS. 2-5, 8, and 12A-12C, for example.

At its proximal end, the forming link can be pivotally and slidably connected to a distal end of a firing link 1106 using a pin 1108. The firing link 1106 can be pivotally connected to the second jaw 204 by the pin 208, which, as discussed above, can also serve to pivotally connect the first jaw 202 to the second jaw 204. The firing link 1106 can include a slot 1110 formed therein and disposed at an angle to a longitudinal axis of the firing link 1106. The slot 1110 can receive a pin 1112 that is configured to control the firing of a staple or other fastener from the second jaw 204. Similar to controlling the movement of the first jaw 204 discussed above, the pin 1112 is also seated within a slot 810 (shown in FIG. 8) formed in the outer walls 806 of the second jaw 204. The slot 810, like slot 304, is disposed substantially parallel to a longitudinal axis of the second jaw 204. As a result, when the actuating cable 702 (shown in FIG. 7) is, for example, pulled, the pin 1112 will move proximally within the slot 810 of the second jaw 204. This also causes movement of the pin 1112 within the slot 1110 of the firing link 1106, which causes the firing link 1106 to rotate about pin 208. The rotation of the firing link 1106 causes an opposing rotation of the forming link 1100 about the pin 1102, which results in the translation of the staple former 902. In the embodiments disclosed herein, actuating the actuating cable 702 is sufficient to cause movement of the pin 1112 within the slot 1110 of the firing link 1106, which causes the firing link 1106 to rotate about the pin 208. It should be noted, however, that in some embodiments a biasing member, such as a spring, can be configured to assist movement of the firing link 1106.

FIGS. 11A-11C illustrate the operation of the above-described linkage. In FIG. 11A, the pin 1112 is disposed at a distal-most point in the slot 1110 of the firing link 1106. As a result, the firing link 1106 is rotated in a counter-clockwise direction, which, in turn, causes the forming link 1100 to rotate in a clockwise direction to slide the staple former 902 to the bottom of the figure. In this orientation, the staple former 902 is sufficiently clear of the stapler portion 900 to allow the spring 1012 to urge the next staple 1004 into the slot 901 formerly occupied by the staple former 902.

In FIG. 11B, the actuating cable 702 has begun to move proximally, pulling pin 1112 with it along slot 810 formed in the second jaw 204. The movement of the pin 1112 within the slot 1110 of the firing link 1106 causes the firing link 1106 to rotate about the pin 208 in a clockwise direction. This rotation causes the forming link 1100 to undergo an opposing, counter-clockwise rotation about the pin 1102, and the staple former 902 correspondingly begins sliding toward the top of the figure. As the staple former 902 passes back across the second jaw 204, it will encounter the staple 1004, which was previously pushed into the slot 901. The staple former 902 will exert a force on the staple 1004 to begin ejecting it out of the second jaw 204. Note that, in some embodiments, the staple former 902 may have a curved or textured face on the end that interfaces with staple 1004 in order to prevent the staple from slipping off the staple former 902.

FIG. 11C illustrates the finished firing position, in which the actuating cable 702 has pulled the pin 1112 to its proximal-most position in the slot 1110, thereby fully rotating the firing link 1106 in the clockwise direction. This rotation has caused the forming link 1100 to fully rotate in the counter-clockwise direction and pass the staple former 902 through its range of motion to fully eject the staple 1004 or other fastener from within the second jaw 204.

FIGS. 12A-12C illustrate in more detail the sliding of the staple former 902 within the second jaw 204. In these figures, the first jaw 202 and the second jaw 204 are shown in the closed position that is effective to engage tissue disposed between the two jaws. The staple former 902 begins in the position shown in FIG. 12A, raised above the inner stapler portion 900 enough such that a staple 1004 can be urged forward into the slot 901 in which the staple former 902 travels. As the movement of the actuating cable 702 rotates the firing link 1106, the forming link 1100 pivots around the pin 1102 and the pin 1104 drives the staple former 902 toward the first jaw 202. The staple former 902 interfaces with the staple 1004 and begins urging it toward the first jaw 202. The range of motion is complete when the staple former 902 has driven the staple 1004 completely out of the second jaw 204 such that it passes through any tissue disposed between the two jaws and deforms itself against the anvil portion 600 of the first jaw 202.

There are a variety of mechanical linkages known in the art suitable to move the staple former 902 such that it interfaces with and ejects a staple or other fastener from the second jaw 204 into the first jaw 202. These various linkages are considered to be within the scope of the present invention.

Tissue Acquisition Member

The above discussion focuses on the interaction of the first and second jaws to engage and secure tissue drawn between the jaws (i.e., securing the gastric fold or plication that is created by drawing tissue between the jaws). A tissue acquisition member or primary tissue acquirer, various embodiments of which are described in detail below, can be utilized to position tissue between the first and second jaws prior to delivering a fastener. In general, the tissue acquisition member can use a variety of techniques for engaging tissue, such as through vacuum, tissue penetration, pressure clamping, etc. The tissue acquisition member preferably extends substantially parallel to the jaws, and is positioned on one side of the jaws and is effective to capture tissue adjacent to an opposite side of the jaws and to pull the captured tissue through the jaws. In an exemplary embodiment, the tissue acquisition member is positioned in a first plane that extends substantially parallel to a second plane extending through each of the first and second jaws.

Referring back to FIG. 2, one embodiment of a tissue acquisition member 206 is shown in a configuration used for entry into a patient's body through a restricted lumen, such as the esophagus. In the position illustrated in FIG. 2, the tissue acquisition member 206 rests with an inferior, tissue-engaging surface 308 contacting a superior surface 309 of the second jaw 204. This minimizes the cross-sectional area of the staple applying assembly 200 during insertion into a patient's body.

The tissue acquisition member 206, much like the first and second jaws 202, 204, can be a generally elongate member. The elongate body of the tissue acquisition member 206 can define an inner lumen that connects to one or more vacuum ports disposed on the tissue engaging surface 308 of the tissue acquisition member 206 that are effective to engage and draw tissue against the tissue acquisition member. The tissue acquisition member 206 can also include a connection port 310 to connect to a vacuum source. The connection port 310 can be in communication with the inner lumen and the one or more vacuum ports of the tissue acquisition member 206.

The tissue acquisition member 206 can be connected to the staple applying assembly 200 by a hinge assembly or linkage 312. The linkage 312, which can include one or more hinge mechanisms, can allow the tissue acquisition member 206 to move vertically toward and away from the first and second jaws 202, 204 while maintaining its tissue engaging surface 308 in a plane that is substantially parallel to a second plane that extends through each of the first jaw 202 and the second jaw 204. There can also be some associated proximal/distal longitudinal motion because the linkage 312 swings the tissue acquisition member 206 through an arcuate path. In particular, a hinge linkage 312 having more than one hinge mechanism (e.g., as shown in FIGS. 2 and 5) can allow the tissue acquisition member 206 to move from the position shown in FIG. 2 to that shown in FIG. 5 without changing its rotational orientation with respect to the first and second jaws 202, 204.

In the embodiment illustrated in FIG. 2, the hinge linkage 312 includes a first connecting arm 210 that is pivotally connected at one end to a proximal end of an upper base plate 212 and pivotally connected at the other end to a proximal end of a lower base plate 214. The pivotal connection between the first connecting arm 210 and the upper or lower base plates 212, 214 can be accomplished using, for example, hinge pins 216. The hinge linkage 312 also includes a second connecting arm 218 that is pivotally connected at one end to a distal end of the upper base plate 212 and pivotally connected at the other end to a distal end of the lower base plate 214. The upper base plate 212 can be coupled to the tissue acquisition member 206 and the lower base plate 214 can be coupled to a superior surface of the first jaw 202. As a result, the first and second connecting arms 210, 218 form a 2-bar linkage that allows the tissue acquisition member 206 to swing through an arcuate path between, for example, a lower position shown in FIG. 2 to an upper position shown in FIG. 5

As mentioned above and shown in FIG. 3, the tissue acquisition member 206 can be coupled to the first jaw 202 alone such that the tissue acquisition member 206 moves in conjunction with the first jaw 202. In other words, as the first jaw opens and closes, the tissue acquisition member 206 moves with and remains parallel to the first jaw. The first jaw 202 can have a shape complementary to the shape of the tissue acquisition member 206 to allow the tissue acquisition member to pass into the space created between the first and second jaws 202, 204 when in the open position. For example, the tissue acquisition member 206 can be positioned vertically as shown in FIG. 2 (e.g., with a bottom surface 308 of the tissue acquisition member 206 being substantially coplanar with a top surface 309 of the second jaw 204), but with the first and second jaws 202, 204 in the open position. In such a configuration, the tissue acquisition member 206 can be disposed just above the space between the jaws, as shown in FIG. 3. In such a position, the tissue acquisition member 206 can be separated from the tissue on the opposite side of jaws by a distance roughly equal to the thickness of the jaws. The vacuum source can be activated, thereby causing the tissue acquisition member 206 to draw tissue against, for example, the inferior surface 308. A positioning cable connected to the hinge linkage 312 or to the tissue acquisition member 206 itself (e.g., in some embodiments, the positioning cable can also connect to the vacuum connection port 308 to deliver suction to the tissue acquisition member 206) can be used to raise the tissue acquisition member 206 away from the first and second jaws 202, 204, as shown in FIG. 5. Any tissue drawn against the inferior surface 308 would be drawn through the space between the first and second jaws 202, 204, thereby creating a gastric fold. The first and second jaws 202, 204 can then be moved to the closed position and one or more staples can be fired to secure the plication.

Still further, the tissue acquisition member 206 can be configured to pass between the open first and second jaws 202, 204 to better engage with tissue disposed on an opposing side of the jaws. For example, and as shown in FIG. 5, the connecting arms 210, 218 of the hinge linkage 312 can include one or more "S" bends 502. When in a raised orientation in which the tissue acquisition member 206 is vertically offset from the first and second jaws 202, 204 (as shown in FIG. 5), the S bends 502 provide a longitudinal offset that maintains the tissue acquisition member 206 in a location above the first and second jaws 202, 204 and longitudinally aligned with the jaws. Further, when the tissue acquisition member 206 is lowered into the space between the open first and second jaws 202, 204, the S bends 502 can allow the inferior, tissue engaging surface 308 to pass between the first and second jaws 202, 204 toward the tissue on the opposite side of the jaws. In particular, the tissue acquisition member 206 can be positioned such that the inferior, tissue engaging surface 308 is disposed below the superior surface 309 of the second jaw 204.

Endoscopic Controls

Figure 13:
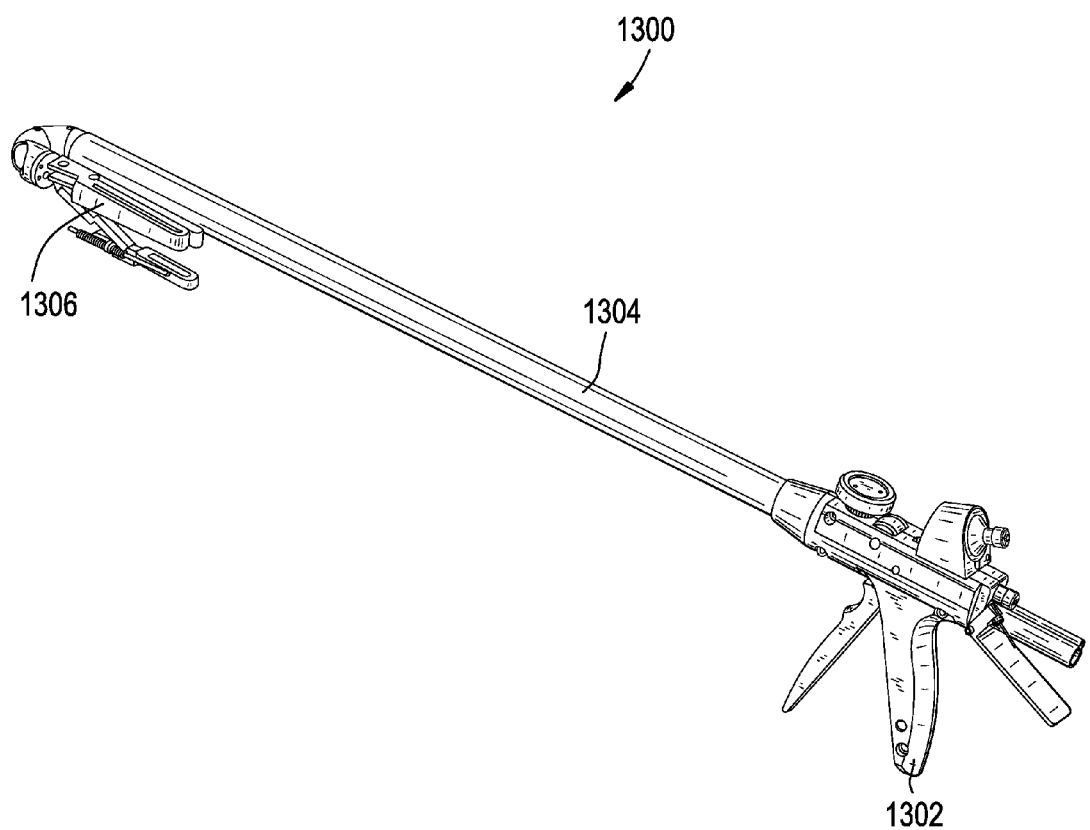
FIG. 13 is a perspective view of one embodiment of a surgical device including a staple applying assembly.

The staple applying assembly 200 disclosed above can be included as an end effector on a number of surgical devices. One exemplary device 1300 is illustrated in FIG. 13. The device includes a handle 1302 at its proximal end, a shaft or extension section 1304, and a staple applying assembly 1306 coupled to the distal end of the extension section 1304.

Figure 14:
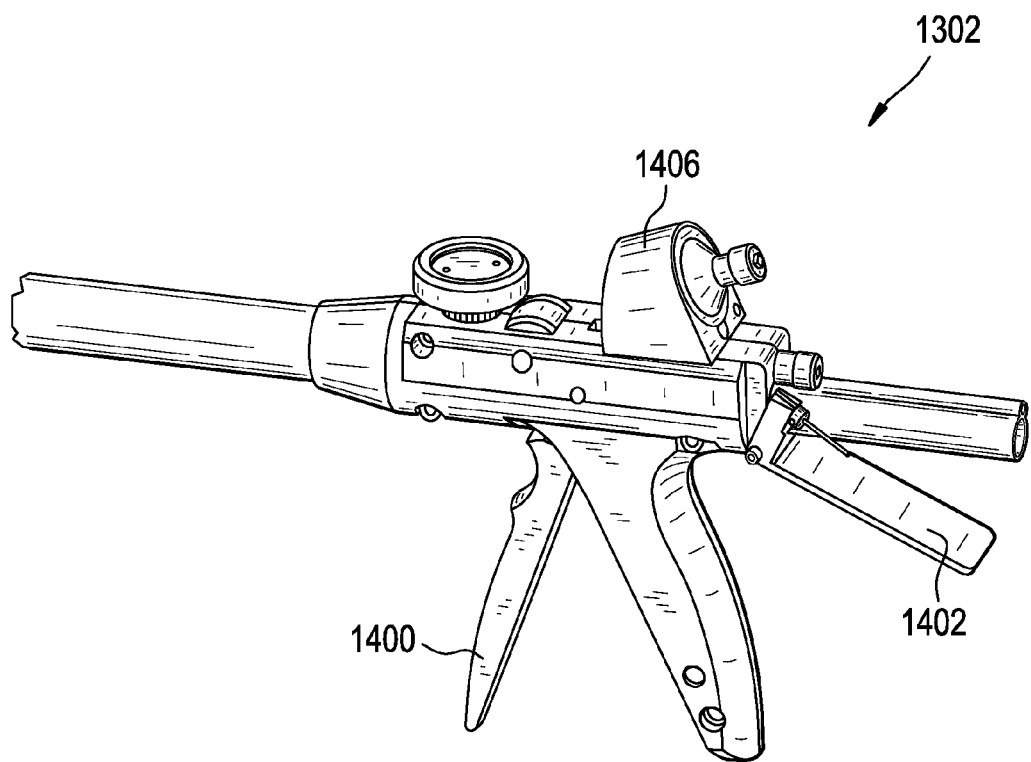
FIG. 14 is a side perspective view of one embodiment of a control handle of the surgical device of FIG. 13.
Figure 15:
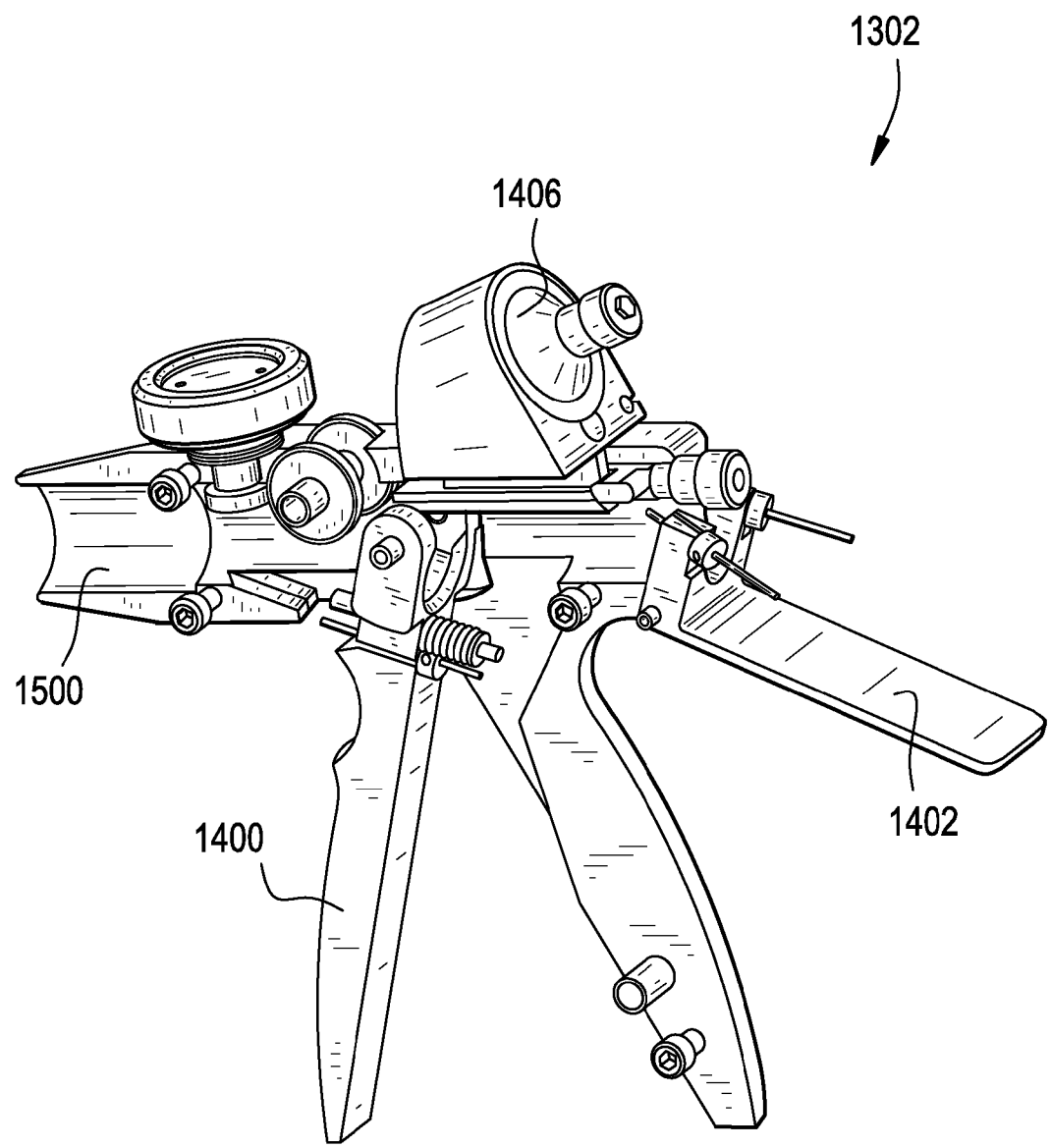
FIG. 15 is a side perspective cutaway view of the control handle of FIG. 14.
Figure 16:
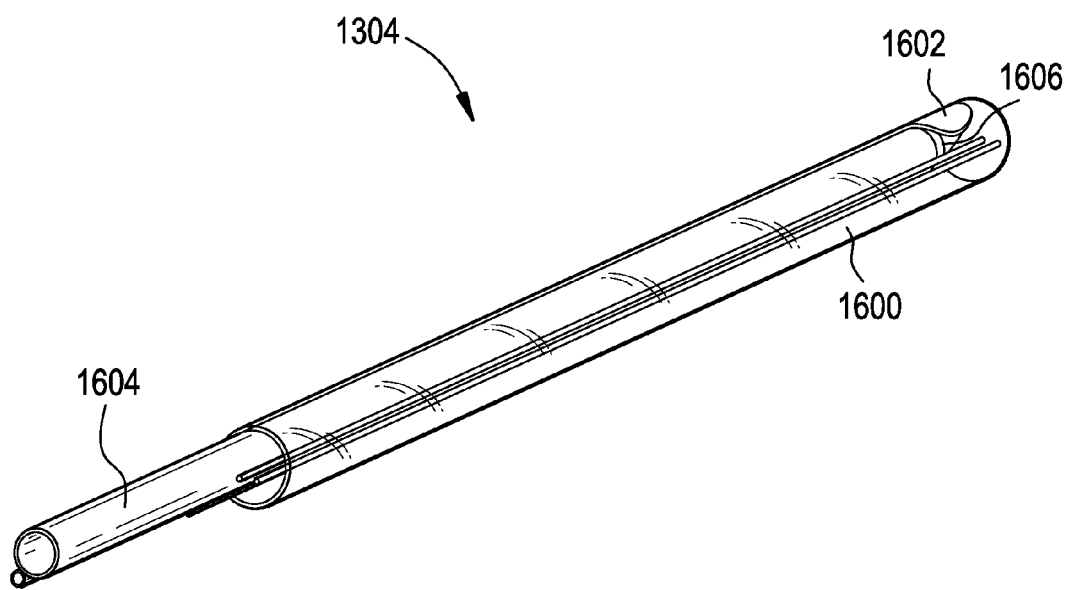
FIG. 16 is a side perspective transparent view of one embodiment of an elongate shaft of the surgical device of FIG. 13.

The handle 1302 can include any of a variety of actuation mechanisms to facilitate remote manipulation of the end effector staple applying assembly 1306. As shown in FIG. 14, the handle 1302 can include one or more levers, including a trigger lever 1400 and a palm lever 1402. FIG. 15 shows the handle 1302 without a cover, and illustrates that the levers 1400, 1402 can be used to tension one or more wires, such as the positioning cable 306 and actuating cable 702 discussed above.

The handle 1302 can also include one or more actuators 1406 configured to allow for rotation, as well as translation, of a cable extending to the end effector. In addition, the handle 1302 can include a central lumen 1500 to allow an operator to pass a visualizing (or other type of) scope through the handle and extension section to view or otherwise aid in the use of the end effector.

The extension section 1304 can be a generally elongate shaft that includes a hollow outer tube 1600 having one or more inner passages defined therethrough. For example, the outer tube 1600 can include an opening 1602 in a sidewall thereof near a distal end of the tube. A hollow inner tube 1604 can be disposed inside the outer tube 1600 and it can include an angled section 1606 that interfaces with the opening 1602 in the outer tube. In such a configuration, for example, a visualizing scope can be passed through the lumen 1500 in the handle 1302 and the inner tube 1604 of the extension section 1304 such that the scope extends from the opening 1602 in the sidewall of the outer tube and can visualize the end effector from a position just proximal of the surgical site. In further exemplary configurations, the opening 1602 can be configured in various geometries or contain additional components that effect the exit angle of the visualizing scope. Exemplary designs include ramps, levers, and elevators, all of which are considered within the scope of this invention. In addition to the inner tube 1604, the outer tube 1600 can carry one or more actuating cables that connect between the end effector and the handle 1302. These can include, for example, the positioning cable 306 and the actuating cable 702 discussed above.

Figure 17:
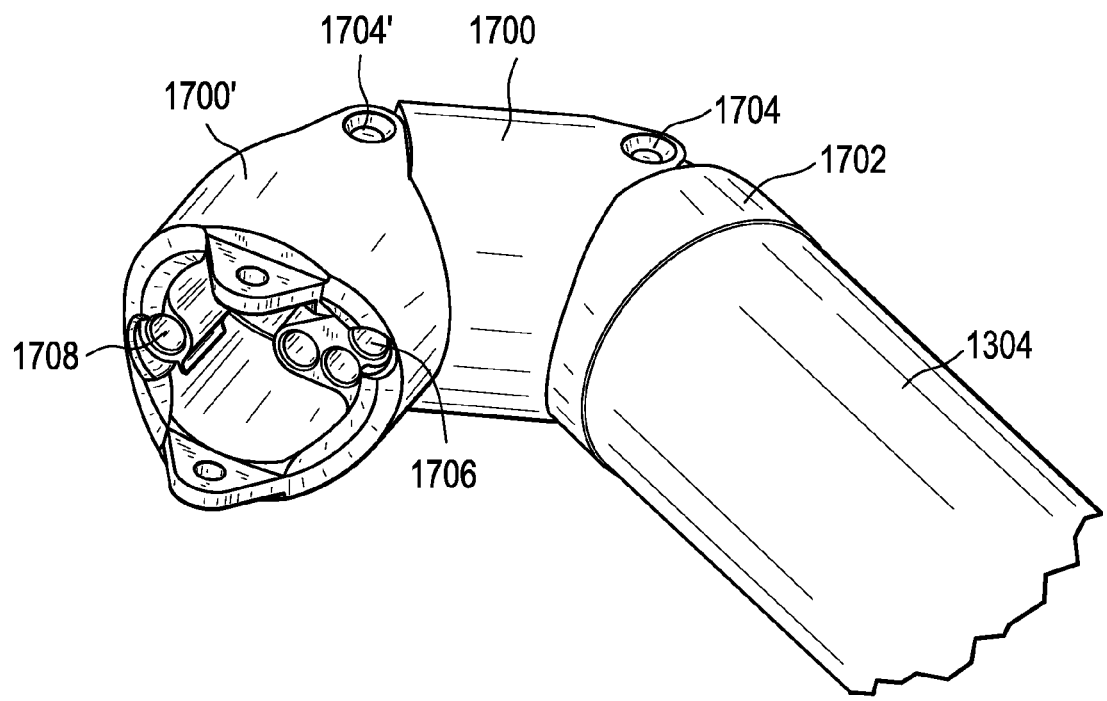
FIG. 17 is a perspective view of one embodiment of an articulating section of the surgical device of FIG. 13.

The staple applying assembly 1306 can be coupled directly to the distal end of the extension section 1304. However, in some embodiments, it can be beneficial to provide for articulation of the end effector. Accordingly, one or more articulating joints 1700 can be coupled between the distal end of the extension section 1304 and to the staple applying assembly 1306. A set of exemplary articulating joints is shown in FIG. 17. The set can include an end cap 1702 that couples directly to the distal end of the extension section 1304. Each articulating joint 1700, 1700' can connect to its neighboring joints via pivoting pins 1704, 1704'. Each articulating joint 1700 can include an inner lumen to allow passage of one or more actuating cables, endoscopes, etc. The articulating joints can be controlled using, for example, one or more actuating cables running down opposing sides of the articulating joint through, for example, passages 1706, 1708. As one actuating cable is tensioned at the handle 1302, the articulating joints will pivot toward the side carrying the tensioned cable. Selectively releasing and tensioning the one or more actuating cables can control the orientation of the articulating joints 1700, 1700'. Furthermore, additional joints may be disposed on the surgical device 1300 in the handle 1302, the extension section 1304, and/or the staple applying assembly 200. The articulating joint 1700 is an exemplary joint. Such joints may be configured to provide additional motion, in either or any of the up, down, left, right, in, or out directions, as shown in FIG. 1. In some embodiments, the staple applying assembly 1306 can be coupled to the extension section 1304 by four articulating joints.

Figure 18:
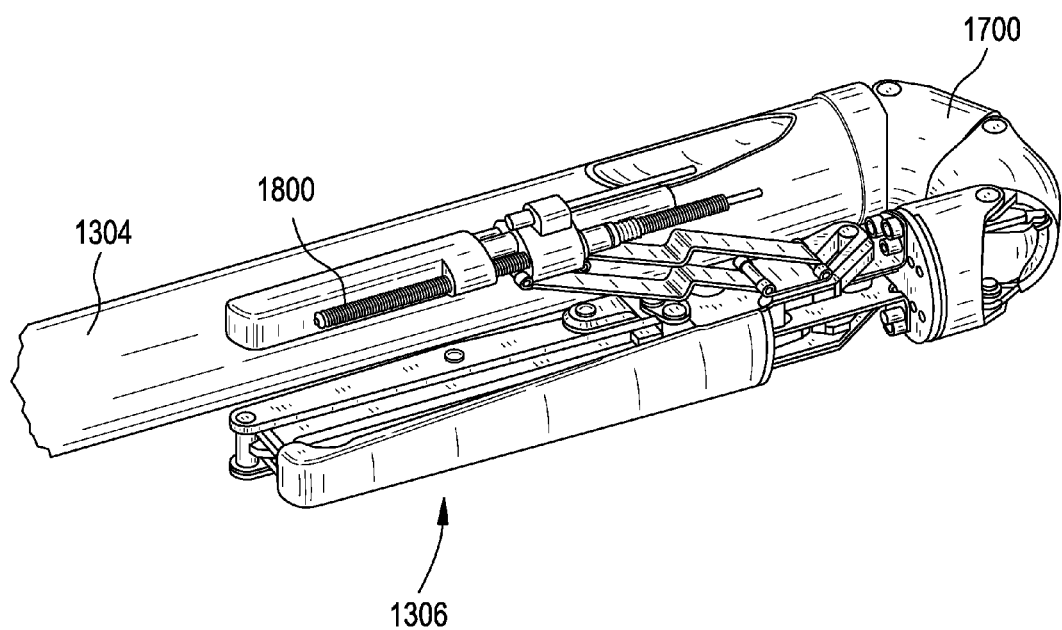
FIG. 18 is a side perspective view of one embodiment of a staple applying end effector of the surgical device of FIG. 13.

FIG. 18 illustrates an embodiment of the staple applying assembly 1306 disposed on the surgical device 1300. As shown in the Figure, the articulating joints 1700 can, in some embodiments, provide for large ranges of articulating movement. This can be beneficial when forming a plurality of gastric plications, as discussed in more detail below.

Translating Tissue Acquirer

When forming a gastric plication, it is often necessary to secure the plication with more than one staple or fastener. In many cases, it can be desirable to form one or more lines of staples to secure a plication. As mentioned above, the hinge linkage 312 that connects the tissue acquisition member 206 to the first jaw 202 swings the tissue acquisition member through an arcuate path that involves both vertical movement toward and away from the first and second jaws 202, 204 (i.e., movement up and down above the jaws) and proximal or distal longitudinal translation (i.e., translation along a longitudinal axis of the jaws). This longitudinal motion can be effective to place the distal end of the jaws (that ejects the staples or other fasteners) forward or behind a previously placed staple, but the range of motion can be limiting. Further, the longitudinal and vertical movements occur together, meaning an uneven or arc-shaped line may be formed.

In some embodiments, it can thus be beneficial to include an indexing mechanism for translating the tissue acquisition member 206 longitudinally after it has been raised to a position that is vertically offset from the first and second jaws 202, 204. Such a mechanism can allow the tissue to be translated longitudinally through the jaws, thereby allowing a row of staples to be applied to the tissue without the need to release and recapture the tissue at multiple locations. The staple applying assembly illustrated in FIG. 18 includes an indexing mechanism in the form of a lead screw 1800 that can rotate to longitudinally adjust the position of the tissue acquisition member above the first and second jaws.

Figure 19:
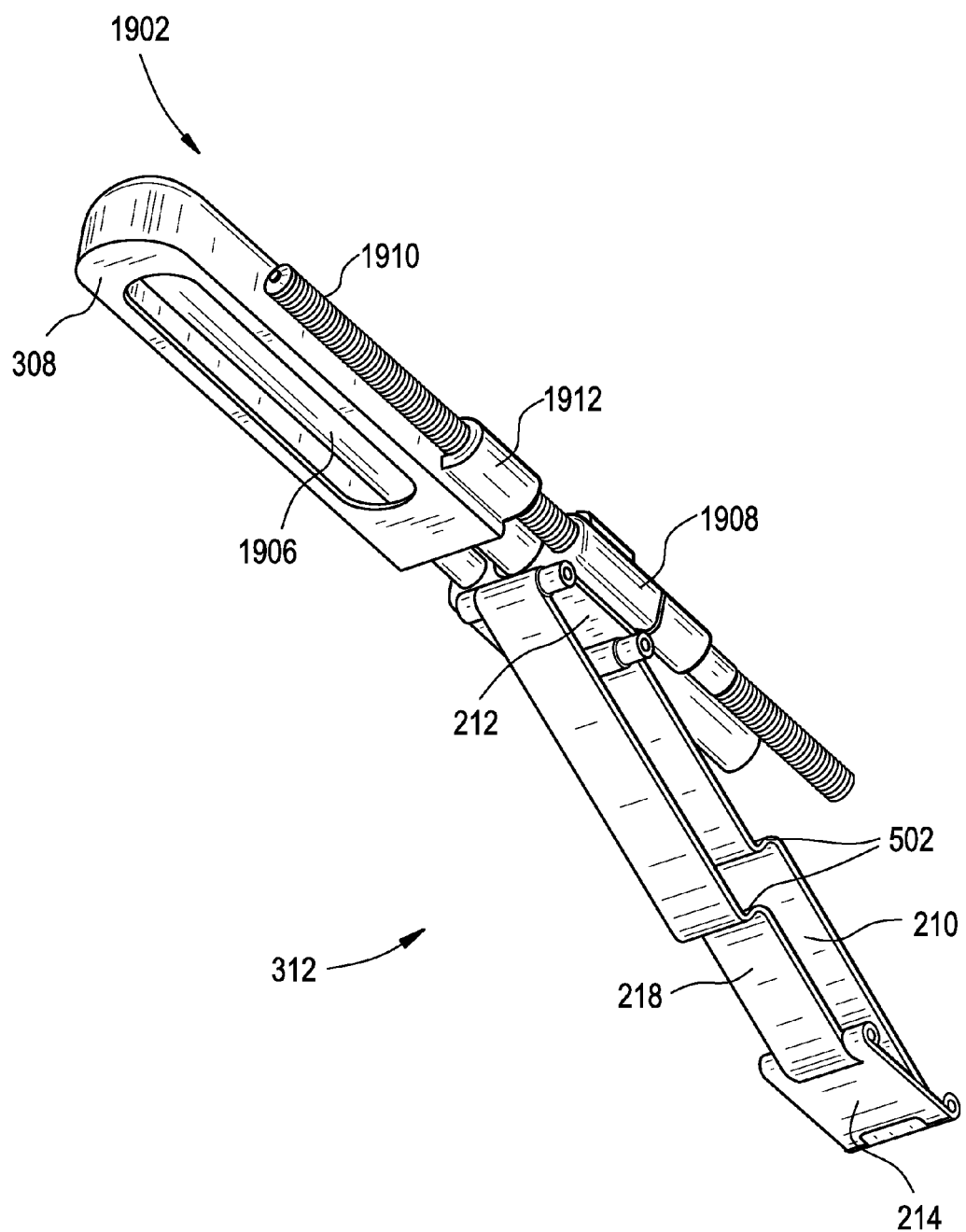
FIG. 19 is a bottom perspective view of one embodiment of a tissue acquisition member of the surgical device of FIG. 13.
Figure 20:
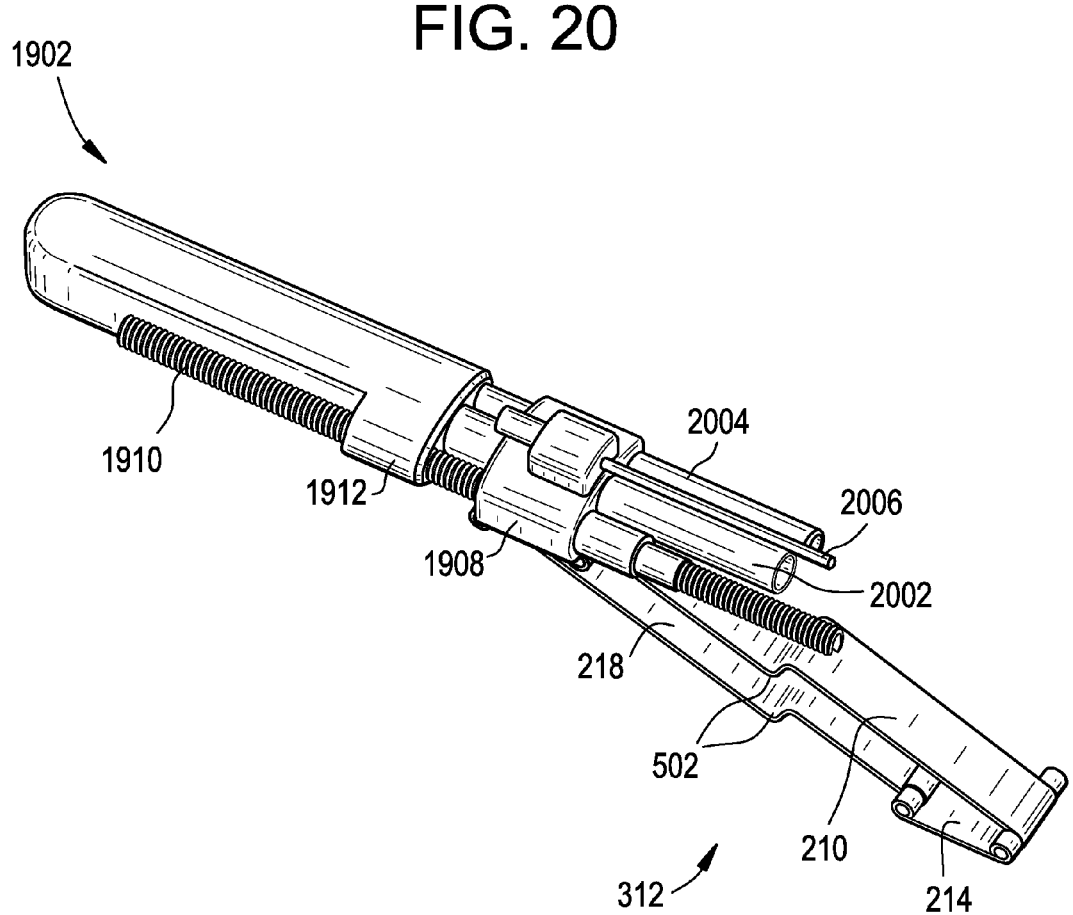
FIG. 20 is a top perspective view of the tissue acquisition member of FIG. 19.

FIGS. 19 and 20 illustrate one embodiment of a tissue acquisition member 1902 and hinge linkage 312 in isolation. As shown in the figures, the assembly is similar to those described above. The hinge linkage 312 can include a hinge base 214 configured to couple with the first jaw 202, and two connecting arms 210, 218 with "S" bends 502 that connect to a second hinge base 212 coupled to the tissue acquisition member 1902. The tissue acquisition member 1902 includes an inferior, tissue engaging surface 308 having, in this embodiment, a single large vacuum port 1906. The vacuum port is in communication with a vacuum supply through a connecting tube 2002.

The illustrated tissue acquisition member 1902 includes an additional component, namely a tissue acquisition member base 1908. The base 1908 is coupled to the second hinge base 212 and seats a threaded rotating lead screw 1910. The rotating lead screw 1910 extends distally from the base 1908 in a direction parallel to a longitudinal axis of the tissue acquisition member 1902. The lead screw 1910 can be configured to rotate without translating with respect to the base 1908, as explained below.

The tissue acquisition member 1902 can be narrower than the embodiments described above so as to accommodate a protrusion 1912 on one side thereof that has a threaded bore formed therethrough in a direction parallel to a longitudinal axis of the tissue acquisition member. The threaded protrusion can receive the threaded lead screw 1910 such that the tissue acquisition member translates proximally and distally along the lead screw 1910 as the lead screw is rotated.

On an opposing side of the tissue acquisition member 1902 from the protrusion 1912, a guide pin 2004 extends from the tissue acquisition member through a bore formed in the base 1908. The guide pin 2004 slides freely through the bore in the base 1908, and serves to prevent the tissue acquisition member 1902 from rotating as the lead screw 1910 is rotated.

Any of several actuating cable configurations are possible with the lead screw 1910. For example, as illustrated in FIGS. 19 and 20, a positioning cable 2006 can be attached to the base 1908 so as to control the vertical offset of the tissue acquisition member 1902 from the first and second jaws 202, 204. A second, rotating actuating cable can then be coupled to the lead screw 1910 to actuate its rotation and thereby control the longitudinal translation of the tissue acquisition member 1902. Alternatively, a single actuating cable can be employed that connects to the lead screw 1910 in the base 1908. Applying a tensioning force to the actuating cable can be effective to control the vertical offset of the tissue acquisition member 1902, while rotation of the cable can be effective to control the longitudinal translation of the tissue acquisition member.

Figure 21A:
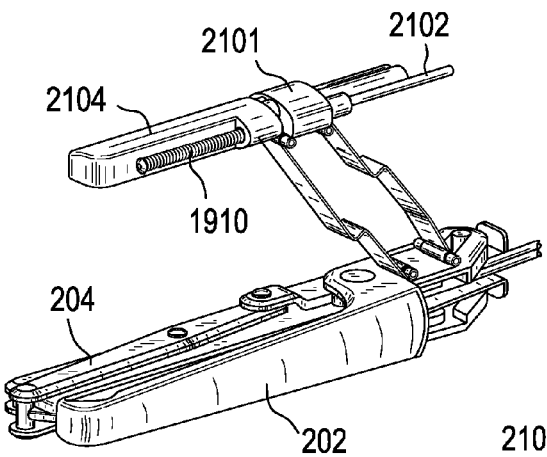
FIG. 21A is a front perspective view of one embodiment of a staple applying assembly including a longitudinally translating tissue acquisition member in a first position.
Figure 21B:
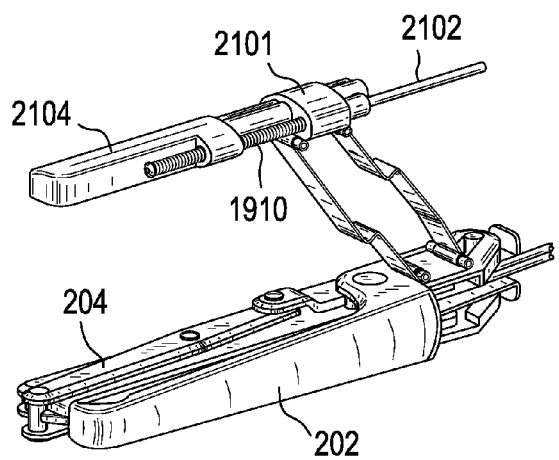
FIG. 21B is a front perspective view of the staple applying assembly of FIG. 21A with the tissue acquisition member in a second position.
Figure 21C:
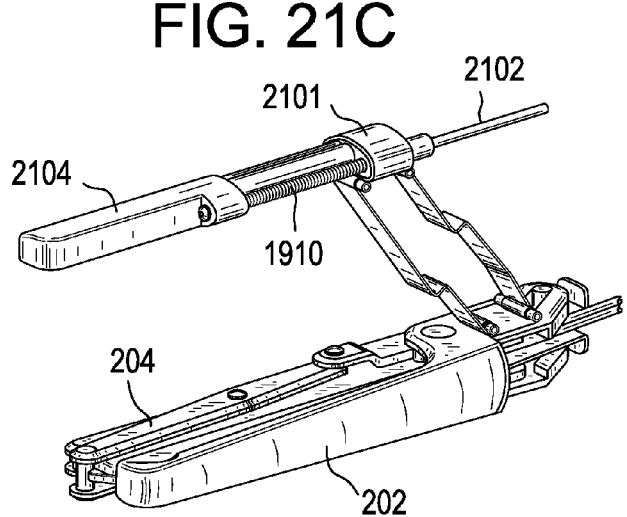
FIG. 21C is a front perspective view of the staple applying assembly of FIG. 21A with the tissue acquisition member in a third position.

FIGS. 21A-C illustrate an exemplary embodiment of this single control wire configuration. For example, the tissue acquisition member base 2101 does not include an extension on its top surface to receive a positioning cable, in contrast to the base 1908 illustrated in FIGS. 19 and 20. Rather, the single actuating cable 2102 extending into the lead screw 1910 serves both purposes. FIG. 21A illustrates the tissue acquisition member 2104 in its proximal-most position on the lead screw 1910. FIG. 21B illustrates the tissue acquisition member 2104 in an intermediate position, and FIG. 21C illustrates the tissue acquisition member 2104 in its distal-most position on the lead screw 1910.

Figure 22:
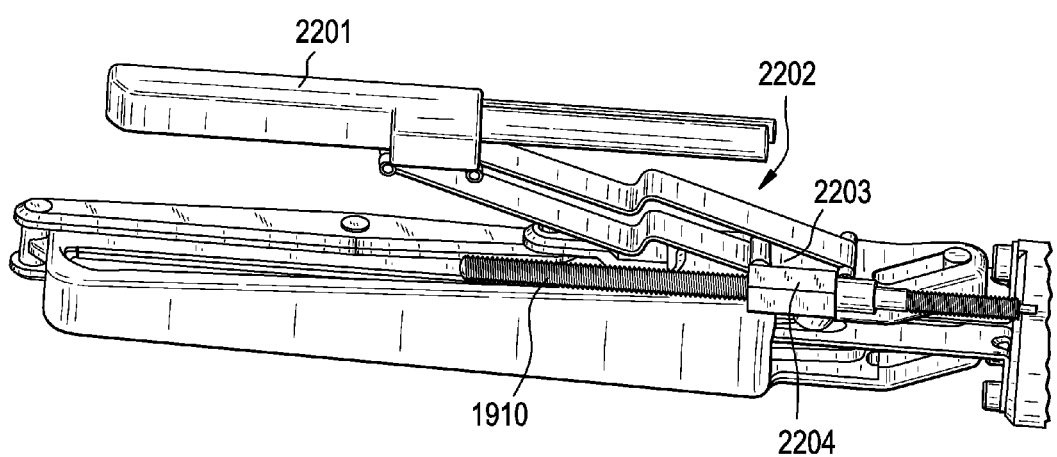
FIG. 22 is a side perspective view of another embodiment of a staple applying assembly including a translating hinge base.

There are a variety of alternative ways to longitudinally translate the tissue acquisition member with respect to the first and second jaws 202, 204. For example, in an exemplary embodiment illustrated in FIG. 22, the lead screw has been moved from the tissue acquisition member 2201 to the base of the hinge linkage 2202. In particular, a hinge base 2203 can be mounted to a platform having a protrusion 2204 on one side thereof with a threaded bore formed therein. In addition, a baseplate (not shown) can be mounted to the first jaw 202 and configured to hold the lead screw 1910 just above the surface of the first jaw 202 and parallel to a longitudinal axis of the first jaw. The protrusion 2204 can receive the lead screw 1910 such that, as the lead screw is rotated, the hinge base 2203 (along with the rest of the hinge linkage 2202 and the tissue acquisition member 2201) translates proximally or distally along the lead screw 1910. An additional guide pin or other stabilizing member can also be included, similar to the guide pin 2004 of FIG. 20, to prevent rotation of the hinge base 2203 and tissue acquisition member 2201.

Locating the lead screw 1910 on the first jaw 202 can eliminate the "S" bend that can form in the lead screw actuating cable when the tissue acquisition member is raised above the first and second jaws 202, 204 by a significant amount. However, this can require use of a separate cable to rotate the lead screw, as well as offset positioning of the tissue acquisition member 2201 from the first and second jaws 202, 204 because the lead screw is located on the first jaw and does not vertically offset from the jaw.

Figure 23A:
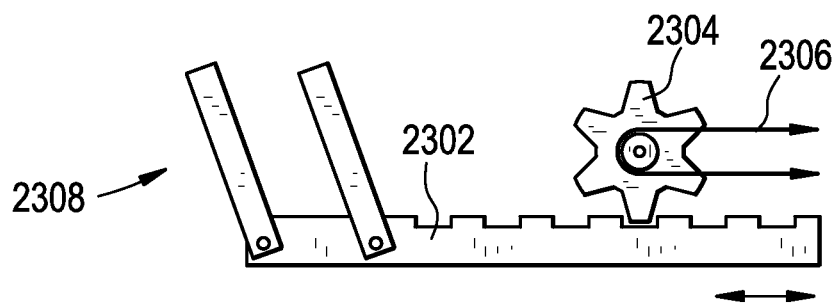
FIG. 23A is a side view of another embodiment of a translating hinge base.

In other embodiments, a lead screw can be replaced with an alternative indexing mechanism, such as a rack and pinion gear set. FIG. 23A illustrates an exemplary embodiment of a hinge base 2302 that has a rack gear set formed therein. The gear set can be slidably disposed in a track formed on, for example, the first jaw 202. The first jaw 202 can also be configured to rotatably retain a pinion gear 2304 a distance above the track such that it interfaces with the rack gear set of the hinge base 2302. The pinion gear 2304 can be controlled by a control wire pulley system 2306, thereby allowing an operator to turn the pinion gear 2304 in either direction. By turning the pinion gear 2304 (which is mounted on the first jaw 202), the hinge base 2302 will translate proximally or distally within the track formed in the first jaw 202. As a result, the entire hinge linkage 2308 and tissue acquisition member will also longitudinally translate.

Figure 23B:
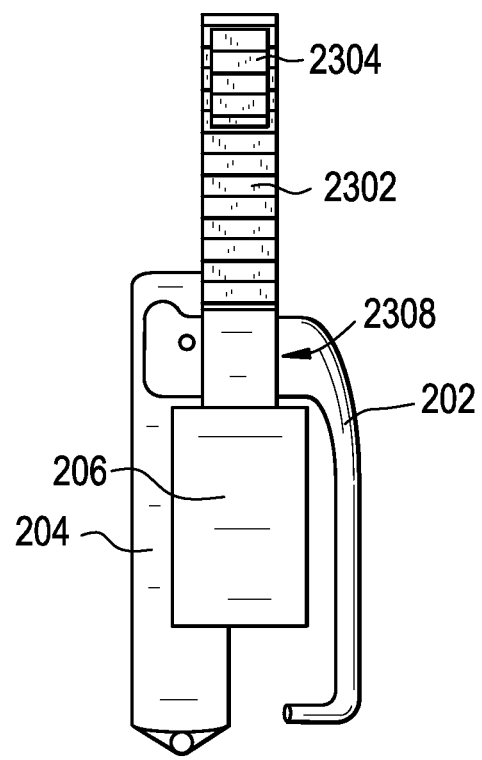
FIG. 23B is a top view of one embodiment of a staple applying assembly including the translating hinge base of FIG. 23A.

FIG. 23B illustrates the rack and pinion gear set embodiment from a top view. The figure shows the first jaw 202, the second jaw 204, the tissue acquisition member 206, the hinge linkage 2308, the hinge base 2302 with rack gear set, and the pinion gear 2304. Note that the illustration is not shown to scale for ease of viewing.

Figure 24:
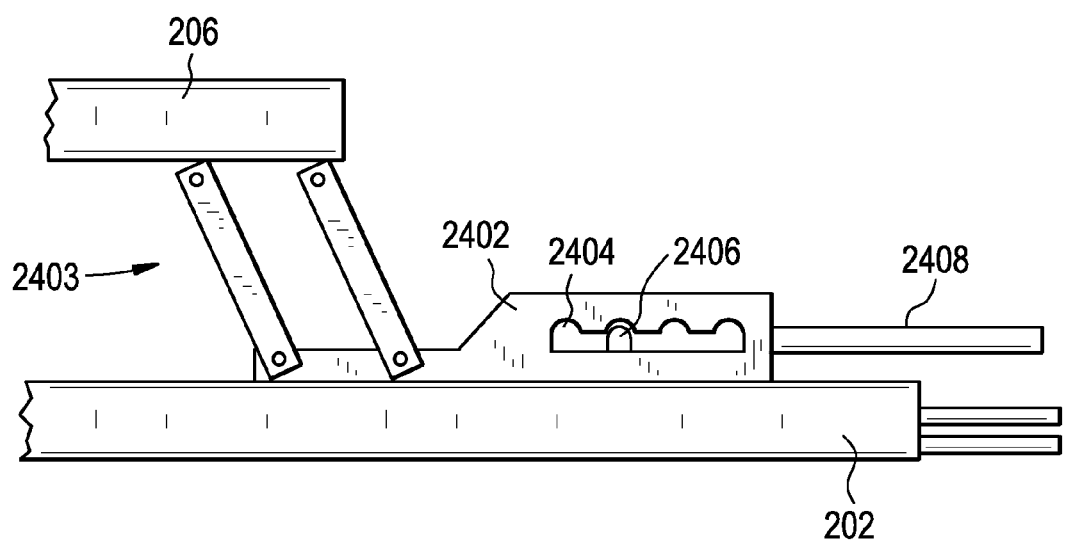
FIG. 24 is a side view of another embodiment of a translating hinge base.

Another alternative indexing mechanism involves the use of a hinge base with a plurality of indexed grooves that can seat a hinge pin. FIG. 24 illustrates an exemplary embodiment in which a hinge base 2402 is slidably disposed on a surface of the first jaw 202. The hinge base forms part of the hinge linkage 2403 connected to the tissue acquisition member 206, but also includes a portion having a plurality of indexed grooves 2404 formed therein. The plurality of indexed grooves 2404 can be spaced apart at a variety of distances. In an exemplary embodiment, the plurality of grooves 2404 can be separated by about 2 centimeters. The first jaw 202 can have a hinge pin 2406 rigidly attached thereto and configured to be seated in one of the plurality of indexed grooves 2404. The hinge pin 2406 can have an asymmetric profile such as a flat bottom surface and a curved top surface. This profile can match the shape of the plurality of indexed grooves 2404, and can prevent undesired motion of the hinge base 2402.

A control wire or rigid pusher element 2408 can also be attached to the hinge base 2402. Further, the hinge base 2402, or at least a portion thereof containing the plurality of indexed grooves 2404, can be formed from a material strong enough to retain the hinge pin 2406 within an indexed groove 2404 during normal use of the tissue acquisition device, but flexible enough to allow the hinge pin 2406 to move from one indexed groove to another upon application of tension or thrust from an operator. As a result, the operator can, for example, pull the hinge base 2402 in a proximal direction to seat or snap the hinge pin 2406 into the next-most distal indexed groove 2404, thereby translating the hinge base 2402, hinge linkage 2403, and tissue acquisition member 206.

Secondary Tissue Acquirer

In some embodiments, the tissue acquisition member alone may not be sufficiently strong (e.g., may not have sufficient vacuum strength) to maintain its hold on tissue drawn against the tissue engaging surface as the tissue acquisition member is raised away from the first and second jaws. As a result, a secondary tissue acquirer can be employed to help retain the position of tissue drawn against the tissue acquisition member. A person skilled in the art will appreciate that any secondary tissue acquisition member can be using with any primary tissue acquisition member disclosed herein, or alternatively the secondary tissue acquisition member can be used instead of the primary tissue acquisition members disclosed herein.

The secondary tissue acquirer can have a variety of configurations. Generally, the secondary tissue acquirer is coupled to the tissue acquisition member and configured to engage and retain tissue in a particular position relative to the tissue acquisition member. The secondary tissue acquirer can include any of one or more hooks, graspers, and clamps pivotally or otherwise connected to the tissue acquisition member.

Figure 25:
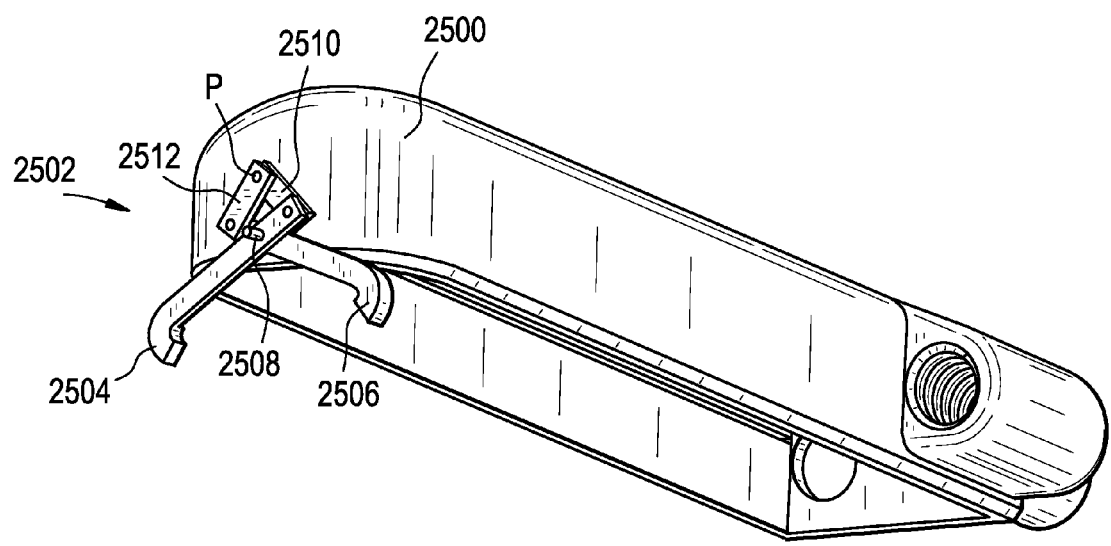
FIG. 25 is a front perspective view of a tissue acquisition member including a secondary tissue acquirer that includes one or more graspers.

In one exemplary embodiment illustrated in FIG. 25, a tissue acquisition member 2500 includes a secondary tissue acquirer 2502 connected to its distal end. The secondary tissue acquirer 2502 includes opposing graspers 2504, 2506 that are pivotally connected to a pin 2508 that extends from the distal end of the tissue acquisition member 2500. The proximal end of the grasper 2504 is pivotally connected to a linkage 2510, and the proximal end of the grasper 2506 is pivotally connected to a linkage 2512. The linkages 2510, 2512 are, in turn, connected to each other pivotally at point P.

To operate the secondary tissue acquirer 2502, an actuating cable can be attached to point P to pull it upward, thereby causing the graspers 2504, 2506 to pivot around the pin 2508 toward each other. This is similar to the operation of an ice block pick. When the graspers 2504, 2506 pivot toward each other, they can engage any tissue disposed therebetween. Further, the graspers 2504, 2506 can be formed with either sharp or dull distal ends to aid in tissue engagement.

An actuating cable connected to the secondary tissue acquirer 2502 can be routed, for example, over the top of the tissue acquisition member 2500. In some embodiments, the tissue acquisition member 2500 may have a track, depression, or other guide formed on its upper surface to accommodate the actuating cable extending to the secondary tissue acquirer 2502 on the distal end of the tissue acquisition member 2500.

Figure 26:
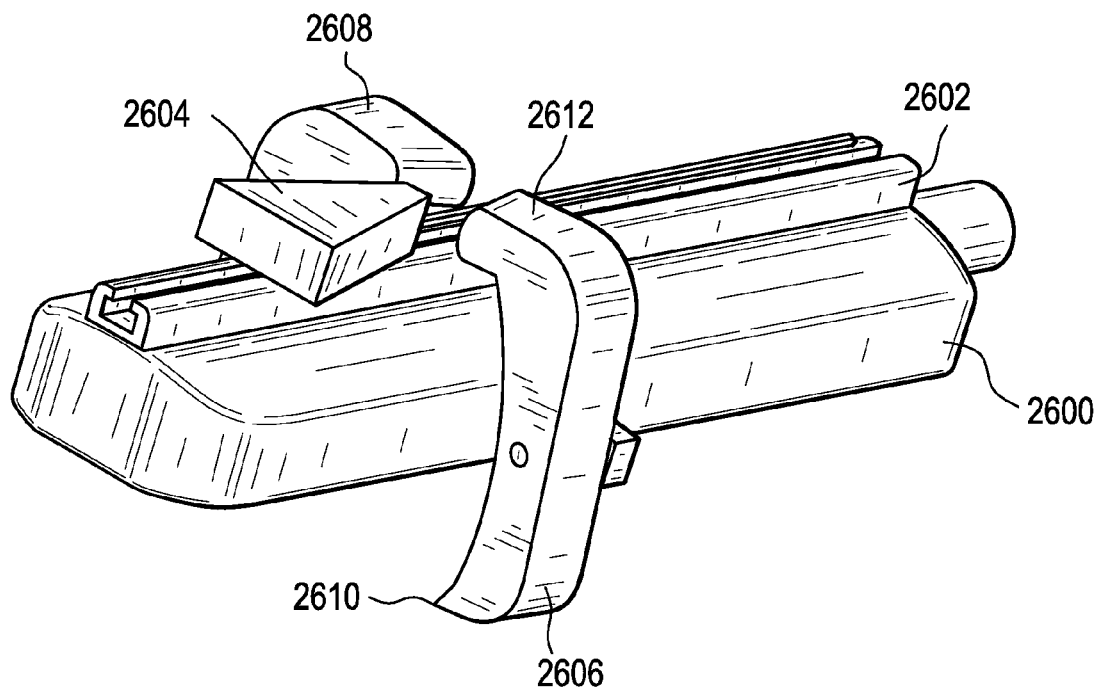
FIG. 26 is a front perspective view of another embodiment of a secondary tissue acquirer that includes one or more clamps.

An exemplary track formed on an upper surface of a tissue acquisition member is illustrated in FIG. 26, which shows another embodiment of a secondary tissue acquirer. In this embodiment, the tissue acquisition member 2600 includes a track 2602 formed on an upper surface thereof and configured to slidably receive one or more triangular wedge members 2604. The wedge member 2604 (or, if there are more than one, each wedge member) can, in turn, be connected to one or more actuating cables seated within, along, or adjacent to the track 2604. The tissue acquisition member 2600 also features two or more clamps 2606, 2608 pivotally connected to the tissue acquisition member 2600. The clamp 2606 includes a tissue-engaging distal end 2610 that can be blunt or sharp, and a proximal end 2612 configured to engage with the wedge member 2604. Though not shown clearly in the figure, the opposing clamp 2608 can include similar features. In the embodiments disclosed herein, a biasing member, such as a spring, can be configured to assist movement of the clamps 2606, 2608.

To operate the secondary tissue acquirer, an operator can slide wedge member 2604 in a proximal direction within track 2602 by, for example, pulling on an actuating cable connected to the wedge member 2604. As the wedge member 2604 moves proximally, its sides will interface with the proximal ends of the clamps 2606, 2608. The triangular shape of the wedge member 2604 will progressively push the proximal ends of the clamps 2606, 2608 laterally away from a longitudinal axis of the tissue acquisition member 2600 as the wedge member 2604 is advanced proximally. Due to the pivotal connection of the clamps 2606, 2608 to the tissue acquisition member 2600, the distal ends of the clamps 2606, 2608 will move inward toward each other, thereby engaging any tissue drawn against the lower surface of the tissue acquisition member.

While FIG. 26 illustrates one exemplary configuration for the clamps and wedge member, it should be noted that a variety of alternative configurations are also possible. For example, multiple sets of clamps can be used with multiple wedge members. In addition, alternative actuation technologies can be used to drive the movement of the wedge member within the track on the tissue acquisition member. For example, the wedge member can be slidably driven along the track using pneumatic force, rather than one or more actuating cables.

Figure 27A:
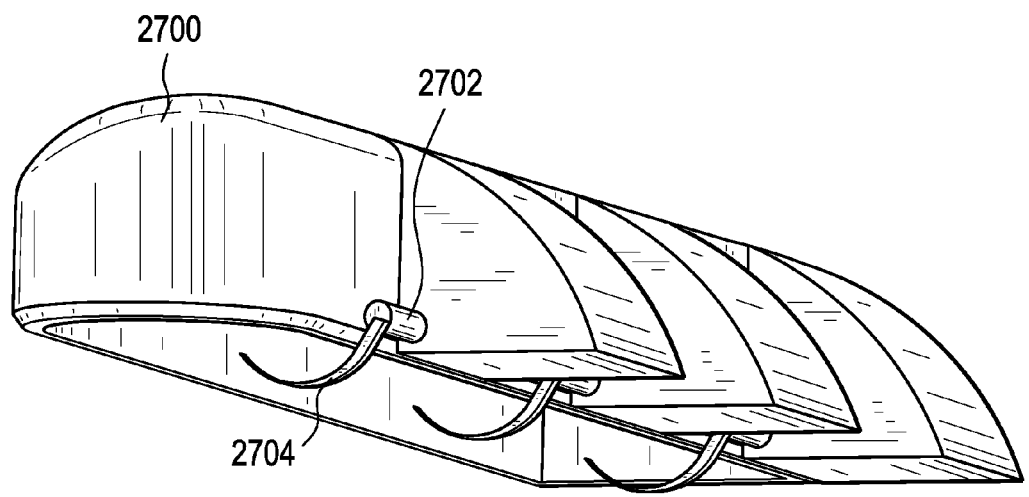
FIG. 27A is a front perspective view of another embodiment of a secondary tissue acquirer that includes one or more hooks.
Figure 27B:
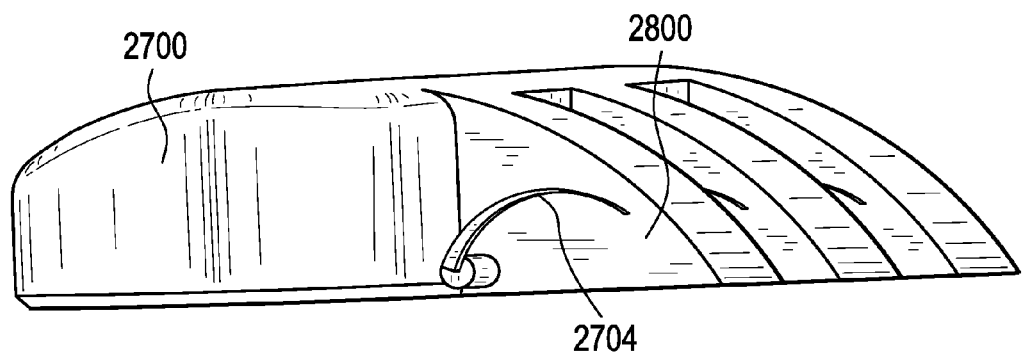
FIG. 27B is an alternative front perspective view of the tissue acquisition member of FIG. 27A showing the one or more hooks in a second position.

FIGS. 27A and 27B illustrate a third embodiment of a secondary tissue acquirer that utilizes one or more grasping hooks to engage and retain tissue drawn against the tissue acquisition member. In this embodiment, a tissue acquisition member 2700 includes a rotatable shaft 2702 extending through a portion of the body of the tissue acquisition member. One or more tissue-engaging hooks 2704 that are coupled to the rotatable shaft such that, as the shaft rotates, they swing in a plane that is angularly offset from (i.e., not parallel to) a longitudinal axis of the tissue acquisition member 2700.

The rotatable shaft 2702 can be controlled by an actuating cable coupled to the shaft at the proximal end of the tissue acquisition member 2700. The shaft 2702 and actuating cable can be coupled such that rotation of the actuating cable creates a corresponding rotation of the shaft.

FIG. 27B illustrates the tissue acquisition member 2700 with the hooks 2704 in a retracted position. In order to prevent the hooks from engaging tissue in the retracted position, the tissue acquisition member can include one or more protruding sections 2800 that extend beyond the length of the hooks 2704 and prevent their distal ends from engaging with surrounding tissue.

Figure 28A:
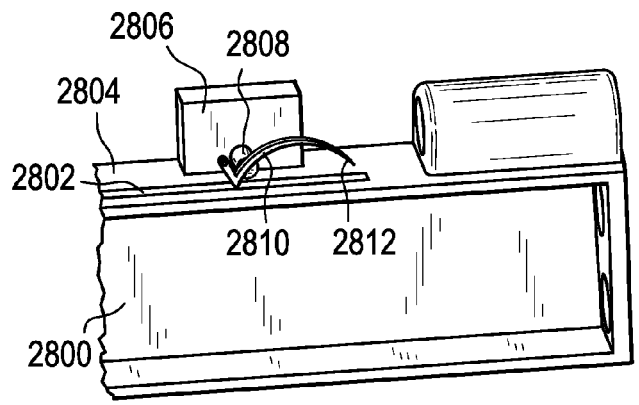
FIG. 28A is a bottom perspective view of another embodiment of a secondary tissue acquirer that includes a rotating hook.
Figure 28B:
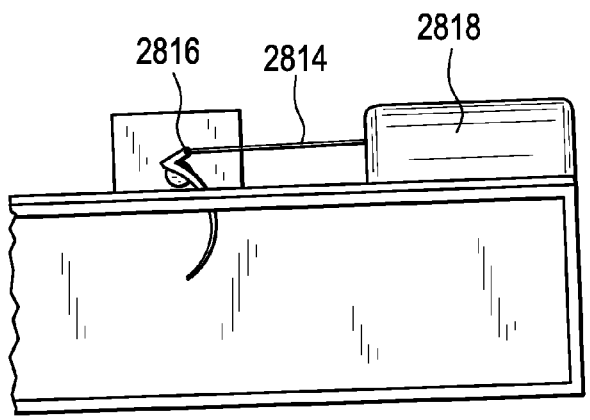
FIG. 28B is a bottom perspective view of the rotating hook of FIG. 28A in a second position.
Figure 28C:
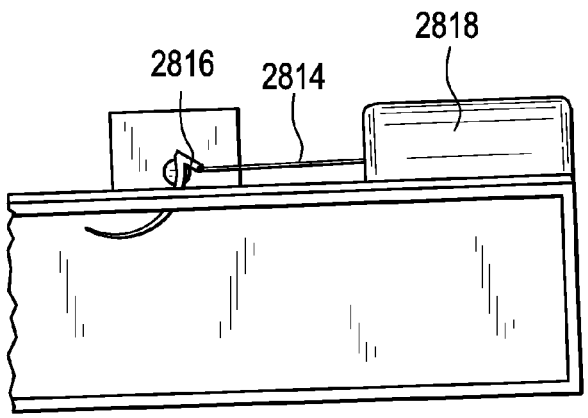
FIG. 28C is a bottom perspective view of the rotating hook of FIG. 28A in a third position.

FIGS. 28A-28C illustrate yet another embodiment of a secondary tissue acquirer coupled to the tissue acquisition member. The secondary tissue acquirer includes a hook mounted on a rotatable shaft such that the hook can swing into tissue drawn against the lower surface of the tissue acquisition member. FIGS. 28A-C illustrate the hook in three positions: a retracted position in FIG. 28A, an intermediary position in FIG. 28B, and a fully engaged position in FIG. 28C.

As shown in FIG. 28A, a tissue acquisition member 2800 can have a slot 2802 formed in a sidewall 2804 thereof parallel to a longitudinal axis of the tissue acquisition member. The tissue acquisition member 2800 can also include a protrusion 2806 from the sidewall 2804 that is located above the slot 2802, and a short rotatable shaft 2808 can extend from a lower surface of the protrusion. A hook 2810 can be coupled to the shaft such that, as the shaft rotates, the hook moves in a plane that is parallel to the lower surface of the tissue acquisition member and the slot 2802. Further, a distal end 2812 of the hook 2810 can swing through the slot 2802 such that it crosses a plane defined by the sidewall 2804 of the tissue acquisition member 2800.

To control the rotation of the hook 2810, a suture 2814 or thin actuating cable can be attached to a proximal end 2816 of the hook. The proximal end 2816 of the hook can be offset from the rotatable shaft 2808 such that tensioning the suture 2814 can cause the shaft, and therefore the hook 2810, to rotate. The suture 2814 can, in turn, be connected to, for example, a linear actuator housed in a second protrusion 2818 on the sidewall 2804 of the tissue acquisition member 2800. Accordingly, rotation of the hook 2810 can be controlled by actuation of the linear actuator to tension the suture 2814. The rotatable shaft 2808 can also include a spring member to bias the shaft and return the hook 2810 to the retracted position shown in FIG. 28A upon release of the tension on the suture 2814.

A number of variations on this secondary tissue acquirer configuration are also possible. For example, the hook 2810 can be configured to be disposed just below the lower surface of the tissue acquisition member 2800, thereby eliminating the need for a slot 2802. Furthermore, the tissue acquisition member 2800 can include more than one hook and actuator pair, or could include a single actuator connected to a series of hooks for simultaneously rotating multiple hooks so as to engage tissue drawn against the tissue acquisition member 2800.

Low Profile Insertion Position

In certain situations, it can be desirable to create larger plications, or plications that are secured by multiple lines of staples or other fasteners. However, devices configured to apply multiple fasteners, or sets of fasteners, can often be larger in size, which is a concern for endoscopic procedures. There is a general inverse relationship between the rigid length and the diameter of a surgical device that can be introduced endoscopically. This means that as a device increases in diameter, its rigid length must decrease in order to permit endoscopic entry and manipulation within a patient. Conversely, a device having a large rigid length will need to have a smaller diameter to allow it to be endoscopically inserted into a patient. To address this problem, the devices disclosed below utilize a low profile insertion position that reduces the diameter of the staple applying assembly such that it can be inserted into a patient endoscopically despite the use of, for example, larger jaws or a large staple cartridge.

Figure 29:
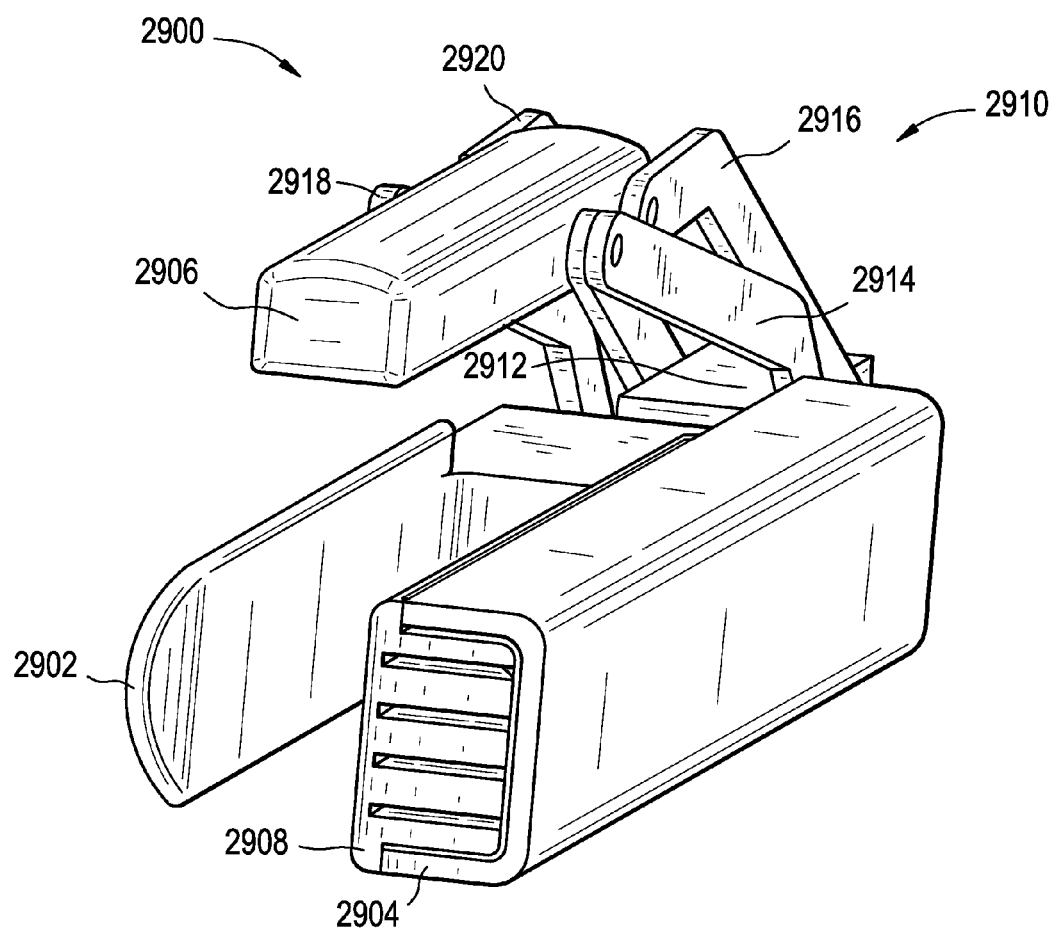
FIG. 29 is a front perspective view of one embodiment of a staple applying assembly including a 4-bar hinge linkage and multi-line staple cartridge.

FIG. 29 illustrates another embodiment of a staple applying assembly or stapling member 2900. Similar to the staple applying assembly 200 discussed above, staple applying assembly 2900 includes a first jaw 2902, a second jaw 2904, and a tissue acquisition member 2906. In the illustrated embodiment, however, the second jaw 2904 includes a multi-line staple cartridge 2908 rather than the stapler portion 900 discussed above. The operation of the multi-line staple cartridge 2908 is discussed in more detail below.

The staple applying assembly 2900 also includes a 4-bar hinge linkage 2910 connecting the tissue acquisition member 2906 to the first jaw 2902. The hinge linkage 2910 can include a base member 2912 and four linkage arms 2914, 2916, 2918, 2920. Each of the linkage arms 2914, 2916, 2918, 2920 can be pivotally connected at one end to opposing sides of the base member 2912 and pivotally connected at the other end to opposing sides of the tissue acquisition member 2906. As a result, there is no connection between the top surface of the first or second jaws and the bottom surface of the tissue acquisition member, as shown in other embodiments.

Figure 30:
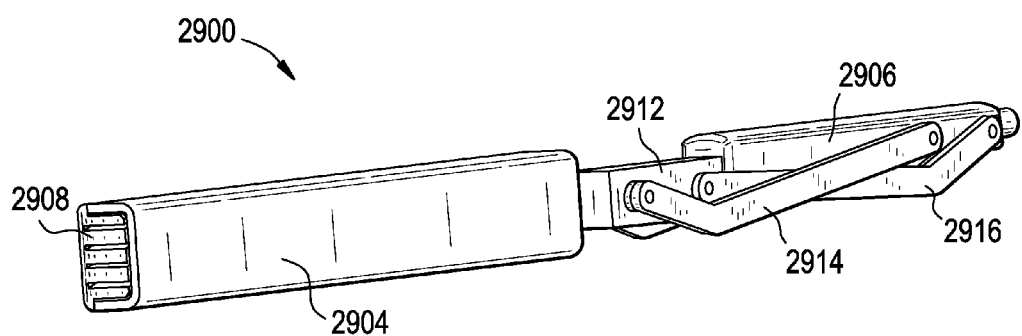
FIG. 30 is a side perspective view of the staple applying assembly of FIG. 29 showing the tissue acquisition member in a proximal storage position.

This particular configuration of the hinge linkage 2910 allows the tissue acquisition member 2906 to move through an increased range of motion. In particular, the tissue acquisition member 2906 can move from a first position adjacent to, and substantially between, the first and second jaws 2902, 2904 to a second position that is offset above the first and second jaws, similar to the embodiments discussed above. However, the tissue acquisition member 2910 can continue to move to a third position in which the tissue acquisition member is disposed proximal to the first and second jaws 2902, 2904, as shown in FIG. 30. Further, the tissue acquisition member 2906 can be in contact with a shaft of a surgical device (e.g., extension section 1304 discussed above) extending proximally from the staple applying assembly 2900.

As shown in FIG. 30, this proximal storage position can provide a reduced overall diameter of the surgical tool for introduction into a patient endoscopically. For example, in an exemplary embodiment, the rigid length of the staple applying assembly 2900 can be about 25 millimeters to about 80 millimeters in length, with a diameter of about 14 mm to about 20 mm.

The linkage 2910 can provide additional benefits as well. For example, the linkage 2910 can utilize linkage arms having bends and other shape features that allow the tissue acquisition member 2906 to be lowered beyond a plane defined by a superior surface of the first and second jaws 2902, 2904 or a shaft extending proximally from the staple applying assembly 2900. This can, for example, allow the tissue acquisition member 2906 to be lowered between the first and second jaws 2902, 2904 toward tissue when the jaws are in an open position. In addition, a shaft extending proximally from the staple applying assembly 2900 can include a feature, such as a recess, to seat the tissue acquisition member 2906 and thereby reduce the total diameter of the staple applying assembly 2900 as much as possible.

Another benefit of the linkage 2910 is that the increased range of motion can be utilized to form larger plications. For example, when the tissue acquisition member 2906 is raised above the first and second jaws to a maximum height, the linkage 2910 will be approximately halfway through its range of motion (i.e., roughly halfway between the orientations shown in FIGS. 29 and 30). If an operator desires to form an even larger plication, the tissue acquisition member 2906 can simply be retracted further, as if moving it toward the proximal low-profile insertion position. Because tissue is still attached to the tissue acquisition member via vacuum suction, a secondary tissue acquirer, or both, the tissue will continue to be drawn further through the first and second jaws 2902, 2904, thereby creating a larger plication.

Alternative Fastening Mechanisms

The stapler portion 900 described above is just one of a variety of fastening mechanisms that can be used to secure plications formed by a tissue acquisition member. The multi-line staple cartridge 2908 illustrated in FIGS. 29 and 30 is another embodiment of a fastener delivery mechanism of the present invention.

The multi-line staple cartridge 2908 has a generally rectangular body with four rows of staples that are aligned end-to-end parallel to a longitudinal axis of the cartridge. While four rows of staples are illustrated, the staple cartridge 2908 can include a different number of rows. The staple cartridge 2908 can also include a mechanism for ejecting the staples from the cartridge selectively.

Figure 31A:
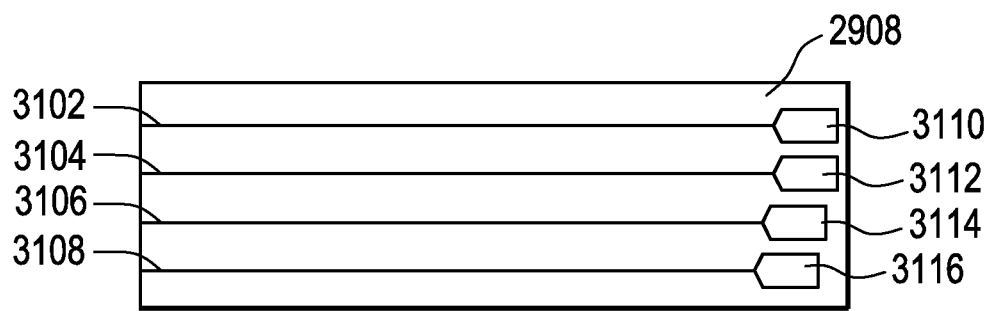
FIG. 31A is a top view of one embodiment of a multi-line staple cartridge.

FIG. 31A depicts a top view of the staple cartridge 2908 showing each of the four rows of staples 3102, 3104, 3106, 3108. Each staple row 3102, 3104, 3106, 3108 includes a wedge 3110, 3112, 3114, 3116 slidably disposed in the row. Each wedge 3110, 3112, 3114, 3116 can be configured to interface with and eject a staple from the row as the wedge slides along the row.

Figure 31B:
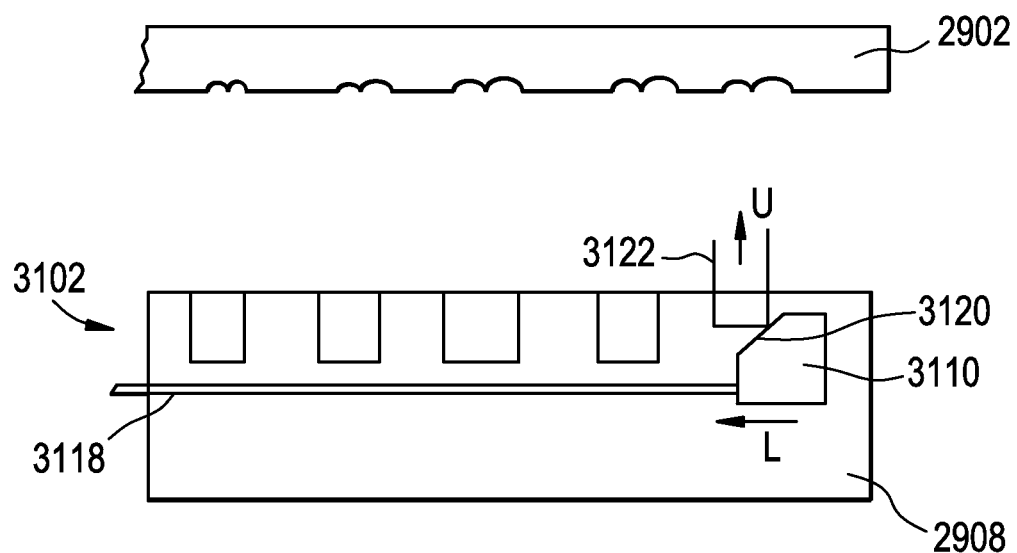
FIG. 31B is a side view of the multi-line staple cartridge of FIG. 31A.

The ejection mechanism is illustrated in FIG. 31B, which depicts the staple cartridge 2908 from the side view. As the figure illustrates, the wedge 3110 can be seated in the row 3102 that contains a plurality of staples. The wedge 3110 can also be connected to an actuating cable 3118 to control its position along the row of staples 3102. For example, an operator can tension the actuating cable 3118 to slide the wedge 3110 to the left in FIG. 31B (i.e., in the direction of the arrow L). The wedge 3110 can have a slanted surface 3120 that engages a first staple 3122 and ejects it from the staple cartridge 2908 toward, for example, the anvil jaw of the stapler 2902 (i.e., in the direction of the arrow U). After the first staple 3122 is ejected from the staple cartridge 2908, the operator can stop tensioning the actuating cable 3118 to cease ejecting staples, or continue to slide the wedge 3110 proximally (i.e., to the left in FIG. 31B) to subsequently eject one or more of the other staples in the row 3102.

Each staple row 3102, 3104, 3106, 3108 can have a similar configuration with its own wedge and actuating cable. Accordingly, the staple cartridge 2908 can provide four rows of staples wherein each row is selectively controllable using a control wire or actuating cable connected to the wedge slidably disposed in the row.

Figure 32A:
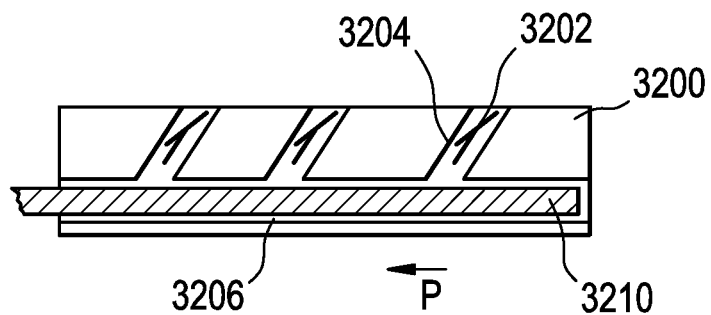
FIG. 32A is a side view of another embodiment of a multi-line staple cartridge.
Figure 32B:
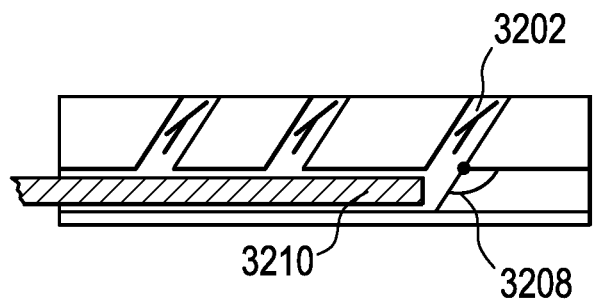
FIG. 32B is a side view of the multi-line staple cartridge of FIG. 32A showing an actuating member in a second position.
Figure 32C:
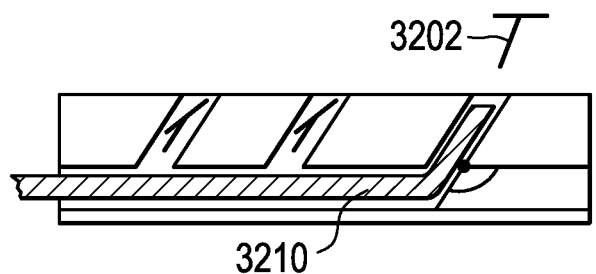
FIG. 32C is a side view of the multi-line staple cartridge of FIG. 32A showing an actuating member in a third position.

FIGS. 32A-C illustrate an alternative embodiment for sequentially ejecting fasteners from a row, such as the rows 3102, 3104, 3106, 3108 of the staple cartridge 2908. In this embodiment, a fastener cartridge 3200 includes one or more rows of fasteners 3202, where each fastener is disposed in a silo 3204 within the cartridge. Collapsible T-tags are illustrated in the figure, but it is possible to use staples or a variety of other fasteners as well. Each silo 3204 connects to a central row passage 3206 at its bottom end. Further, the row passage 3206 includes a swinging trap door 3208 mounted on the distal end of each silo 3204. In a loaded cartridge, as shown in FIG. 32A, each trap door is held in an open position by an actuating member 3210, which also forms the bottom surface of each silo 3204.

To eject a fastener, the actuating member 3210 can be drawn proximally (i.e., in the direction of arrow P) past a first silo 3204. Once the actuating member 3210 moves beyond the trap door 3208 of the silo, the door will swing shut to the position shown in FIG. 32B as a result of its biasing via, for example, a spring. The actuating member 3210 can then be advanced distally to eject the fastener. In particular, the actuating member 3210 will abut against the sloped surface of the trap door 3208 and be deflected upward into the silo 3204. The actuating member 3210 can then push the fastener out of the silo 3204 and into surrounding tissue, as shown in FIG. 32C. In order to function properly, the actuating member 3210 can be formed from a material that is flexible enough to permit deflection into a silo 3204 and also sufficiently incompressible to apply an ejection force to the fastener 3202.

To selectively deliver an additional fastener from a row of fasteners in a cartridge 3200, the actuating member 3210 can be retracted past the next-most proximal silo, and subsequently advanced distally to eject the fastener. Similar to the staple cartridge 2900, the cartridge 3200 can feature multiple rows of fasteners, each having their own actuating member 3210 so as to make each row of fasteners selectively controllable.

A number of variations on this fastener cartridge are possible. For example, the collapsible T-tag fasteners 3202 shown may be disposed within the central row passage 3206 or within the actuating member 3210.

Figure 33A:
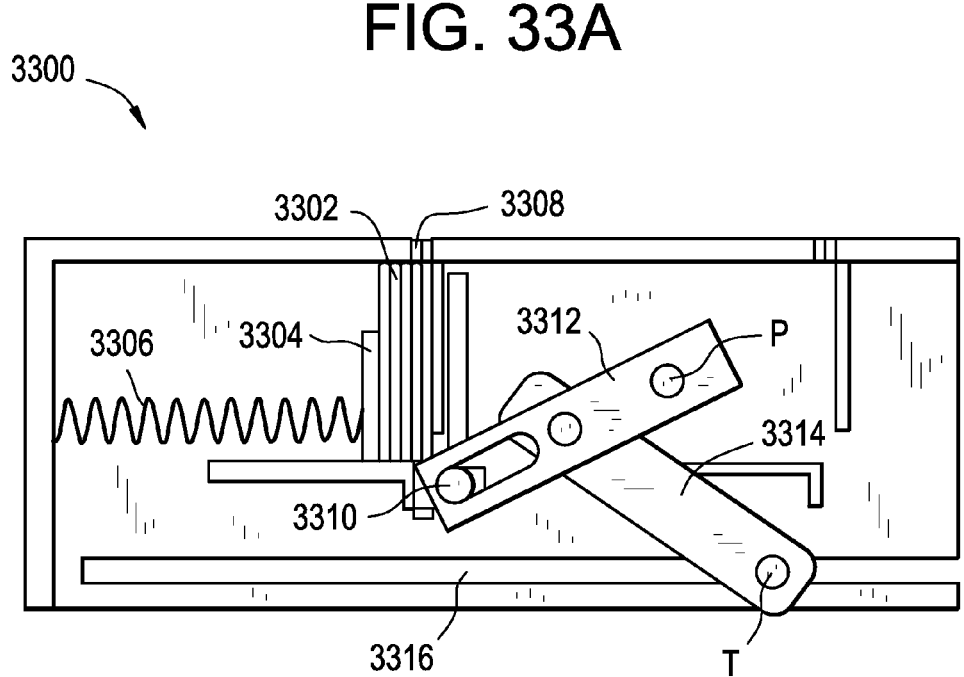
FIG. 33A is a side view of one embodiment of a staple firing mechanism for use in a staple applying assembly.
Figure 33B:
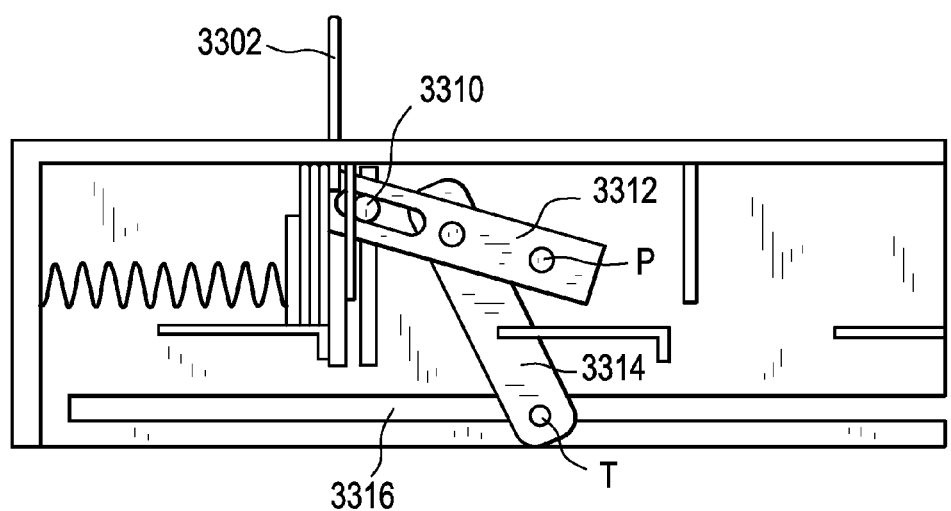
FIG. 33B is a side view of the staple firing mechanism of FIG. 33A showing the mechanism in a second position.

In other embodiments, devices are provided that are capable of simultaneously ejecting a plurality of staples from a stapling member. FIGS. 33A and 33B illustrate one embodiment of such a device. The figures depict one staple ejecting module 3300 that includes components similar to the stapler portion 900 and the staple former 902 discussed above. In particular, the module 3300 can be integrated into, for example, the second jaw 204 and can include a plurality of staples 3302, a staple pusher 3304, and a biasing element 3306 configured to press the staple pusher into the plurality of staples and urge them toward a slot 3308. A longitudinal axis of the slot 3308 can be offset at an angle from a longitudinal axis of the second jaw 204 and, in some embodiments, can be perpendicular to the longitudinal axis of the second jaw.

A firing linkage of the module 3300 can include a staple former 3310 slidably disposed in the slot 3308. The staple former 3310 can be pivotally connected to a forming link 3312. The forming link 3312 can be pivotally connected to, for example, the second jaw 204 at pin P. The forming link 3312 can also be pivotally connected to a firing link 3314 between pin P and staple former 3310. The firing link 3314 can, in turn, be pivotally connected to a firing pin T that can be slidably disposed within a slot 3316 that extends parallel to a longitudinal axis of the second jaw 204. The firing pin T can be connected to an actuating cable such that, as the actuating cable is pulled, the firing pin T translates within the slot 3316.

In particular, the pin T can move from a first position illustrated in FIG. 33A to a second position illustrated in FIG. 33B. As the pin T moves, its horizontal translation is converted into a vertical movement of the staple former 3310 by the firing link 3314 and the forming link 3312. As the staple former 3310 moves upward from the bottom of the slot 3308, it ejects a staple 3302 that was pushed into the slot 3308 by the staple pusher 3304.

FIGS. 33A and 33B illustrate only a single staple ejecting module 3300, however, a staple applying assembly may include more than one module 3300 along the length of, for example, the second jaw 204. By including a plurality of these modules along the length of a device and connecting each firing pin T to an actuating cable, a single actuation of the cable can be effective to eject a plurality of staples simultaneously.

Figure 34:
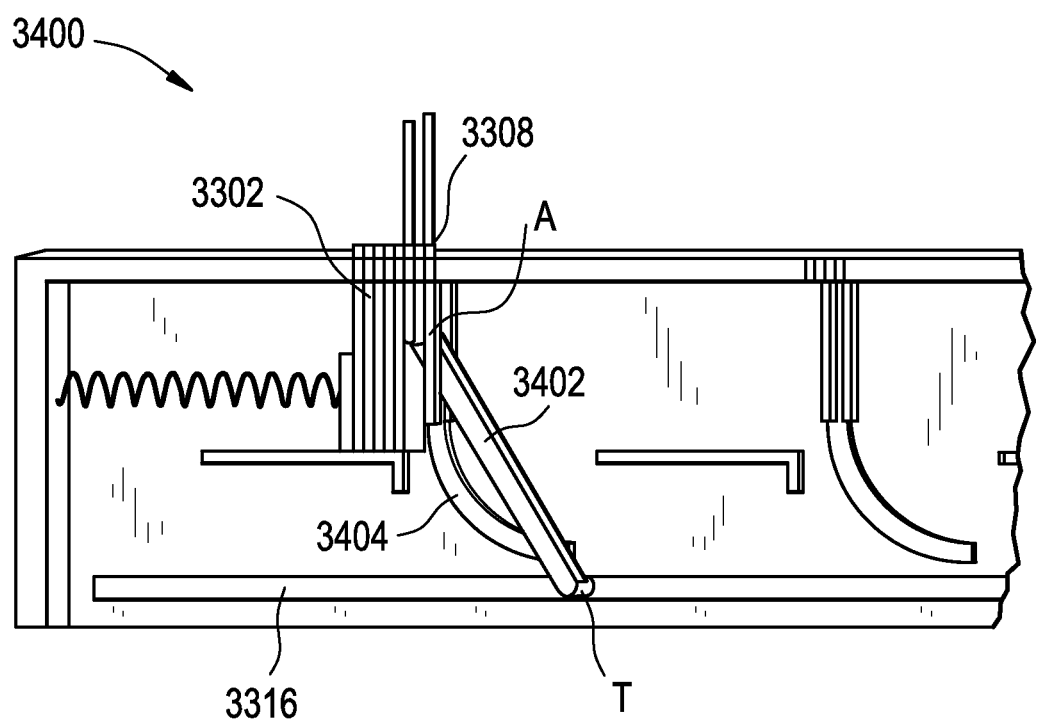
FIG. 34 is a side view of another embodiment of a staple firing mechanism for use in a staple applying assembly.

FIG. 34 illustrates another embodiment of a staple ejecting module 3400. Most of the components are similar, but there is only a single firing link 3402. The firing link 3402 is coupled at a first end to a pin A seated in a slot 3404 and coupled at a second end to the firing pin T that is seated in the slot 3316. As the pin T is translated in the slot 3316, the firing link 3402 causes a related motion of the pin A along the path of the slot 3304. The slot 3304 begins below the plurality of staples 3302 and curves upward toward the opening of the slot 3308. As the pin A travels toward the opening of the slot 3308, the firing link 3402 comes in contact with a staple 3302 in the slot 3308 and ejects the staple 3302 from the second jaw 204. In order to prevent the firing link 3402 from slipping on the staple 3302 or picking up multiple staples, the face of the firing link that interfaces with the staple can include one or more features to prevent such a slippage. These features can include, for example, a concave shape and a textured surface to aid in gripping the staple. As can be seen in the right-hand side of FIG. 34, a plurality of the described staple ejecting modules 3400 can be disposed along the length of, for example, the second jaw 204 of a staple applying assembly.

Figure 35:
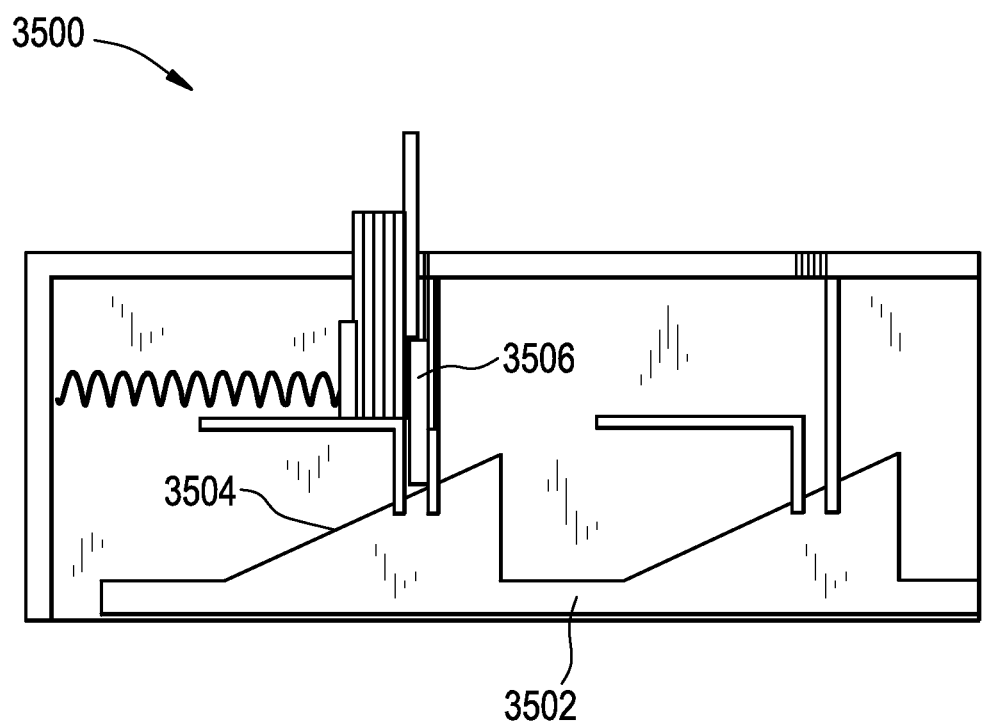
FIG. 35 is a side view of still another embodiment of a staple firing mechanism for use in a staple applying assembly.

FIG. 35 illustrates yet another embodiment of a staple ejecting module that can be replicated along the length of, for example, the second jaw 204 in order to simultaneously eject multiple staples. In this embodiment, the pivoting or sliding linkages of FIGS. 33A-34 are replaced by a rigid cam member 3502 that translates in a direction parallel to a longitudinal axis of the second jaw 204. The cam member 3502 includes a cam surface 3504 that interfaces with a staple former 3506. The staple former 3506 is slidably disposed in the slot 3308 and ejects a staple 3302 in a similar manner to staple former 3310 as the cam member 3502 urges the staple former farther upward.

Figure 36:
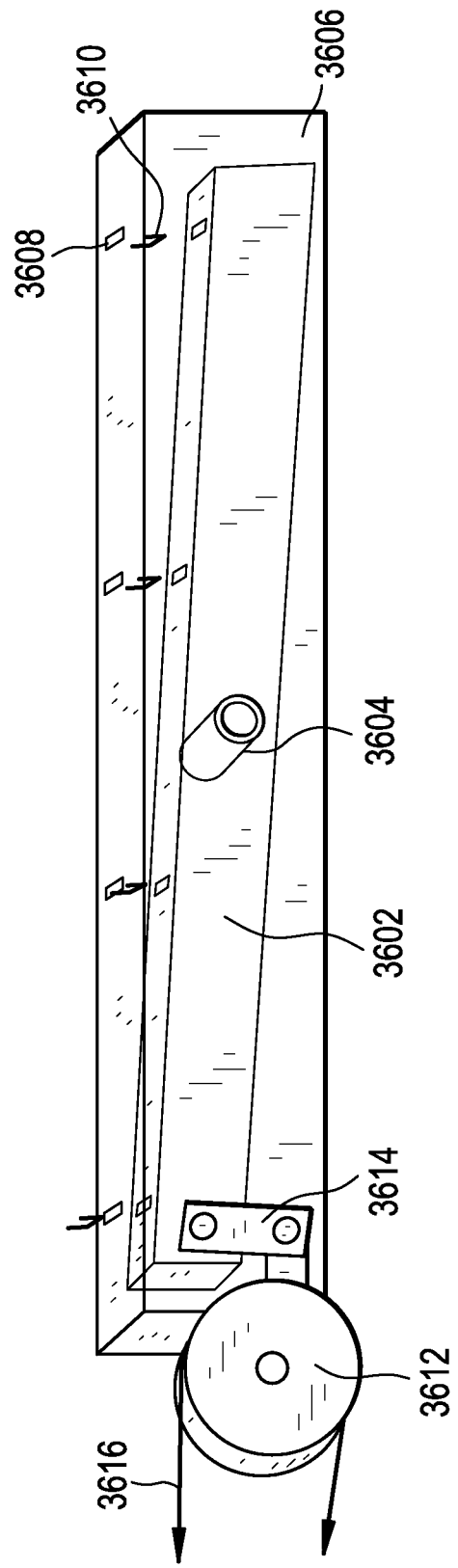
FIG. 36 is a side perspective view of another embodiment of a staple firing mechanism for use in a staple applying assembly.

In still another embodiment shown in FIG. 36, a pivoting staple former 3602 is used to simultaneously eject each of the staples located on opposing sides of a pivot point 3604. The second jaw 3606 in this embodiment includes a plurality of slots 3608 housing staples 3610. An elongate staple former that extends substantially the entire length of the second jaw 3606 is pivotally attached to the second jaw 3606 by the pin 3604. At a proximal end of the second jaw 3606, the staple former 3602 is pivotally coupled to a pulley wheel 3612 by a link 3614. An actuating cable 3616 can be used to rotate the pulley wheel 3612 clockwise or counterclockwise by tensioning opposing ends of the actuating cable.

To eject staples from each of the slots 3608 located distal to the pivot point 3604, the operator can rotate the pulley wheel 3612 in a clockwise direction. This action lowers the proximal end of the staple former 3602 and raises the distal end of the staple former, thereby ejecting the staples from the distal end slots 3608. Conversely, to eject staples from the slots 3608 located proximally to the pivot point 3604, the operator can rotate the pulley wheel 3612 in a counterclockwise direction, thereby raising the proximal end of the staple pusher 3602 and ejecting staples.

The above-disclosed embodiments are examples of mechanisms capable of firing multiple staples or other fasteners sequentially or simultaneously. It should be noted that there are a variety of other mechanisms for accomplishing this goal as well. These include, for example, the incorporation of a continuous feed linear stapler into the staple applying assembly to avoid having to remove the device for re-loading. All of these variations are considered within the scope of the present invention.

Methods of Use

The present invention also provides methods for creating and securing gastric plications. The methods of the present invention are generally, though not exclusively, characterized by positioning jaws of a stapling device parallel to a tissue surface, rather than perpendicular to it. A tissue acquisition member can then be used to draw tissue through the jaws to create a gastric plication.

Figure 37:
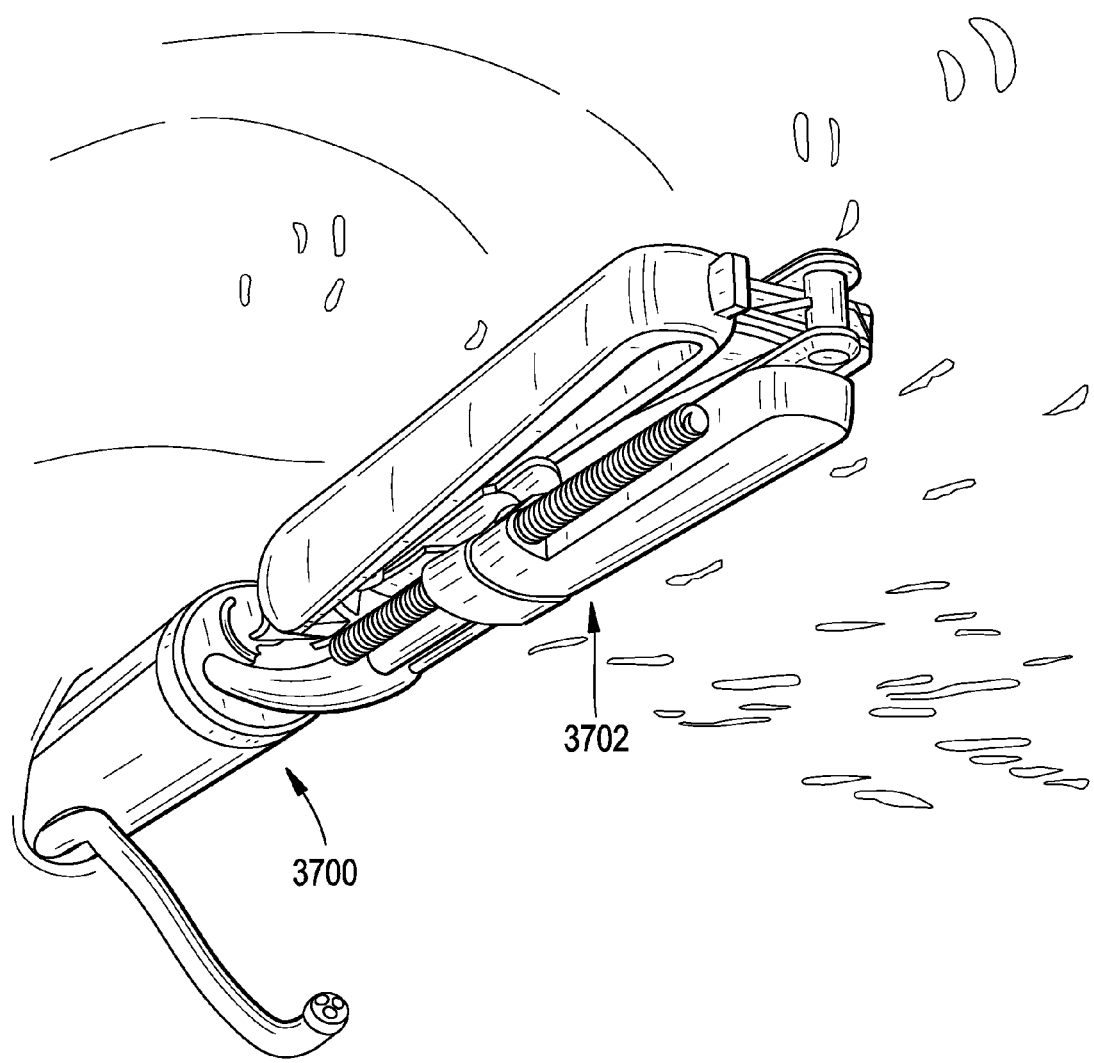
FIG. 37 illustrates a staple applying end effector approaching a tissue wall.

Several stages of an embodiment of a method of the present invention are illustrated in FIGS. 37-45. As shown in FIG. 37, a surgical device 3700 can be inserted into a patient's gastric cavity through the esophagus, and subsequently positioned along the stomach wall such that a longitudinal axis of the end effector is substantially parallel to an inner surface of the stomach wall. The surgical device 3700 can include a staple applying assembly 3702 according to any of the various embodiments discussed above.

Figure 38:
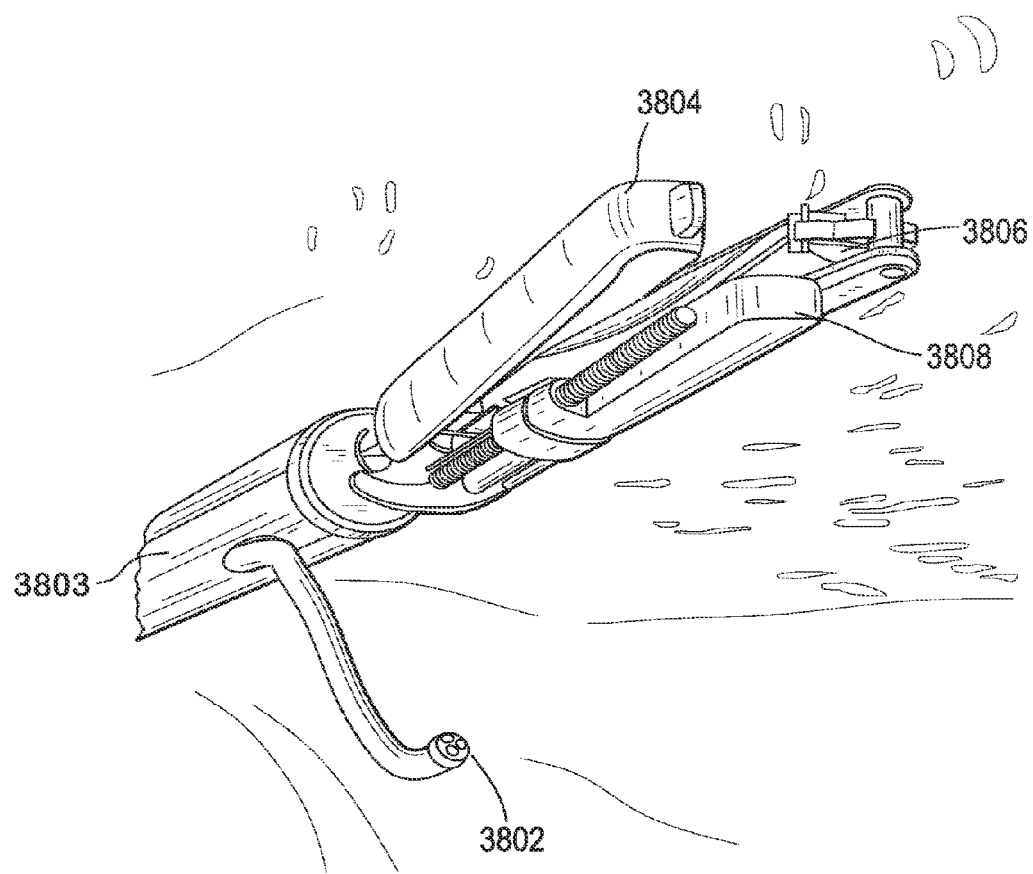
FIG. 38 illustrates the staple applying end effector of FIG. 37 in an open position.

Once in the gastric cavity, a viewing scope 3802 can be extended from an elongate shaft 3803 extending proximally from the staple applying assembly 3702, as shown in FIG. 38. After any necessary positional adjustment using the visual aid of the scope 3802, the first and second jaws 3804, 3806 can be moved to an open position in which they are configured to receive tissue. In addition, the tissue acquisition member 3808 can be further lowered, e.g., moved closer toward the jaws and the tissue on the opposite side of the jaws. In some embodiments, the tissue acquisition member can be moved into the space between the first and second jaws 3804, 3806, if so desired.

Figure 39:
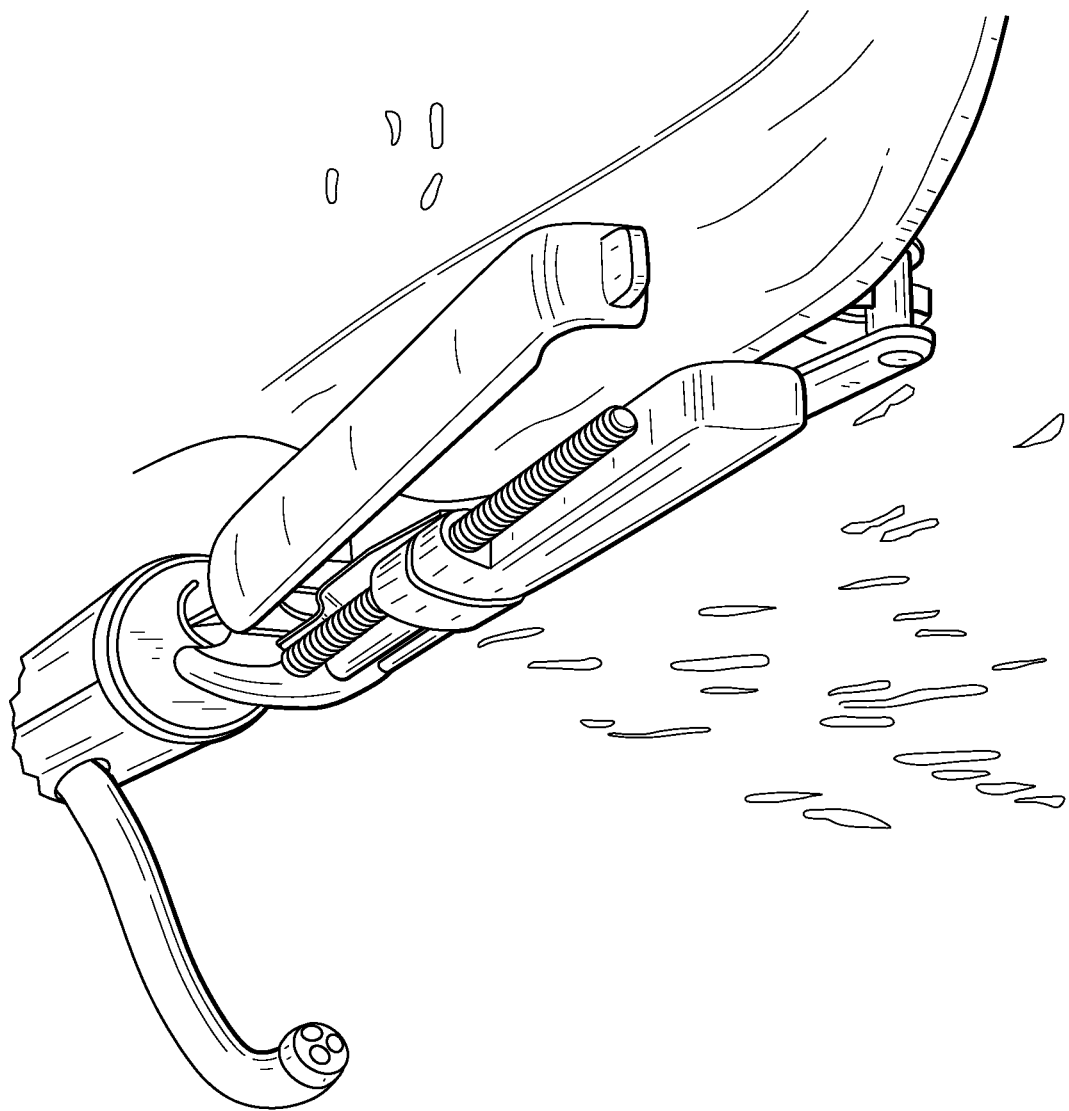
FIG. 39 illustrates the staple applying end effector of FIG. 37 receiving tissue between open first and second jaws.

As shown in FIG. 39, a vacuum source can be activated such that one or more vacuum ports on a lower surface of the tissue acquisition member 3808 draw tissue against the surface. Because the tissue acquisition member 3808 is located substantially between the first and second jaws 3804, 3806, the tissue drawn against the tissue acquisition member passes through the first and second jaws and begins to form a gastric plication, or fold. As mentioned above, in some embodiments the first and second jaws are configured to separate by 10 mm or less to prevent any undesired surrounding tissue from also being drawn through the first and second jaws. Alternatively, the jaws can be opened sufficiently to allow the vacuum pod to pass between and directly contact tissue. In such a circumstance, the jaws can be manually or automatically closed to a distance less than 10 mm once the vacuum pod is free of the region between the jaws.

Figure 40:
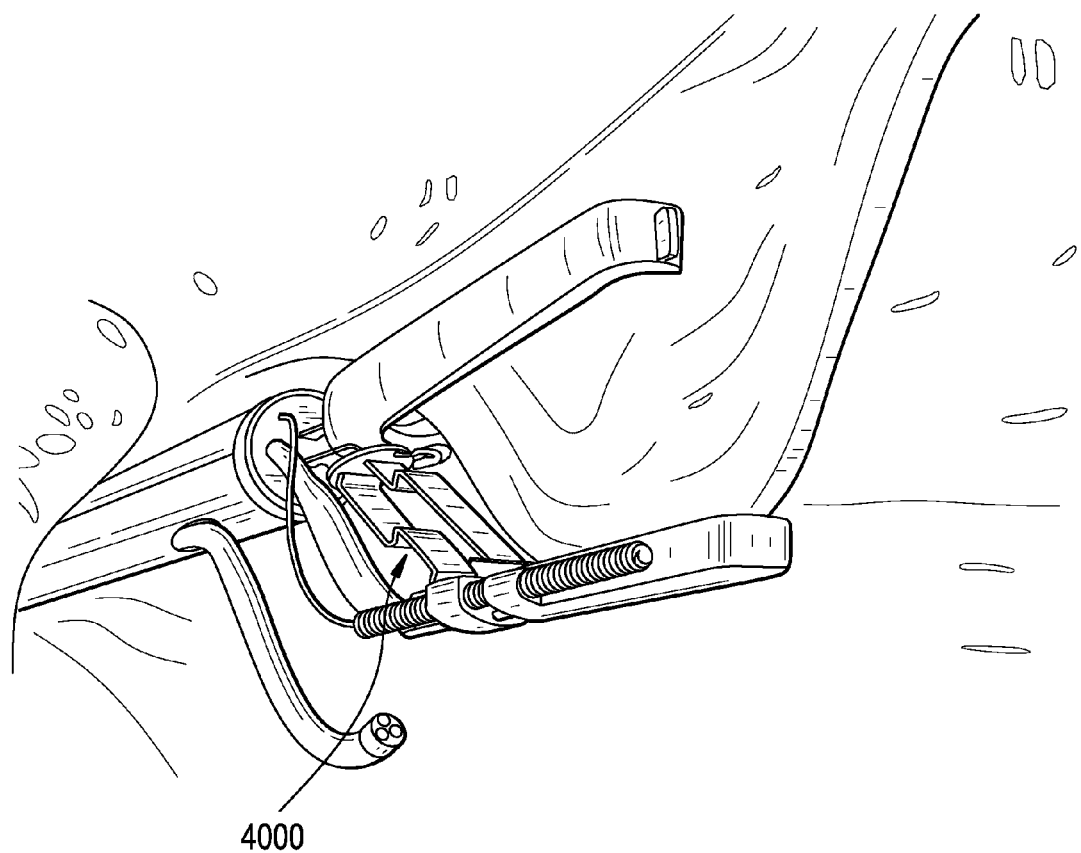
FIG. 40 illustrates the staple applying end effector of FIG. 37 securing a gastric fold with a fastener.

After drawing tissue against the tissue acquisition member 3702 by suction, any secondary tissue acquirer can be actuated to engage the tissue and help maintain its position as the tissue acquisition member is moved away from the first and second jaws 3804, 3806. The tissue acquisition member 3702 can then be actuated by, for example, tensioning a cable connected to the tissue acquisition member. This tensioning can cause the tissue acquisition member to both raise above (i.e., move farther away from) and translate longitudinally with respect to the first and second jaws 3804, 3806 via hinge linkage 4000, as shown in FIG. 40. This action causes additional tissue to be drawn through the first and second jaws 3804, 3806, thereby enlarging the size of the plication being formed.

Once the size of the plication has been properly set (which may be at a partially elevated position in the event multiple rows are intended), the first and second jaws can be moved to a closed position effective to engage the tissue disposed therebetween, as shown in FIG. 40. A firing mechanism can then be actuated by, for example, tensioning an actuating cable connected to the firing linkage of the second jaw 3806. The firing mechanism can be effective to eject a staple or other fastener from the second jaw 3806, through the tissue disposed between the first and second jaws, and into an anvil portion of the first jaw 3804.

Figure 41:
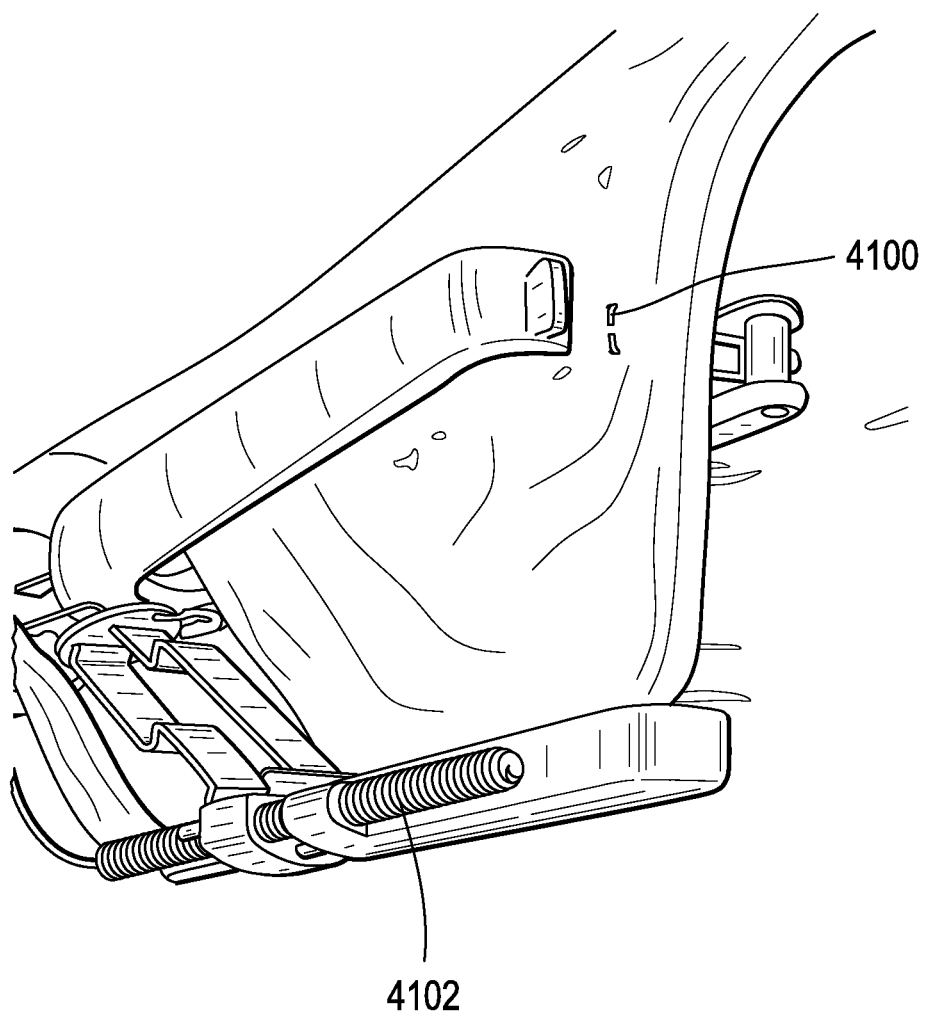
FIG. 41 illustrates the staple applying end effector of FIG. 37 translating a gastric fold to a first position.
Figure 42:
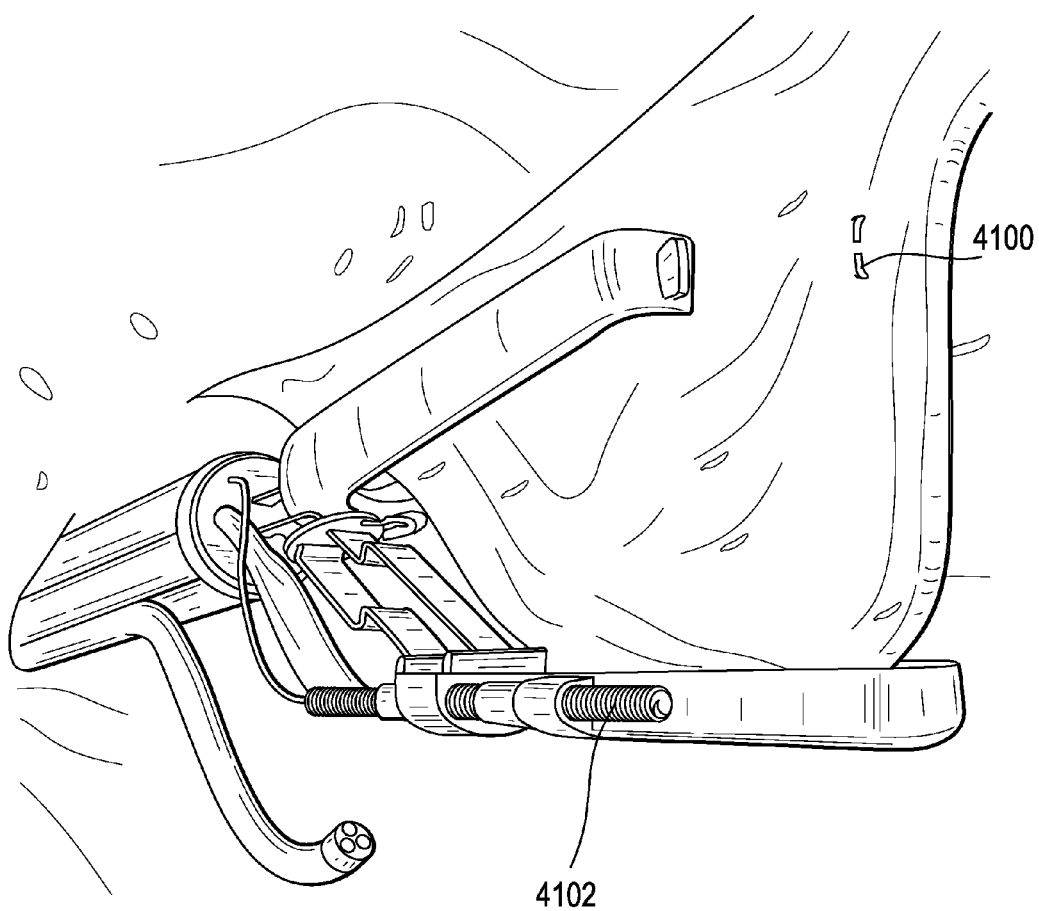
FIG. 42 illustrates the staple applying end effector of FIG. 37 applying a second fastener to a gastric fold.

The first and second jaws 3804, 3806 can then be moved back to the open position, revealing a first fastener 4100 securely holding the tissue layers of the plication together, as shown in FIG. 41. To secure additional fasteners in the plication, the tissue acquisition member 3702 can be translated longitudinally along its axis using, for example, a lead screw 4102 attached to the tissue acquisition member, as described above. FIG. 42 shows the tissue acquisition member 3702 translated distally from the position shown in FIG. 41. In some embodiments, the distance between successive fasteners is less than 2 cm. In other embodiments, the distance between successive fasteners is about 1 cm.

Figure 43:
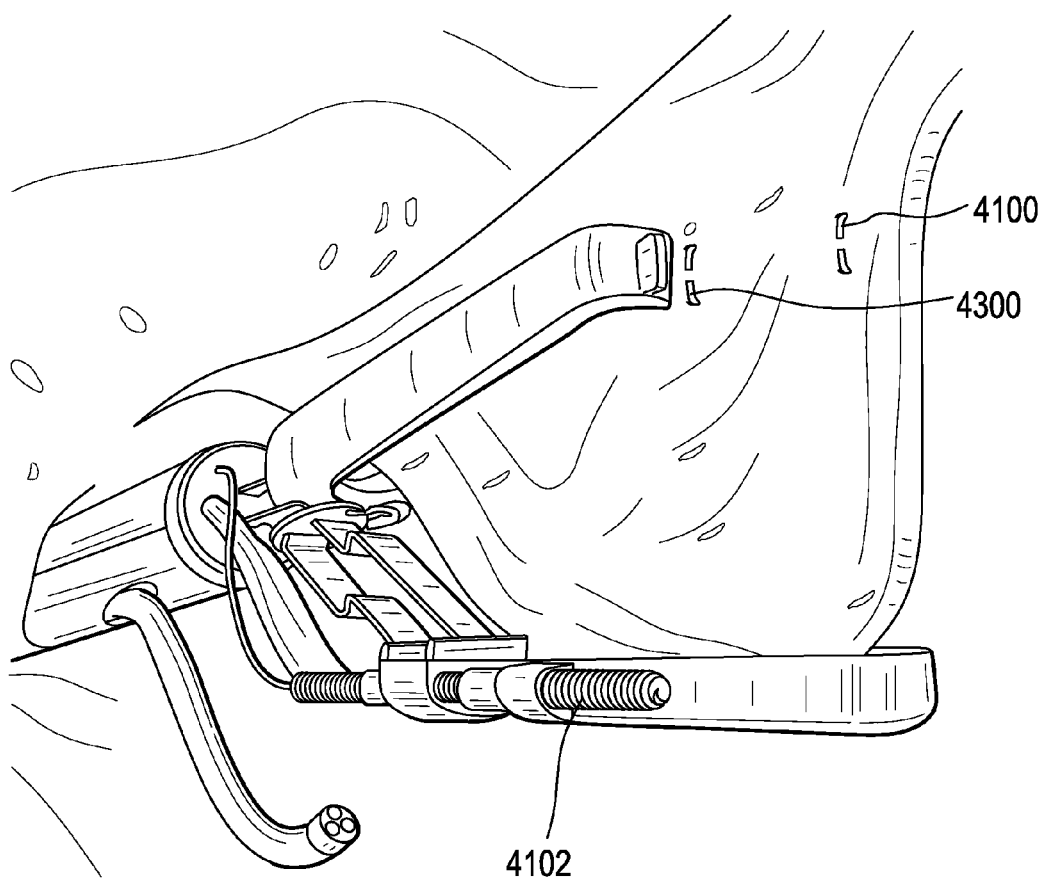
FIG. 43 illustrates the staple applying end effector of FIG. 37 translating a gastric fold to a second position.
Figure 44:
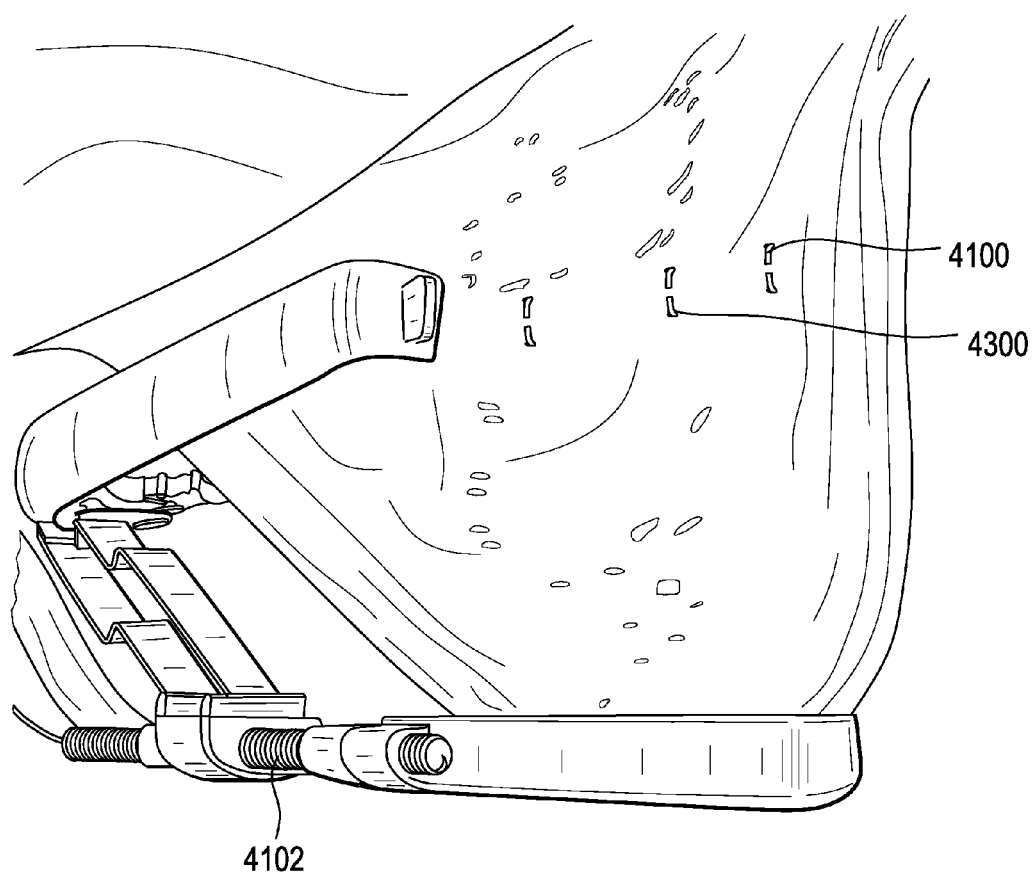
FIG. 44 illustrates the staple applying end effector of FIG. 37 translating a gastric fold to a third position.

The process above can be repeated to secure the plication with a second fastener 4300, as shown in FIG. 43, and can be further repeated until the tissue acquisition member reaches the distal end of the lead screw 4102, as shown in FIG. 44. At this point, if a second, parallel line of staples is necessary, the jaws can be moved to the open position, the tissue acquisition member can be translated back to its original proximal position on the lead screw 4100, and the height of the tissue acquisition member over the first and second jaws can be adjusted via the hinge linkage to position the tissue for the delivery of a second line of staples.

Figure 45:
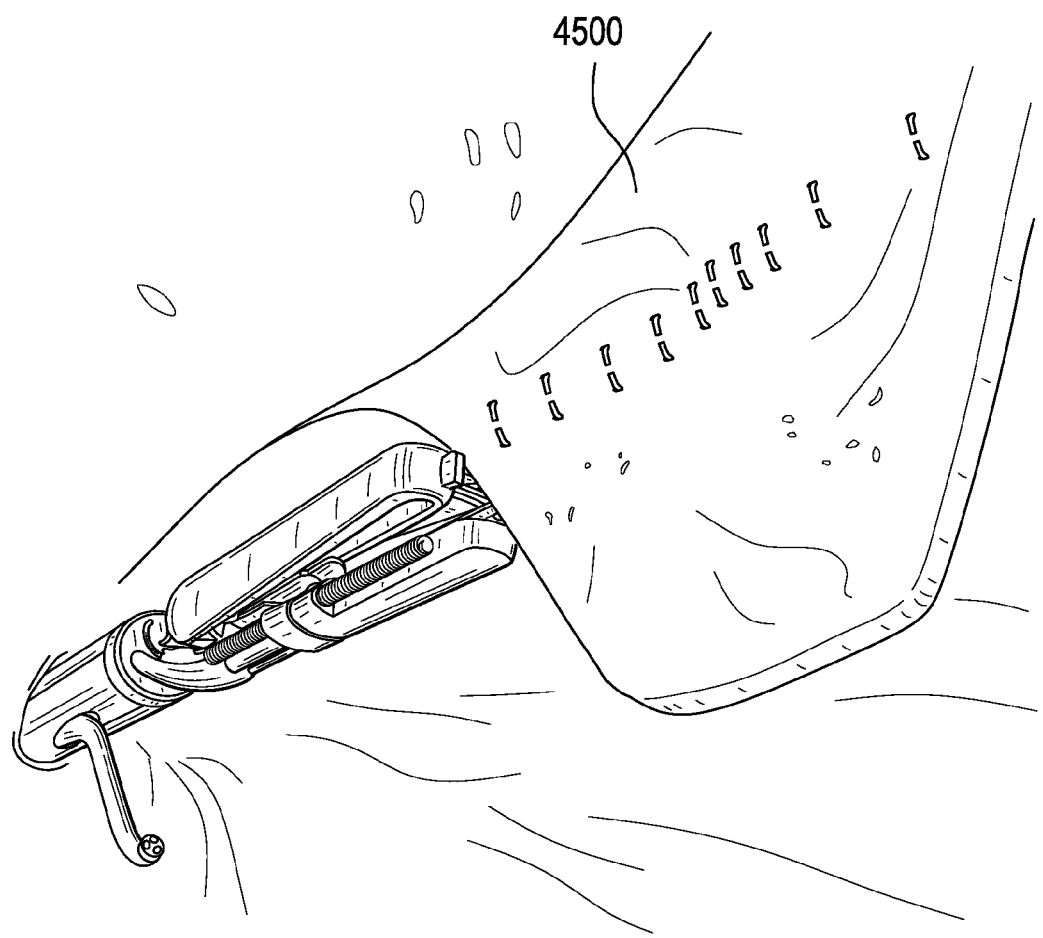
FIG. 45 illustrates a gastric fold secured by a line of staples.

If a second line of staples is not desired (suggesting, but not requiring, that the fold height was maximally created), the tissue acquisition member can release the tissue by disengaging any secondary tissue acquirers and deactivating the vacuum source connected to the tissue acquisition member. The end result can be a gastric fold secured by an even line of staples 4500, as shown in FIG. 45. To create an additional fold, the tissue acquisition member can be repositioned and the process started anew.

The methods disclosed above demonstrate how to use a device of the present invention to create and secure a gastric plication. However, the present invention also contemplates other methods of plication placement within the gastric cavity. For example, some data has shown that reduction of gastric volume through invagination of the greater curvature of the stomach has yielded significantly larger excess weight loss percentage than invagination of the lesser curvature.

Accordingly, in another exemplary method, one or more gastric plications can be formed on an anterior or posterior wall of the greater curvature of the stomach. An exemplary method for forming a plication is illustrated in FIGS. 46A-C. As shown in FIG. 46A, a device, such as device 4600 according to the present invention, can be inserted through a patient's esophagus 4602 and into the stomach cavity 4604. The device can then be articulated using, for example, the articulating joints described above, to access the anterior or posterior wall of the stomach near or within the fundus, as shown in FIG. 46B. Finally, a plication can be created and secured using, for example, the method described above. This leaves a secured gastric plication, as shown externally in FIG. 46C.

To create additional plications, the end effector staple applying assembly can be articulated from the position of "Fold A" shown in FIG. 47A to a second position labeled "Fold B." The above process can then be repeated to create and secure a second plication. If necessary, the end effector can again be articulated from the position of "Fold B" to a third position labeled "Fold C." Additional folds can be made as necessary, forming a fan-shaped pattern. After forming and securing all plications, the end effector can be retracted back out of the gastric cavity through the esophagus, leaving secured plications such as those shown in FIG. 47C.

The multiple plications discussed above can be formed in a clockwise or counterclockwise direction (i.e., moving from Fold A to Fold C, or Fold C to Fold A). In addition, plications can be formed on both the anterior and posterior walls of the greater curvature of the stomach. In forming plications on both walls, the methods of the present invention can include forming all plications on one wall before the other, or alternating between the two. In addition, plications can be formed on both walls in a particular section of the stomach before alternately or otherwise forming plications in other sections of the stomach. Further, plications can be formed in any of a proximal or a distal direction. For example, plications can be formed on both the posterior and anterior walls in or near the fundus before forming plications on alternate walls in a distal to proximal direction in other areas of the stomach. Still further, the respective folds created on the anterior and posterior walls of the stomach are not attached to each other. These methods can provide the benefit of limiting the impact of a decreasing working space as the multiple plications are formed and secured.

Figure 48A:
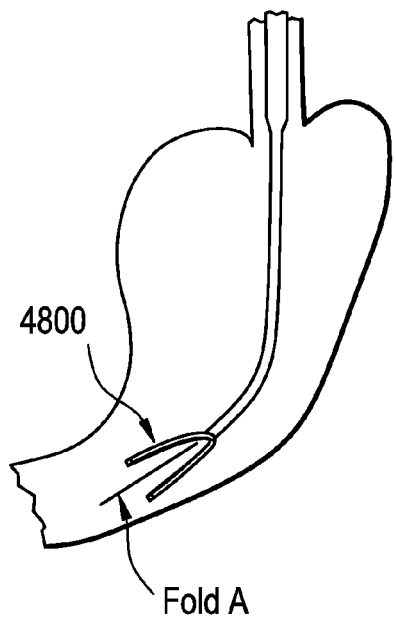
FIG. 48A illustrates another exemplary method of positioning of a staple applying assembly within a gastric cavity.
Figure 48B:
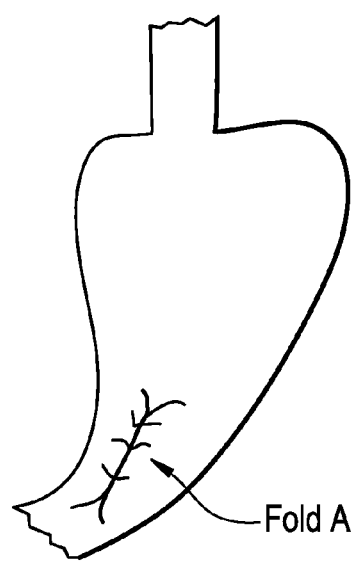
FIG. 48B illustrates an exemplary plication created in the lower region of the gastric cavity.

In another embodiment, multiple plications can be formed in an end-to-end fashion to create a single extended plication, rather than the fan-shaped pattern described above. To do so, a staple applying assembly 4800 according to the teachings of the invention can be inserted into a patient's stomach through the esophagus. Once in the stomach, the staple applying assembly 4800 can be positioned along the anterior wall of the stomach near or within the antrum, as shown in FIG. 48A. The staple applying assembly can be actuated according to any of the methods described above to form and secure a first gastric plication (labeled "Fold A"), shown externally in FIG. 48B.

Figure 49A:
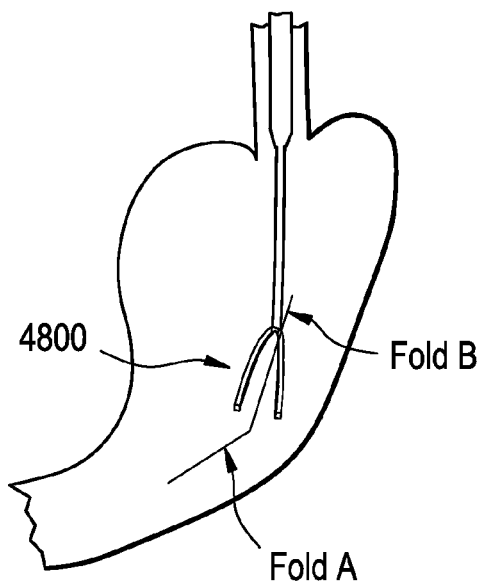
FIG. 49A illustrates an exemplary method of forming a second plication by extending from an end point of the plication shown in FIG. 48B.
Figure 49B:
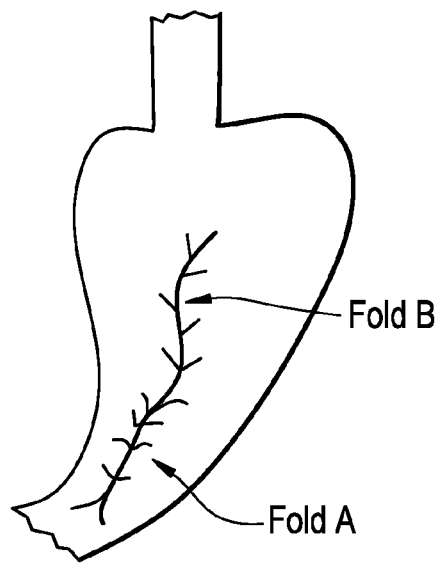
FIG. 49B illustrates a linear pattern formed from two plications.

Following formation of the first plication, the staple applying assembly 4800 can be retracted toward the esophagus as shown in FIG. 49A. Once the staple applying assembly is in a position to create a gastric plication that extends from the first gastric plication (labeled "Fold A"), the assembly 4800 can be actuated to create a second gastric plication (labeled "Fold B"), which is shown externally in FIG. 49B.

Figure 50A:
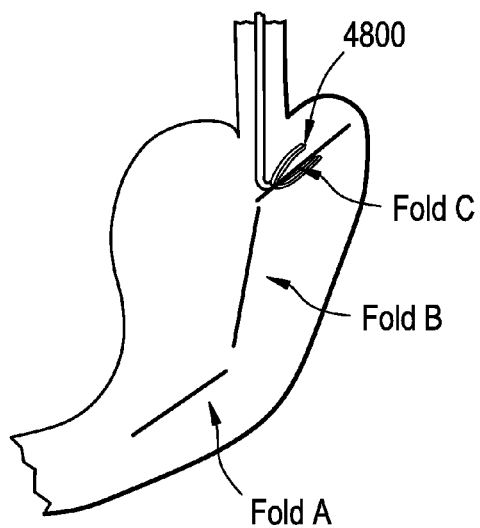
FIG. 50A illustrates an exemplary method of forming a third plication off the plications shown in FIG. 49A.
Figure 50B:
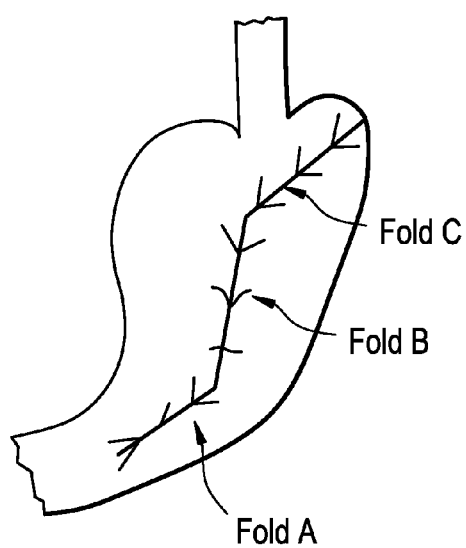
FIG. 50B illustrates a linear pattern formed from three plications.

The above process can be repeated again to create a third gastric plication (labeled "Fold C"), as shown in FIGS. 50A and 50B. Depending on the size (e.g., length) of the stapling jaws of the staple applying assembly 4800, the process may be repeated more or fewer times in order to create a desired number of gastric plications.

Figure 50C:
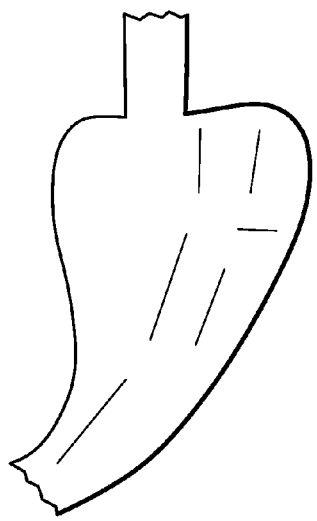
FIG. 50C illustrates an exemplary combination of the various plication patters shown in FIGS. 46A-50B

Similarly to the methods of forming plications in a fan-shaped pattern described above, the above methods contemplate forming all plications on an anterior wall of the stomach followed by forming all plications on a posterior wall, or alternately forming plications on the anterior wall and the posterior wall. Further, plications may be formed in both walls of one section of a cavity before forming plications alternately or in another manner in another section of the cavity. In addition, the plications formed on the anterior wall are not attached to those on the posterior wall of the stomach. Still further, the plications can be formed in a distal to proximal order, as shown in the figures, or in a proximal to distal order (i.e., moving from Fold C to Fold A). Following the formation of the final plication, the staple applying assembly can be removed from the stomach via the esophagus. One skilled in the art will appreciate that a combination of the embodiments described above may be used (e.g., first forming a plication in or near the fundus, and then forming a plication in a distal to proximal order, or first forming at least one plication in the form of a fan and then forming at least one plication in the form of a line), as shown in FIG. 50C.

In one exemplary method for gastric volume reduction, a surgical device of the present invention can be inserted into the gastric cavity via a patient's esophagus. An end effector of the gastric device can be retroflexed or articulated using, for example, articulating joints, to access the fundus region of the stomach (as shown in FIG. 50A). The end effector can then be utilized to create and secure a plication on at least one of the anterior and posterior inner surfaces of the fundus (e.g., Fold C of FIG. 50A). In an exemplary embodiment, folds are formed in both the anterior and posterior inner surfaces.

The formation of one or more folds in the fundus can significantly reduce the capacity of that region of the stomach, making it difficult to un-articulate the end effector, i.e., return the end effector to its original position in which it is substantially longitudinally aligned with at least a distal portion of the insertion shaft to which the end effector is attached. Accordingly, in some embodiments, it can be desirable to form folds in the fundus prior to forming any folds in the antrum so as to allow the surgical device to be extended distally toward the antrum of the stomach and to be un-articulated once the end effector is clear of the constricted fundus. In some embodiments, the end effector can then be extended into the antrum of the stomach without articulation (or with a lesser amount of articulation) and utilized to form a plurality of plications on at least one of the anterior and posterior inner surfaces of the stomach (e.g., Folds A and B of FIG. 50A). In an exemplary embodiment, the end effector is un-articulated and a series of folds are formed along each of the anterior and posterior walls.

Forming a plurality of plications in the stomach can be accomplished in a variety of manners. For example, all plications can be formed on one of the anterior or posterior surfaces of the stomach before forming plications on the other surface. In other embodiments, plications can be formed alternately on the anterior and posterior surfaces. In addition, plications can be formed in any of a proximal and a distal direction along the surfaces. For example, after forming plications in the fundus and extending the end effector into the antrum of the stomach, the plurality of plications can be formed in a distal-to-proximal direction along at least one of the anterior and posterior surfaces of the stomach (e.g., forming Fold A and then Fold B of FIG. 50A). In other embodiments, folds can be created in a proximal-to-distal direction on one surface (e.g., the anterior surface) and a distal-to-proximal direction on the other surface (e.g., the posterior surface), or vice versa. There are a number of variations in the order and direction in which plications can be formed in the cavity, all of which are considered within the scope of the present invention.

The above methods can be utilized to avoid complications resulting from the reductions in cavity capacity that occur as plications are formed. For example, in certain embodiments, forming all plications in the fundus region first can be advantageous because the unrestricted volume in the remainder of the stomach cavity can be used to accommodate movement of the end effector as any articulation necessary to reach the fundus is released. After releasing the articulation of the end effector, plications can be formed in the remainder of the stomach cavity in a distal-to-proximal direction (i.e., from the lower antrum region toward the esophagus). This pattern effectively retracts the end effector out of the stomach as the plications are formed.

Other Embodiments

Disclosed below are still additional embodiments of the present invention that provide variations over the embodiments discussed above. These embodiments, as well as others that may be apparent to one of ordinary skill in the art, are considered to be within the scope of the present invention.

Reciprocating Tissue Feeders

Figure 51A:
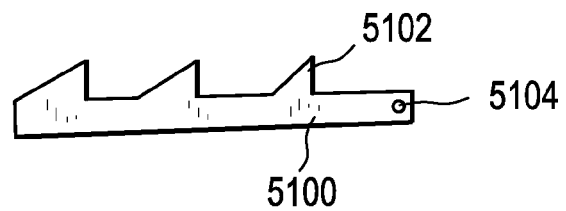
FIG. 51A is a side view of an embodiment of a reciprocating tissue feeder.
Figure 51B:
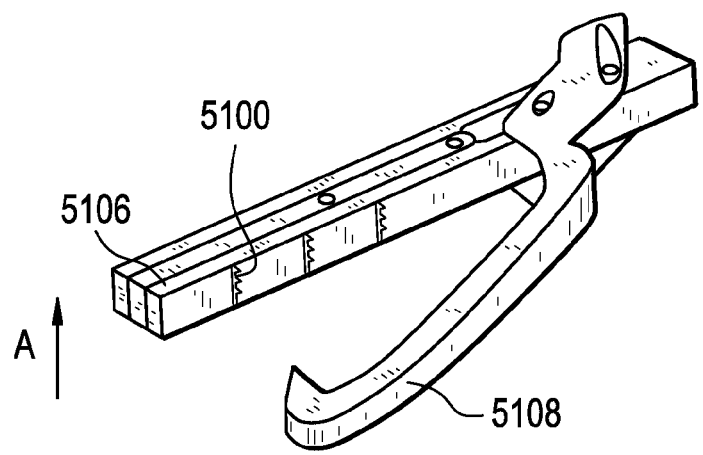
FIG. 51B is a front perspective view of an embodiment of a staple applying assembly including one or more reciprocating tissue feeders.
Figure 51C:
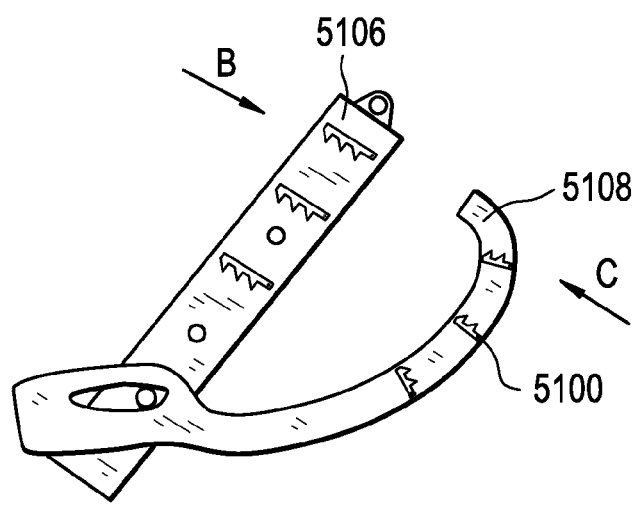
FIG. 51C is a bottom view of another embodiment of a staple applying assembly including one or more reciprocating tissue feeders.

FIGS. 51A-C illustrate one embodiment of a reciprocating tissue feeder that can be used in conjunction with the devices described above to aid in drawing tissue through, for example, a set of stapling jaws. As shown in FIG. 51A, the reciprocating tissue feeder can include an elongate member 5100 having one or more unidirectional protrusions 5102 that are configured to engage tissue when moved in one direction and slip past tissue when moved in an opposing direction. The elongate member 5100 can also feature a through-bore 5104 or other attachment feature that allows the elongate member 5100 to be coupled to an actuator.

An embodiment of a stapling member having one or more reciprocating tissue feeders is shown in FIG. 51B. As shown in the figure, the stapling member includes first and second jaws 5106, 5108. The surface of the second jaw 5106 that opposes the first jaw 5108 can include one or more of the reciprocating tissue feeders 5100. Each feeder 5100 can be coupled to an actuator, such as a small linear actuator, configured to alternately translate the feeder 5100 along its longitudinal axis. Provided the feeder 5100 is oriented such that the tissue engaging portions of its unidirectional protrusions 5102 face in the direction of desired motion (e.g., the upward direction illustrated by arrow A), the alternating motion of the feeders 5100 can aid a tissue acquisition member (not shown) in drawing tissue through the jaws. It should be noted that the surface of the first jaw 5108 that opposes the second jaw 5106 can have one or more tissue feeders 5100 disposed thereon as well, though these are blocked from view in the figure.

One or more of the reciprocating tissue feeders 5100 can also be placed on a bottom surface of the stapling jaws 5106, 5108, as shown in FIG. 51C. In this embodiment, the reciprocating tissue feeders 5100 can aid in gathering tissue surrounding the stapling jaws and bringing it toward the jaws to assist a tissue acquisition member (not shown) in drawing tissue through the jaws. The feeders 5100 on the second jaw 5106 can be configured such that reciprocal motion drives tissue in the direction of arrow B (i.e., the tissue engaging faces of protrusions 5102 on feeders 5100 face in the direction of arrow B). Tissue feeders 5100 disposed on the bottom surface of the first jaw 5108 can be configured to drive tissue in an opposing direction illustrated by arrow C. This converging motion helps gather surrounding tissue such that a tissue acquisition member can more easily draw the tissue through the jaws 5106, 5108.

It should be noted that other embodiments of the reciprocating tissue feeder 5100 are also possible. For example, a reciprocating belt (e.g., similar to a conveyer belt) having affixed thereto one or more unidirectional protrusions similar to protrusions 5102 can be incorporated into one or more surfaces of stapling jaws to aid in drawing tissue between the jaws. For example, a reciprocating belt could be configured to run substantially the entire length of a stapling jaw, or one or more belts could be located at particular locations along a surface of the jaw. Such a belt could be configured to move forward and back alternately, or to run in a continuous loop such that any protrusions are prevented from engaging tissue (e.g., by being contained within the body of a stapling jaw) during the return stroke.

Alternative Tissue Acquisition Members

There are a variety of mechanisms suitable for grasping a tissue wall and drawing a portion of the tissue wall in a direction so as to create a fold in the tissue wall. Several exemplary embodiments are discussed below. These embodiments can be utilized in conjunction with, or in place of, the tissue acquisition members discussed above.

Mechanical Grasper

Figure 52A:
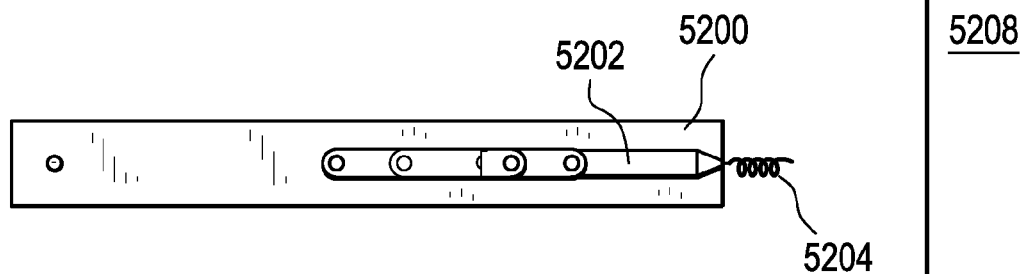
FIG. 52A is a side view of one embodiment of a staple applying assembly including a mechanical grasper as a tissue acquisition member.

In certain embodiments, a mechanical grasper can be utilized in place of vacuum suction in a tissue acquisition member. FIG. 52A illustrates a side view of a stapling member that includes a set of stapling jaws 5200 and a tissue acquisition member 5202 coupled thereto and disposed to one side of another of the jaws 5200. At the distal tip of the tissue acquisition member 5202 is a mechanical grasper 5204 that is configured to extend beyond a distal end of the jaws 5200. The mechanical grasper can have a variety of shapes and features and, in some embodiments, can be a corkscrew-shaped member configured to engage a tissue wall. At its proximal end, the tissue acquisition member 5202 can be coupled to the jaws 5200 via, for example, a two bar hinge linkage 5206, similar to the hinge linkages discussed above.

Figure 52B:
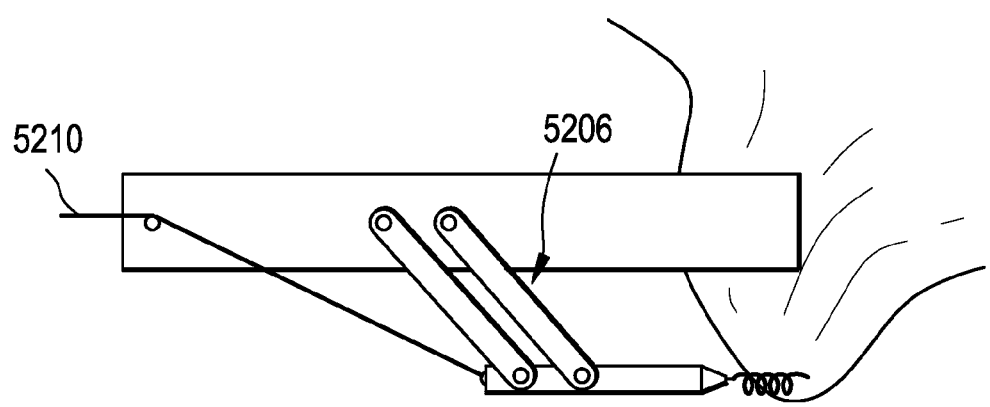
FIG. 52B is a side view of the staple applying assembly of FIG. 52A in a second position.

In operation, the device can be advanced to a tissue wall 5208 and grasper 5204 can be used to engage the tissue wall. This can be done, for example, by rotating the grasper 5204 to drive it into tissue. Next, an actuating cable 5210 can be tensioned to raise the tissue acquisition member 5202 above the jaws 5200 such that tissue is drawn into a space between the jaws 5200, as shown in FIG. 52B. The jaws 5200 can then be actuated according to the teachings of the invention to secure a plication using a staple or other fastener. Multiple fasteners could be used by, for example, opening the jaws and raising the tissue acquisition member 5202 more in order to further draw tissue through the jaws 5200.

Figure 53A:
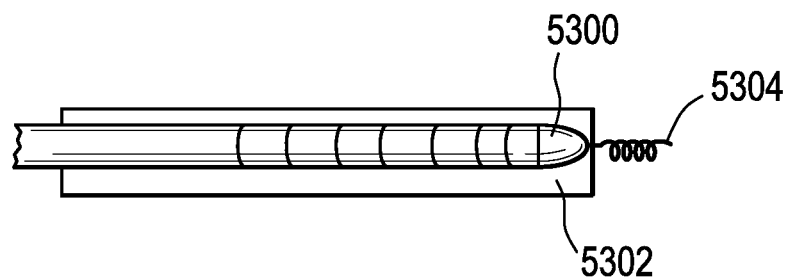
FIG. 53A is a side view of another embodiment of a staple applying assembly including a mechanical grasper as a tissue acquisition member.
Figure 53B:
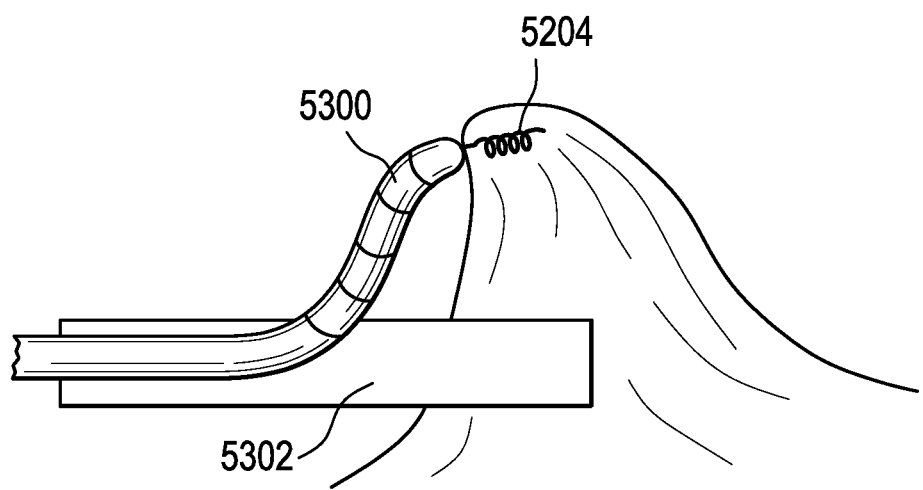
FIG. 53B is a side view of the staple applying assembly of FIG. 53A in a second position.

In another embodiment illustrated in FIGS. 53A and 53B, an articulating tissue acquisition member 5300 can be used in place of the hinge linkage 5206 to draw tissue through a set of stapling jaws 5302. The articulating member 5300 can be located between the two stapling jaws, to the side of the two jaws, or adjacent to an upper surface of the jaws 5302.

The jaws 5302 can be positioned near a tissue wall surface such that a longitudinal axis of the device is either perpendicular, parallel, or at another intermediary angle to the tissue wall surface. The tissue acquisition member 5300 can then be articulated to allow a mechanical grasper 5304 at a distal end thereof to engage tissue. Tensioning of internal control wires can cause the articulation of the tissue acquisition member 5300, similar to the articulating joints described above.

After the mechanical grasper 5304 has engaged tissue, the articulating tissue acquisition member 5300 can be moved into the position shown in FIG. 53B, thereby drawing tissue into the space between jaws 5302. Jaws 5302 can then be actuated according to the teachings of the invention to secure the plication created by the articulating tissue acquisition member 5300.

Deflecting Member

Figure 54A:
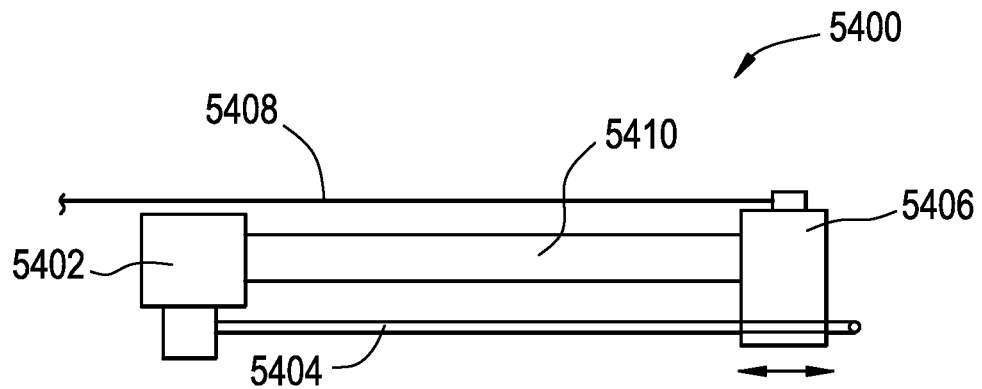
FIG. 54A is a top view of one embodiment of a tissue acquisition member including a deflecting member.

In still another embodiment, the deflection of a member under compression can be used to draw tissue away from a tissue wall surface to form a gastric plication. As shown in the top view of FIG. 54A, a tissue acquisition member 5400 can include a proximal base 5402 that can be fixedly attached to, for example, an upper surface of a first jaw of a set of stapling jaws (not shown). Coupled to the proximal base 5402 can be a rigid rail 5404 extending distally parallel to a longitudinal axis of, for example, a set of stapling jaws. A distal base 5406 can be located distal to the proximal base 5402 and slidably coupled to the rail 5404. An actuating cable 5408 can extend from the distal base 5406 to allow an operator to draw the distal base 5406 toward the proximal base 5402 along the rigid rail 5404. Finally, a resilient flexible member 5410 can be coupled to and disposed between the proximal base 5402 and the distal base 5406. In some embodiments, the coupling can be permit pivoting between the member 5410 and each of the bases 5402, 5406.

Figure 54B:
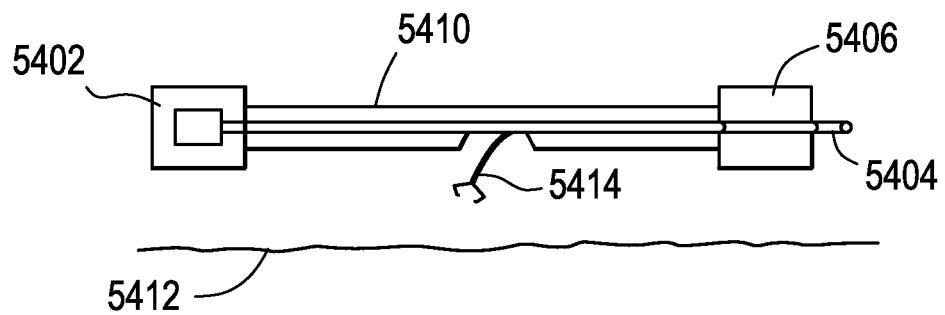
FIG. 54B is a side view of the tissue acquisition member of FIG. 54A in a first position.

In use, the tissue acquisition member 5400 can be positioned parallel to a tissue wall surface 5412 as shown in FIG. 54B. A grasper element 5414 can extend from an inner lumen in the member 5410 through an opening in an outer sidewall thereof. The grasper can include any number of mechanical elements configured to engage tissue, such as a corkscrew or a small set of grasping jaws, as shown in the figure. The grasper element 5414 can engage tissue and draw it against the member 5410 as the grasper element 5414 is retracted back into the inner lumen of the member.

Figure 54C:
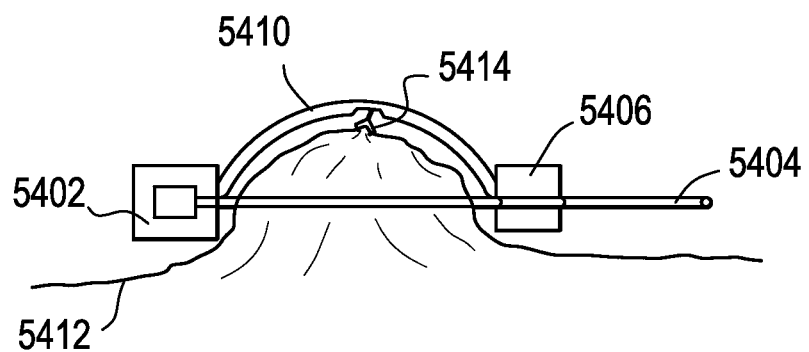
FIG. 54C is a side view of the tissue acquisition member of FIG. 54A in a second position.

Once tissue has been drawn against the member 5410, the actuating cable 5408 can be tensioned such that the distal base 5406 slides proximally along the rail 5404. The movement of the distal base 5406 can cause the resilient flexible member 5410 to deflect as shown in FIG. 54C. As a result of the fact that tissue has been drawn against the member 5410 by the grasper 5414, the tissue can be pulled away from the tissue wall surface 5412 as the member deflects further. If, for example, the tissue acquisition member 5400 is mounted on an upper surface of a set of stapling jaws, the tissue can be drawn up through the jaws as it rises, forming a gastric plication that can be secured using the stapling jaws, as described above.

Dual Supporting Arms

Figure 55A:
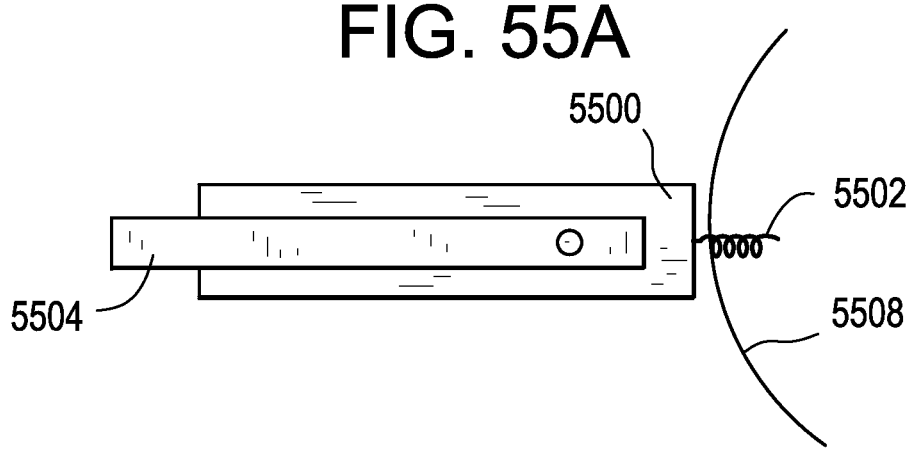
FIG. 55A is a side view of one embodiment of a staple applying assembly including a tissue acquisition member rotatably coupled to stapling jaws.
Figure 55B:
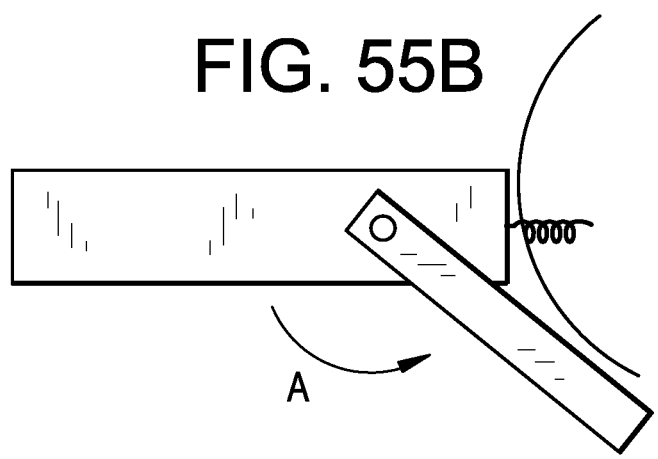
FIG. 55B is a side view of the staple applying assembly of FIG. 55A in a second position.
Figure 55C:
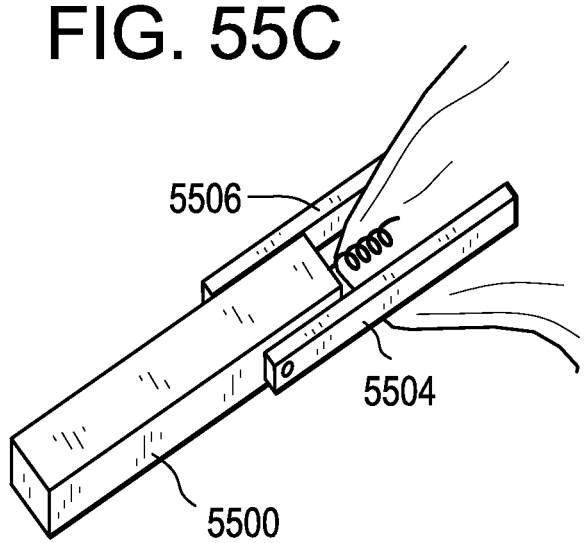
FIG. 55C is a side view of the staple applying assembly of FIG. 55A in a third position.

FIGS. 55A-C illustrate another embodiment of a tissue acquisition member in which stapling jaws rotate into position and draw the tissue acquisition member away from the tissue wall surface. As shown in FIG. 55A, a tissue acquisition member 5500 can include a mechanical grasper 5502 or other tissue engagement element disposed on a distal end thereof. In addition, the tissue acquisition member 5500 can be pivotally coupled to an end of a first and a second stapling jaw 5504, 5506. The first and second jaws 5504, 5506 can be configured to rotate at least 180 degrees about the tissue acquisition member 5500.

In use, the tissue acquisition member 5500 can approach a tissue wall surface 5508 with the first and second jaws 5504, 5506 in a position such that they do not extend beyond a distal end of the tissue acquisition member 5500, as shown in FIG. 55A. After the grasper 5502 engages tissue, the first and second jaws 5504, 5506 can be rotated as shown in FIG. 55B to a position in which they extend beyond a distal end of the tissue acquisition member 5500. As the first and second jaws 5504, 5506 rotate in the direction of arrow A, the tissue acquisition member 5500 will be drawn away from the tissue wall surface 5508, and tissue will be drawn into the space between the first and second jaws, as shown in FIG. 55C. The first and second jaws 5504, 5506 can then be actuated to secure the plication.

Articulating Grasper

Figure 56A:
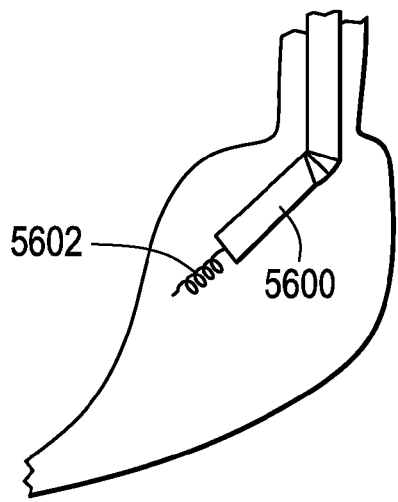
FIG. 56A is front view of one embodiment of a staple applying assembly including articulating stapling jaws.
Figure 56B:
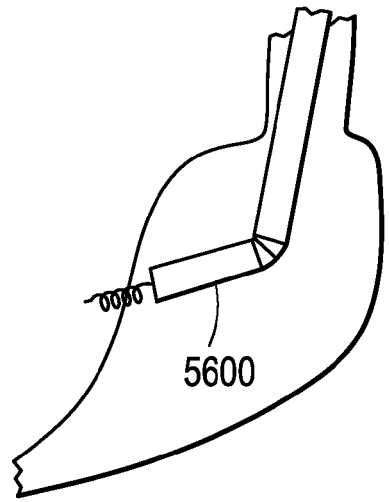
FIG. 56B is a front view of the staple applying assembly of FIG. 56A in a second position.

In the embodiment shown in FIGS. 56A-D, an articulating set of stapling jaws 5600 can be used to secure a gastric plication. To begin, an endoscopic device having an articulating set of stapling jaws 5600 and a tissue grasper 5602 is inserted into a patient's stomach through the esophagus, as shown in FIG. 56A. The device can be positioned over a desired plication site, and can be articulated if necessary to align and engage the tissue grasper 5602 with the stomach wall, as shown in FIG. 56B.

Figure 56C:
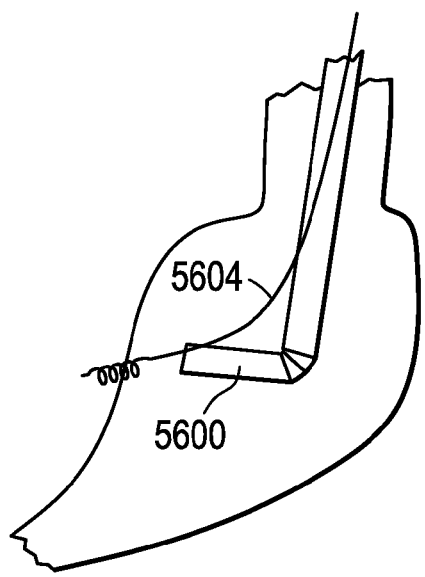
FIG. 56C is a front view of the staple applying assembly of FIG. 56A in a third position.

Once engaged with the tissue of the stomach wall, an actuating cable 5604 connected to the tissue grasper 5602 can be tensioned to draw tissue away from the stomach wall surface, forming a plication. In addition, the actuating cable 5604, which can initially be constrained along the entire length of the device, can be released from a distal portion of the device such that the tissue is drawn in a direction offset from the stapling jaws 5600, as shown in FIG. 56C.

Figure 56D:
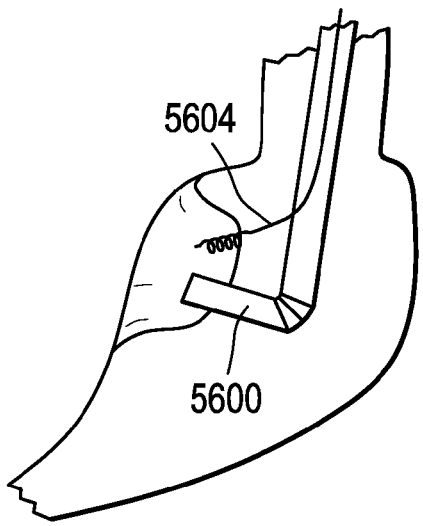
FIG. 56D is a front view of the staple applying assembly of FIG. 56A in a fourth position.

Finally, and as shown in FIG. 56D, the stapling jaws 5600 can be articulated further such that tissue is drawn through the jaws as it is pulled away from the stomach wall surface by the grasper 5602. The stapling jaws can then be actuated to secure the plication with one or more staples or other fasteners.

Articulating Loops

Figure 57A:
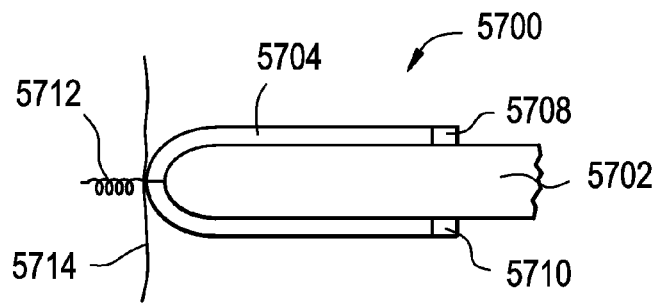
FIG. 57A is a side view of one embodiment of a staple applying assembly including extendable elongate members and an articulating shaft.
Figure 57B:
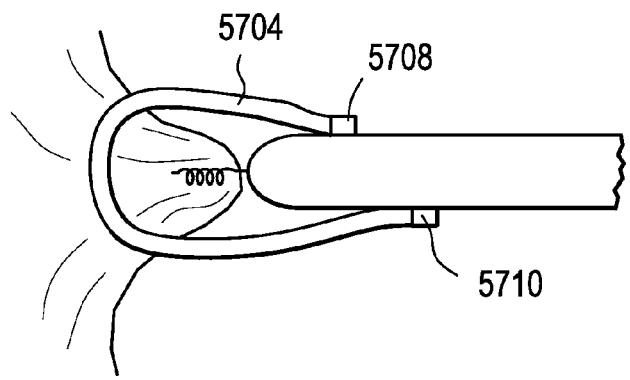
FIG. 57B is a side view of the staple applying assembly of FIG. 57A in a second position.
Figure 57C:
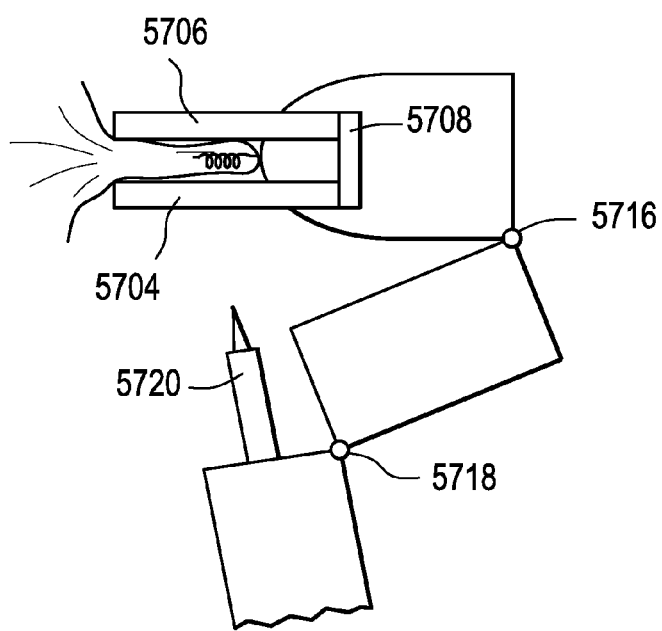
FIG. 57C is a top view of the staple applying assembly of FIG. 57A in a third position.

FIGS. 57A-C illustrate another articulating plication device that utilizes flexible resilient loops to form a gastric plication. As shown in FIG. 57A, the device 5700 can include a shaft 5702 and two elongate members 5704, 5706 formed of a resilient flexible material coupled to the shaft at a first terminal end 5708 and a second terminal end 5710 (note that only one member 5704 is visible in the side view of FIG. 57A because the second member 5706 is directly behind the visible member 5704). The device 5700 can also include a tissue engagement element 5712 (e.g., a corkscrew, a small set of grasping jaws, etc.) located at a distal end of the shaft 5702.

In use, the shaft 5702 can approach a tissue wall surface 5714 such that a longitudinal axis of the device 5700 is perpendicular to the tissue wall surface. The tissue engagement element 5712 can be actuated to engage tissue, and then one or more of the first terminal end 5708 and the second terminal end 5710 can be actuated to advance the elongate members 5704, 5706 toward the tissue wall surface 5714. This can be accomplished, for example, by slidably disposing the first and second terminal ends 5708, 5710 in a track formed on the shaft 5702. Note that only one of the first and second terminal ends must be movable and the other can be fixedly attached to the shaft, as shown in FIG. 57B. Alternatively, both terminal ends can be configured to translate along the shaft 5702.

As the two elongate members 5704, 5706 advance toward the tissue wall surface 5714, they will deform into a loop shape. The tissue engagement element 5712 will also be drawn away from the tissue wall surface, thereby drawing tissue into a space between the two elongate members 5704, 5706 and forming a fold of stomach tissue. To secure the plication formed between the two elongate members 5704, 5706, the shaft 5702 can feature two or more articulating joints 5716, 5718 that allow a fastener element 5720 to approach the plication by passing a fastener through the two loops formed by the resilient flexible members 5704, 5706. The fastener element can extend from the shaft 5702 to pierce the plication and prevent it from flattening after the resilient flexible members 5704, 5706 are removed. FIG. 57C illustrates such articulation from a side view, where each of the elongate members 5704, 5706 are visible.

Assembly & Reconditioning

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, the surgical devices disclosed herein may be disassembled partially or completely. In particular, the stapler portion 900 can be removable from the second jaw 204 to facilitate loading or re-loading of staples. In addition, each of the components of the firing mechanism can be separated from the stapling jaws to facilitate cleaning or repair. Similarly, each of the first jaw, the second jaw, and the tissue acquisition member can be separated from each other, and the entire end effector can be separated from any attached surgical device, such as device 1300 shown in FIG. 13.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A tissue acquisition and fixation system, comprising:
an elongate shaft having proximal and distal ends;
a staple applying assembly having a proximal end coupled to the distal end of the elongate shaft and having first and second jaws, at least one of the jaws being movable such that the first and second jaws have an open position for receiving tissue and a closed position for engaging tissue, the first and second jaws being effective to apply at least one staple to tissue engaged between the first and second jaws; and
a tissue acquisition member coupled to the staple applying assembly by a linkage mechanism, the tissue acquisition member being effective to engage tissue and to position the engaged tissue between the first and second jaws;
wherein the linkage mechanism is configured to move the tissue acquisition member between a first position that is longitudinally offset and proximal to the staple applying assembly, and a second position that is longitudinally adjacent to the staple applying assembly while maintaining a parallel orientation between a longitudinal axis of the tissue acquisition member and a longitudinal axis of the staple applying assembly.

2. The system of claim 1, wherein a distal end of the tissue acquisition member is disposed proximal to the proximal end of the staple applying assembly in the first position, and the distal end of the tissue acquisition member is disposed longitudinally adjacent to a distal end of the staple applying assembly in the second position.

3. The system of claim 1, wherein the first jaw comprises an anvil for forming a staple, and the second jaw comprises a staple cartridge configured to house two or more rows of staples.

4. The system of claim 3, wherein the staple applying assembly further comprises at least one firing wedge in each staple row that is configured to selectively eject at least one staple from the staple row.

5. The system of claim 4, wherein each of the at least one firing wedges is selectively controllable by a user.

6. The system of claim 5, wherein each of the at least one firing wedges is controlled by translation of an actuating cable.

7. The system of claim 1, wherein the tissue acquisition member comprises a vacuum pod configured to couple to a vacuum source and apply a vacuum force to draw surrounding tissue against at least one surface of the tissue acquisition member.

8. The system of claim 7, further comprising a secondary acquirer coupled to the tissue acquisition member and configured to engage tissue and maintain the tissue in position relative to the tissue acquisition member.

9. The system of claim 8, wherein the secondary acquirer is selected from the group consisting of hooks, graspers, or clamps coupled to the tissue acquisition member.

10. The system of claim 1, wherein at least a portion of the tissue acquisition member is movable across a plane defined by a superior surface of the first and second jaws in the second position.

11. The system of claim 1, wherein the linkage mechanism is further configured to move the tissue acquisition member to a third position in which the tissue acquisition member is vertically offset from the first and second jaws such that tissue engaged by the tissue acquisition member is disposed between the first and second jaws.

12. A method of acquiring and fixating tissue, comprising:
pivoting a tissue acquisition member from a position longitudinally proximal to an end effector to a position longitudinally aligned with the end effector while maintaining a parallel orientation between a longitudinal axis of the tissue acquisition member and a longitudinal axis of the end effector;
engaging tissue with the tissue acquisition member and moving the tissue acquisition member to draw tissue through first and second jaws on the end effector;
moving the first and second jaws to a closed position to engage the tissue therebetween; and
actuating the jaws to apply at least one staple through the tissue engaged therebetween.

13. The method of claim 12, wherein pivoting the tissue acquisition member further comprises advancing at least a portion of the tissue acquisition member across a plane defined by a superior surface of the first and second jaws.

14. The method of claim 12, wherein moving the tissue acquisition member to draw tissue through the first and second jaws further comprises moving the tissue acquisition member to a position vertically offset from the first and second jaws.

15. The method of claim 12, further comprising, prior to moving the tissue acquisition member to draw the tissue through the first and second jaws, engaging a secondary tissue acquirer to secure the tissue to the tissue acquisition member.

16. The method of claim 15, wherein the secondary tissue acquirer is selected from the group consisting of hooks, graspers, or clamps coupled to the tissue acquisition member.

17. The method of claim 12, wherein actuating the jaws comprises selectively advancing at least one firing wedge configured to eject at least one staple from at least one of the first and second jaws.

18. The method of claim 17, wherein selectively advancing the at least one firing wedge comprises advancing the at least one firing wedge along a row of staples to drive at least one staple from the row.

19. The method of claim 18, wherein selectively advancing the at least one firing wedge comprises translating at least one actuator cable coupled to the at least one firing wedge.

* * * * *